(12) United States Patent
Fu et al.

(10) Patent No.: US 10,182,766 B2
(45) Date of Patent: Jan. 22, 2019

(54) INTELLIGENT APPARATUS FOR PATIENT GUIDANCE AND DATA CAPTURE DURING PHYSICAL THERAPY AND WHEELCHAIR USAGE

(71) Applicant: UNIVERSITY OF CENTRAL OKLAHOMA, Edmond, OK (US)

(72) Inventors: Jicheng Fu, Edmond, OK (US); Maurice Haff, Edmond, OK (US)

(73) Assignee: University of Central Oklahoma, Edmond, OK (US)

( * ) Notice: Subject to any disclaimer, the term of this patent is extended or adjusted under 35 U.S.C. 154(b) by 16 days.

(21) Appl. No.: 15/010,604

(22) Filed: Jan. 29, 2016

(65) Prior Publication Data

US 2016/0143593 A1    May 26, 2016

Related U.S. Application Data

(63) Continuation-in-part of application No. 14/632,198, filed on Feb. 26, 2015, now Pat. No. 9,922,291, which
(Continued)

(51) Int. Cl.
*A61B 5/00* (2006.01)
*A61B 5/11* (2006.01)
(Continued)

(52) U.S. Cl.
CPC ......... *A61B 5/7264* (2013.01); *A61B 5/0022* (2013.01); *A61B 5/11* (2013.01);
(Continued)

(58) Field of Classification Search
None
See application file for complete search history.

(56) References Cited

U.S. PATENT DOCUMENTS

| 7,246,856 | B2 | 7/2007 | Kruse et al. |
| 8,180,591 | B2 * | 5/2012 | Yuen .................... A61B 5/0002 702/160 |

(Continued)

OTHER PUBLICATIONS

R. Aissaoui, C. Kauffmann, J. Dansereau, and J. A. de Guise, "Analysis of pressure distribution at the body-seat interface in able-bodied and paraplegic subjects using a deformable active contour algorithm," Med Eng Phys, vol. 23, pp. 359-367, Jul. 2001.
(Continued)

*Primary Examiner* — Kakali Chaki
*Assistant Examiner* — Daniel T Pellett
(74) *Attorney, Agent, or Firm* — Berenato & White, LLC

(57) ABSTRACT

A system for guiding and evaluating physical positioning, orientation and motion of the human body, comprising: a cloud computing-based subsystem including an artificial neural network and spatial position analyzer said cloud computing-based subsystem adapted for data storage, management and analysis; at least one motion sensing device wearable on the human body, said at least one motion sensing device adapted to detect changes in at least one of spatial position, orientation, and rate of motion; a mobile subsystem running an application program (app) that controls said at least one motion sensing device, said mobile subsystem adapted to capture activity data quantifying said changes in at least one of spatial position, orientation, and rate of motion, said mobile subsystem further adapted to transfer said activity data to said cloud computing-based subsystem, wherein said cloud computing-based subsystem processes, stores, and analyzes said activity data.

6 Claims, 37 Drawing Sheets

Related U.S. Application Data is a continuation of application No. 14/304,758, filed on Jun. 13, 2014, now Pat. No. 8,996,432.

(60) Provisional application No. 61/891,600, filed on Oct. 16, 2013.

(51) Int. Cl.
    *A61G 5/10*     (2006.01)
    *G06N 3/02*     (2006.01)
    *A61G 7/057*     (2006.01)
    *G06F 19/00*     (2018.01)
    *G16H 50/20*     (2018.01)

(52) U.S. Cl.
CPC .......... *A61B 5/6828* (2013.01); *A61B 5/6898* (2013.01); *G06F 19/00* (2013.01); *G06F 19/3481* (2013.01); *G16H 50/20* (2018.01); *A61G 5/1067* (2013.01); *A61G 5/1075* (2013.01); *A61G 7/057* (2013.01); *A61G 2203/10* (2013.01); *G05B 2219/36442* (2013.01); *G06N 3/02* (2013.01)

(56) References Cited

U.S. PATENT DOCUMENTS

| | | | | |
|---|---|---|---|---|
| 9,098,991 | B2* | 8/2015 | Park | G08B 21/18 |
| 2007/0050111 | A1* | 3/2007 | Mattes | A61G 5/04 |
| | | | | 701/36 |
| 2008/0097256 | A1* | 4/2008 | Torres | A61G 5/045 |
| | | | | 601/24 |
| 2010/0280629 | A1 | 11/2010 | Jung et al. | |
| 2014/0035761 | A1* | 2/2014 | Burton | G01D 4/002 |
| | | | | 340/870.02 |
| 2014/0036643 | A1* | 2/2014 | Messenger | G04G 13/021 |
| | | | | 368/251 |
| 2014/0039842 | A1* | 2/2014 | Yuen | A61B 5/6838 |
| | | | | 702/189 |
| 2014/0107493 | A1* | 4/2014 | Yuen | H04W 4/027 |
| | | | | 600/473 |
| 2014/0197946 | A1* | 7/2014 | Park | G08B 21/18 |
| | | | | 340/539.11 |

OTHER PUBLICATIONS

Y. K. Jan, F. Liao, M. A. Jones, L. A. Rice, and T. Tisdell, "Effect of durations of wheelchair tilt-in-space and recline on skin perfusion over the ischial tuberosity in people with spinal cord injury," Arch Phys Med Rehabil, vol. 94, pp. 667-672, Apr. 2013.

Y. K. Jan, M. A. Jones, M. H. Rabadi, R. D. Foreman, and A. Thiessen, "Effect of wheelchair tilt-in-space and recline angles on skin perfusion over the ischial tuberosity in people with spinal cord injury," Archives of physical medicine and rehabilitation, vol. 91, pp. 1758-1764, Nov. 2010.

Permobil. (2014). Virtual Seating Coach. Available: http://www.permobilus.com/virtualseatingcoach.php.

D. W. Byrne and C. A. Salzberg, "Major risk factors for pressure ulcers in the spinal cord disabled: a literature review," Spinal Cord, vol. 34, pp. 255-263, May 1996.

M. Makhsous, M. Priebe, J. Bankard, D. Rowles, M. Zeigler, D. Chen, and F. Lin, "Measuring tissue perfusion during pressure relief maneuvers: insights into preventing pressure ulcers," The journal of spinal cord medicine, vol. 30, pp. 497-507, 2007.

Gélis A., Dupeyron A., Legros P., Benaïm, C., Pelissier J., and Fattal4 C., "Pressure ulcer risk factors in persons with spinal cord injury Part 2: the chronic stage", Spinal Cord (2009) 47, 651-661.

M. Reddy, S. S. Gill, and P. A. Rochon, "Preventing pressure ulcers: a systematic review," JAMA : the journal of the American Medical Association, vol. 296, pp. 974-984, Aug. 23, 2006.

B. E. Dicianno, et al., "RESNA position on the application of tilt, recline, and elevating legrests for wheelchairs," Assist Technol, vol. 21, pp. 13-22; quiz 24, Spring 2009.

S. E. Sonenblum and S. H. Sprigle, "The impact of tilting on blood flow and localized tissue loading," J Tissue Viability, vol. 20, pp. 3-13, Feb. 2011.

Y.K. Wu, H.Y. Liu, J. Brown, A. Kelleher, H. Wang, R. A. Cooper, "A Smartphone Application for Improving Powered Seat Functions Usage: A Preliminary Test", RESNA Annual Conference—2013.

S. V. Hiremath, D. Ding, and R. A. Cooper, "Development and evaluation of a gyroscope-based wheel rotation monitor for manual wheelchair users," J Spinal Cord Med, vol. 36, pp. 347-356, Jul. 2013.

J. Nixon, G. Cranny, and S. Bond, "Pathology, diagnosis, and classification of pressure ulcers: comparing clinical and imaging techniques," Wound repair and regeneration : official publication of the Wound Healing Society [and] the European Tissue Repair Society, vol. 13, pp. 365-372, Jul.-Aug. 2005.

F. Liao, S. Burns, and Y.-K. Jan, "Skin blood flow dynamics and its role in pressure ulcers," Journal of Tissue Viability, vol. 22, pp. 25-36, 2013.

Y. K. Jan and M. B. David, "Technology for Pressure Ulcer Prevention," Topics in Spinal Cord Injury Rehabilitation, vol. 11, pp. 30-41, 2006.

fu, Jicheng, et al. "Capturing and analyzing wheelchair maneuvering patterns with mobile cloud computing." Engineering in Medicine and Biology Society (EMBC), 2013 35th Annual International Conference of the IEEE. IEEE, 2013.

Fu, Jicheng, Yih-Kuen Jan, and Maria Jones. "Development of intelligent model to determine favorable wheelchair tilt and recline angles for people with spinal cord injury." Engineering in Medicine and Biology Society, EMBC, 2011 Annual International Conference of the IEEE. IEEE, 2011.

Barea, Rafael, et al. "EOG guidance of a wheelchair using spiking neural networks." ESANN. 2000.

Liu, Hsin-Yi, et al. "Seating virtual coach: A smart reminder for power seat function usage." Technology and Disability 22.1 (2010): 53-60.

Fu, Jicheng, et al. "Towards an intelligent system for clinical guidance on wheelchair tilt and recline usage" Engineering in Medicine and Biology Society (EMBC), 2012 Annual International Conference of the IEEE. IEEE, 2012.

Fu, Jicheng, et al. "Using Artificial Neural Network to Determine Favorable Wheelchair Tilt and Recline Usage in People with Spinal Cord Injury: Training ANN with Genetic Algorithm to Improve Generalization." Tools with Artificial Intelligence (ICTAI), 2011 23rd IEEE International Conference on. IEEE, 2011.

* cited by examiner

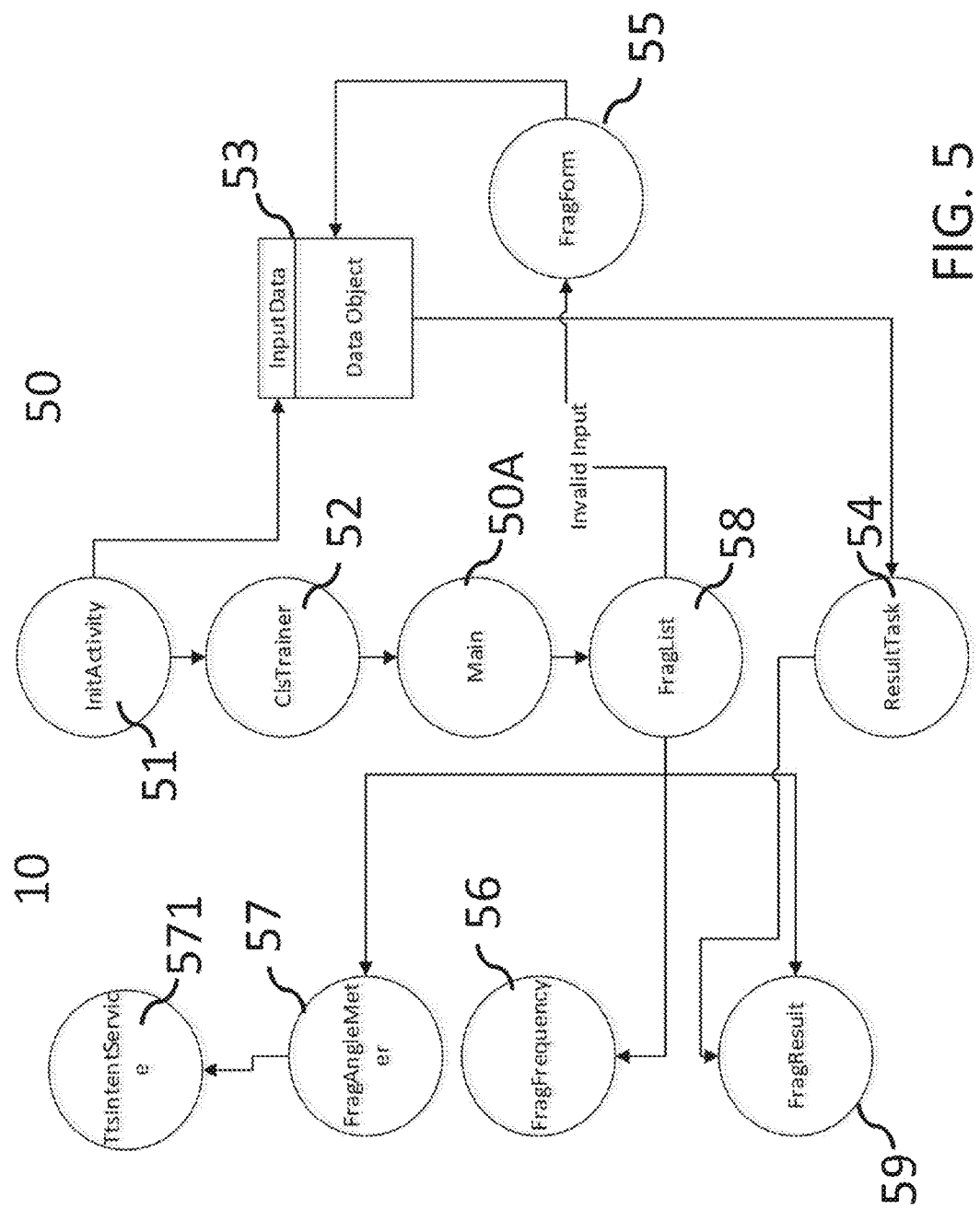

INTELLIGENT APPARATUS FOR PATIENT GUIDANCE AND DATA CAPTURE DURING PHYSICAL THERAPY AND WHEELCHAIR USAGE

CROSS REFERENCES TO RELATED APPLICATIONS

This application is a continuation-in-part of U.S. patent application Ser. No. 14/632,198 filed on Feb. 26, 2015 entitled "Intelligent apparatus for providing personalized configuration of wheelchair tilt and recline", which is a continuation of U.S. patent application Ser. No. 14/304,758 filed on Jun. 13, 2014, entitled "Intelligent apparatus for providing personalized configuration of wheelchair tilt and recline" now U.S. Pat. No. 8,996,432 issued Mar. 31, 2015; the disclosures of which, including code listings filed on Compact Disk, are expressly incorporated herein by reference in their entireties. This application is also based on and claims the benefit of U.S. Provisional Patent Application No. 61/891,600 filed on Oct. 16, 2013 in the name of Jicheng Fu, entitled "Intelligent apparatus for providing personalized configuration of wheelchair tilt and recline" the disclosure of which is expressly incorporated herein by reference in its entirety.

STATEMENT AS TO RIGHTS TO INVENTIONS MADE UNDER FEDERALLY SPONSORED RESEARCH OR DEVELOPMENT

This invention was made with government support under Grant Number 8P20GM103447awarded by the National Institutes of Health. The government has certain rights in the invention.

FIELD OF THE INVENTION

The present invention relates to providing personalized configuration of physical supports and guidance for rehabilitation of the human body. More particularly, the present invention relates to optimization of physical supports and human positioning to achieve a desired outcome, including reducing the risk of pressure ulcers in general, reducing the risk of pressure ulcers for people with spinal cord injury (SCI), and improving outcomes of physical conditioning and rehabilitation therapy.

REFERENCE TO COMPUTER PROGRAM LISTING APPENDICES ON CD-R

This application includes herewith a transmittal under 37 C.F.R § 1.52(e) of a Computer Program Listing Appendix on Compact Disk (CD), where the transmittal comprises duplicate compact discs (CDs), totaling two (2) CDs, respectively labeled "Copy 1 Appendix A" and "Copy 2 Appendix A". Each disk contains the same file. The discs are IBM-PC machine formatted and MICROSOFT WINDOWS Operating System compatible, and include identical copies of the following file, where the file has been saved as a document viewable using MICROSOFT WORD. All of the materials on the compact disk, including the computer program listings, are incorporated herein by reference in their entirety. The file is a Code Listing (174,080 bytes on disk). The referenced listings were created on Jan. 9, 2016.

The Table of Contents for the Code Listing file is as follows:

| Table of Contents | |
|---|---|
| Wheelchair Tilt and Recline | 2 |
| Implementation that Supports Microsoft Band | 2 |
| Main | 2 |
| AccelerometerStrategy | 3 |
| AngleCalculationStrategy | 3 |
| FragmentAngleMeter | 3 |
| FragmentSettings | 11 |
| FragmentSignIn | 12 |
| FragmentSleepItemEdit | 14 |
| FragmentSleepSettings | 16 |
| FragmentStatDetail | 18 |
| FragmentStats | 21 |
| AngleDataManager | 23 |
| AngleMeterSensorManager | 31 |
| AngleStatisticsManager | 32 |
| BandSensorManager | 37 |
| PhoneSenorManager | 38 |
| TimerManager | 39 |
| SleepPeriod | 40 |
| BandAccelerometerListener | 44 |
| PhoneAccelerometerListener | 45 |
| InternalStorage | 45 |
| LocalDataOpenHelper | 46 |
| DayListAdapter | 46 |
| SleepListAdapter | 48 |
| AngleMeterAdjustmentLogic | 50 |
| AngleMeterBackgroundService | 63 |
| AngleReminderReceiver | 84 |
| Implementation that Supports Google Glass | 84 |
| AngleDataManager | 84 |
| AngleMeterListener | 92 |
| AngleMeterService | 102 |
| ContinuousRecognitionListener | 115 |
| LiveCardMenuActivity | 117 |
| LocalDataOpenHelper | 119 |
| Knee Recovery | 120 |
| ShoulderAndKneeRecovery | 120 |
| GyroscopeStrategy | 120 |
| AccelerometerStrategy | 121 |

BACKGROUND OF THE INVENTION

Negative physiological conditions (e.g., attention deficit, lower back pain, pressure ulcers) may be experienced by people who are seated for long periods of time (e.g., long-haul truck drivers, airline pilots). Pressure ulcers are often experienced by people having compromised mobility (e.g., the elderly and infirm). People inflicted with spinal cord injury (SCI) are particularly prone to developing pressure ulcers. A pressure ulcer is any lesion caused by unrelieved pressure that results in damage of underlying tissue. Pressure ulcers may develop following a prolonged period of compression of the tissue between a bony prominence and a surface.

Unrelieved pressure may result in occlusion of capillaries and lead to ischemia, which has historically been considered a major factor leading to pressure ulcer formation. The cost of treating an individual pressure ulcer ranges up to $40,000 but can exceed $100,000 depending on severity of the wound. Up to 24% of persons residing in nursing homes reportedly have developed a pressure ulcer (also called bed sores). When a person is in a seated position, his or her weight typically rests on a section of the pelvic girdle called the ischial tuberosity (specifically, the inferior, posterior portion of the ischium). There are two of these bony swellings, left and right, sometimes called the sitting bones, which are located on the posterior, inferior portion of the ischium. The gluteus maximus muscle lies over it when a person is standing; however, when he or she sits down, the muscle shifts to a position that exposes the ischium tuberosity, which then bears the majority of the weight, and pressure ulcers may occur.

Pressure ulcers are a frequently occurring healthcare problem throughout the world. Pressure ulcers pose a significant threat to the quality of life for people confined to wheelchairs, such as persons inflicted with spinal cord injury (SCI). Pressure ulcers once formed may lead to sepsis and early death. Pressure ulcers remain the most common secondary condition associated with SCI, and has been reported to occur in from 28% to 85% of patients with SCI, often within a few days of injury. It is estimated that more than half of the SCI population will develop at least one pressure ulcer in their lifetimes. In Europe, treatment of illness associated with pressure ulcers has been estimated to result in up to 4% of total healthcare expenditure. The United States alone spends about $1.4 billion annually on the treatment of pressure ulcers for people with SCI. It has been estimated that the cost of treating pressure ulcers is 2.5 times the cost of preventing them. Considering the numbers and cost of treatment, pressure ulcers are an important public health problem. There is an urgent and growing need to develop effective modes of prevention and treatment.

Although wheelchair tilt and recline functions are typically used for pressure ulcer prevention, present approaches cannot determine at what angles wheelchair tilt and recline provide effective prevention of pressure ulcers. Clinicians typically recommend uniform guidance to all patients. However, clinical evidence clearly shows that the SCI individuals demonstrate a wide variety of requirements. Consequently, universal guidelines cannot satisfy all the needs. Hence, personalized configuration of wheelchair tilt and recline for each individual is more desirable and beneficial.

It is known that traditional statistical methods can be used to model biomedical problems. However, statistical methods are found less capable of finding patterns, dealing with data that may contain noise, or analyzing non-linear and dependent data. Artificial intelligent techniques on machine learning, on the other hand, have played increasingly important role in bioinformatics for classifying and mining data. Such techniques can capture patterns based on examples (i.e., training data) even though the underlying nature, principles, and/or probability distributions may not be clear. It is, therefore, an object of the present invention to use an artificial intelligent (AI) module (artificial neural network in the current implementation) to provide a method and apparatus with which to discover patterns driven by individual human conditions, operational environments, and outcome or use objectives. It is a further objective of the present invention to provide personalized guidance and configuration control for seating support, adjustment, and positioning including wheelchair tilt and recline usage for people confined to wheelchairs and who may be inflicted with SCI.

Tilt and recline (TR) functions are two of the most desirable features on a wheelchair for relieving seating pressure. Tilt refers to a change of the seat angle orientation while maintaining the seat-to-back angle and recline refers to a change of the seat-to-back angle. Despite the importance of TR functions, the majority of the wheelchairs do not offer a built-in mechanism to measure TR angles. Wheelchair users tend to adjust TR angles based on their own preferences and perceptions. However, research shows that wheelchair users rarely adjust enough tilt or recline angles to relieve seating pressure, which has been recognized as a major causative factor of pressure ulcers (PUs). The reasons for the ineffective usage of wheelchair TR functions are in part due to the lack of a convenient way to measure wheelchair TR angles, and in part due to the lack of a practical way to monitor whether wheelchair users follow the clinical guidelines of wheelchair TR usage.

In addition, for work-related injuries alone, knee and shoulder injuries were among the most common nonfatal single injury types. Further, injury to the knee, shoulder, and ankle are common among athletes. Shoulder and knee injuries were identified as the most expensive injury types in terms of total costs (average cost per claim×number of claims). Traditionally, self-report is a major approach for evaluating the rehabilitation progress. However, self-report may be very subjective and could lead to serious results. For example, many people with knee injuries will not be able to recover to the level of pre-injury. Hence, an effective and convenient recovery approach is very desirable to improve recovery quality and reduce the cost.

SUMMARY OF THE INVENTION

Pressure ulcers (PUs) impose a significant threat to the quality of life of wheelchair users. Prolonged unrelieved seating pressure has been identified as a major causative factor of PUs. Wheelchair tilt and recline (TR) functions are two of the most desirable features on a wheelchair for relieving seating pressure. Tilt refers to a change of the seat angle orientation while maintaining the seat-to-back angle and recline refers to a change of the seat-to-back angle. Despite the importance of TR functions, the majority of the wheelchairs do not offer a built-in mechanism to measure TR angles. Wheelchair users tend to adjust TR angles based on their own perceptions. However, research shows that wheelchair users rarely adjust enough tilt or recline angles to relieve seating pressure, which has been recognized as a major causative factor of pressure ulcers. The reasons for the ineffective usage of wheelchair TR functions are in part due to the lack of a convenient way to measure wheelchair TR angles, and in part due to the lack of a practical way to monitor whether wheelchair users follow the clinical guidelines of wheelchair TR usage.

The present invention enables a user to obtain a set of favorable tilt and recline combinations derived from the user's specific profile that can help reduce the risk of pressure ulcers. A profile may include information comprising the user's age, gender, height, weight, body mass index, level of injury, completeness of injury, duration of injury, age at onset of injury (e.g., SCI, stroke, amputation), whether he/she smokes, drinks alcohol, exercises, and/or has pressure ulcer history. An overall picture of the user's favorable tilt and recline settings are presentable, along with choices to adjust seating positions. Users are also presented with the best TR functions that can most effectively reduce risk of pressure ulcers.

The present invention provides a unique way to effectively use wheelchair TR functions, even though most wheelchairs in use today do not offer a built-in mechanism for measuring TR angles. Smart mobile devices (smartphones and tablets) are configurable using the methods of the present invention to accurately measure TR angles. For example, the advanced computational process of the present invention enables users to conveniently measure wheelchair TR angles by simply positioning a smartphone configured in accordance with the present invention in their pockets (e.g., shirt pocket). Further, through the combined use of mobile and cloud computing, the methods of the present invention enable automatic transmission of wheelchair TR usage information to "cloud-based" storage and remote analysis.

Cloud computing is often defined as the practice of using a network of remote servers hosted on the Internet to store, manage, and process data, rather than a local server or a personal computer. Cloud storage involves storing data on multiple virtual servers that are generally hosted by third parties. The term "cloud" as used herein generally refers to cloud computing, cloud storage, and the World Wide Web. Hence, through the use of cloud computing and web-based approaches, healthcare providers and researchers can effectively monitor whether the TR guidelines are properly carried out in wheelchair users' natural settings (e.g., home, office, community, etc.). The present invention works for both power and manual wheelchairs, provided they are equipped with tilt or tilt and recline functions. Hence, functionality of both new and existing wheelchairs can be significantly improved through use of the present invention.

The present invention may be implemented in multiple non-limiting versions, including a local device (e.g., smartphone) version, a mobile-cloud version, and a web-cloud version. In one preferred embodiment, the local version, all the functionality may be implemented locally in a smartphone, or similar mobile device, as well as computationally capable sensory devices (e.g., smartgarment, smartheadgear). The local version embodiment may be preferable for use by individuals with limited data transfer and bandwidth capacity. However, a fully localized embodiment implies that the same artificial intelligent (AI) module (at least an artificial neural network in one preferred embodiment) may have to be implemented multiple times for different mobile operating systems, such as Android, iOS, and Windows. Alternative embodiments may be preferable for users where data transfer and bandwidth capacity is sufficient, such as a clinical setting. The artificial intelligent (AI) module and data storage may be extracted from the local version and implemented as a cloud computing model in the Internet cloud. In this preferred embodiment, only one implementation of the artificial intelligent (AI) module is needed, and both the artificial intelligent (AI) module and the data storage may be accessed from a mobile device or a web-based user interface. The local version (e.g., smartphone application) as well as the web application are responsible for collecting user's information, requesting guidance on wheelchair tilt and recline usage or other position and motion parameters, displaying results to the users. A goniometer or other motion sensing device implemented on the local device measures wheelchair tilt and recline angles, or physical positioning of the human body or appendages depending on the intended purpose.

In the present invention, wearable smart mobile devices (e.g., Apple Watch, Microsoft Band, Android Watch, Google Glass, smartphones, etc.), as well as wearable garments, head gear, or body attachments and supports equipped with at least motion sensing devices (e.g., inertial sensors) are adapted to accurately measure angles for wheelchair tilt and recline, as well as movement range and relative motion of the human body during physical conditioning or activity, and during rehabilitation therapy. In preferred embodiments, these motion sensing devices may be configured to record motion data and transfer the data recorded to another mobile device (e.g., smartphone), using for example Bluetooth or WiFi. The Intel Curie™ Module is an example of such a motion sensing device. In some preferred embodiments, the artificial intelligent (AI) module is operable on the mobile device or the motion sensing device, while in other preferred embodiments the artificial intelligent (AI) module is operable on the cloud computing-based subsystem. The mobile architecture of the present invention is adapted for a plurality of user environments, including but not limited to clinical settings, a user residence, and physical activity venues. Further, the present invention may be adapted to detect sudden motion resulting from physical impact and determine the level of force applied on the human body by the impact. Recording and quantification of impact may be used in assessing possible injury (e.g., concussion, joint damage), and data collected may be uploaded to the cloud computing-based subsystem for analysis using at least the artificial intelligent (AI) module, and provided as input for therapeutic decisions. In preferred embodiments, the present invention provides novel voice techniques to guide patients to correctly carry out the clinical protocols and also periodically remind them of performing the prescribed activities. In addition, the present invention provides the functionality needed to record these activities and send the corresponding data to a cloud computing-based subsystem for storage and analysis. Hence, the physicians and therapists are provided with a capability to readily monitor whether the patients have followed rehabilitation guidelines, determine relative levels of physical attainment or recovery, and obtain definitive data and assessments on which to base adjustments to therapies and protocols prescribed.

In a broad aspect, the apparatus of the present invention accepts input that may comprise an individual's demographic information, neurological attributes, physical history, operational environment, and outcome or use objectives, then returning guidance and/or control parameters directed to positioning and adjustment of physical supports for the human body.

In another aspect, the present invention may be embodied as a specific purpose mobile device comprising a computational framework, artificial neural network, a goniometer, and minimum functionality necessary for configuration and control of positioning and adjustment directed to seating supports for the human body.

In another aspect, the present invention provides functions and analytical processes capable of finding patterns, dealing with data that may contain noise, or analyzing non-linear and dependent data.

In yet another aspect, the present invention may be embodied as a specific purpose device integrated into a powered seating apparatus, where the device comprises a computational framework, artificial neural network, a goniometer, and minimum functionality necessary for configuration and control of seating support configuration.

In another aspect, the present invention may comprise a computational framework, artificial neural network, and application instruction set operable on mainstream general purpose mobile devices including "smartphones" (e.g. iPhone, Samsung Galaxy), tablets computers (e.g., iPad), Google glass, AppleWatch, Intel Curie™ Module, etc., collectively "smart devices," running operating systems such as Android, iOS, and MS-Windows, where such devices include at least an accelerometer.

In another aspect, the artificial neural network in the present invention is embodied as an artificial intelligence (AI) module trained with clinical research data directed to optimal positioning and adjustment of physical supports for the human body for a defined purpose or desired outcome.

In another broad aspect, the apparatus of the present invention accepts input comprising an individual's demographic information, neurological attributes, and pressure ulcer history and provides guidance or control parameters directed to: (1) the favorable wheelchair tilt and recline settings; (2) the optimal wheelchair tilt and recline angles that may most effectively reduce pressure ulcer risks; and (3) the measurement of tilt and recline angles by implementing a goniometer.

In another aspect, the present invention may be configured to provide optimal duration and frequency to perform wheelchair tilt and recline functions in response to input comprising an individual's demographic information, neurological attributes, and pressure ulcer history.

In another aspect, the present invention may be configured to measure wheelchair tilt and recline angles (i.e., a goniometer), periodically remind the wheelchair user of performing wheelchair tilt and recline, record wheelchair tilt and recline usage information, including the time when the wheelchair user performs the tilt and recline functions, the angles of the tilt and recline, the duration on which the user maintains the tilt and recline position, and the derived frequency, i.e., how often the wheelchair user repositions himself/herself by means of wheelchair tilt and recline.

In another aspect, the goniometer can work independently of the artificial neural network and intelligent module, and operable on mainstream general purpose mobile devices including "smartphones" (e.g. iPhone, Samsung Galaxy), tablets computers (e.g., iPad), Google Glass, AppleWatch, Intel Curie™ Module, etc., collectively "smart devices," running operating systems such as Android, iOS, and MS-Windows, where such devices include at least an accelerometer.

In another broad aspect, the present invention may be embodied as a specific purpose mobile device comprising a computational framework, artificial neural network, a goniometer, and minimum functionality necessary for configuration and control of wheelchair tilt and recline.

In yet another aspect, the present invention may be embodied as a specific purpose device integrated into a powered wheelchair, where the device comprises a computational framework, artificial neural network, a goniometer, and minimum functionality necessary for configuration and control of wheelchair tilt and recline.

In another aspect, the present invention may comprise a computational framework, artificial neural network, and application instruction set operable on mainstream general purpose mobile devices including "smartphones" (e.g. iPhone, Samsung Galaxy), tablets computers (e.g., iPad), Google glass, AppleWatch, Intel Curie™ Module, etc., collectively "smart devices," running operating systems such as Android, iOS, and Windows, where such devices include an accelerometer.

In another broad aspect, the present invention combines mobile computing and artificial intelligence techniques, incorporating an artificial intelligence (AI) module in an application instruction set operable on a mobile device.

In another aspect, the AI module may be trained with clinical research data on clinically recommended tilt and recline angles, and other position parameters.

In another aspect, smart device users may input into the user interface of the present invention their demographic, neurological, and pressure ulcer history information, and recommended wheelchair tilt and recline angles will be determined favorable for the individual to reduce risk of pressure ulcers.

In another aspect of the present invention, the user interface of the present invention may be configured to display the recommended wheelchair tilt and recline angles, or other position parameters.

In another aspect of the present invention, recommended wheelchair tilt and recline angle may be output from a mobile embodiment of the present invention to a control function operating in a powered wheelchair or other powered mobility device.

In another aspect of the present invention, recommended wheelchair tilt and recline angle may be transferred wirelessly to a controller operational to adjust configuration orientation of a powered wheelchair or other powered mobility device.

In a yet another broad aspect of the present invention, an artificial intelligent module is provided comprising an artificial neural network (ANN) having a layered network structure, in which processing units (i.e., neurons) are arranged in layers, where the neurons in adjacent layers can communicate with each other by sending and receiving signals through weighted connections.

In another aspect, the input/output behavior of a neuron is defined by its internal activation function, which accumulates the input signals and then calculates the outputs.

In another aspect, a learning process proceeds in iterations by tuning the weights of connections using a training algorithm (e.g., the back-propagation algorithm).

In another aspect, a user registration component is provided, which allows users to create their own profiles to record their demographic information (e.g., gender, weight, height, etc.), neurological information (e.g., level of injury, completeness of injury, etc.), and pressure ulcer history (i.e., whether he/she once developed pressure ulcers).

In another aspect of the present invention, the output includes (1) a range of tilt and recline angles that are favorable for pressure reduction for the user; and (2) the optimal tilt and recline angles that are most effective in reducing the risk of pressure ulcers.

In another aspect, the present invention may be configured to provide optimal frequency and duration to perform wheelchair tilt and recline functions, including guidance such as "perform tilt and recline every 15 minutes (i.e., frequency) and maintain the tilt and recline setting for at least 3 minutes (i.e., duration)."

In another aspect of the present invention, a goniometer is provided, which uses an accelerometer sensor in a smart device (e.g., smartphone or tablet) to measure angles of wheelchair tilt and recline.

In another aspect of the present invention, a goniometer measures current wheelchair tilt and recline angle and contrasts those angles with guidance angles to generate control parameters that cause the tilt and recline angle of a powered wheelchair or other powered mobility device to be rotated to a precise angular position.

In another aspect of the present invention, a goniometer may be configured to periodically remind the wheelchair user of performing wheelchair tilt and recline, and record wheelchair tilt and recline usage information, including the time when the wheelchair user performs the tilt and recline functions, the angles of the tilt and recline, the duration on which the user maintains the tilt and recline position, and the derived frequency, i.e., how often the wheelchair user repositions himself/herself by means of wheelchair tilt and recline.

In another aspect of the present invention, the goniometer utilizes advanced math and physics methods to establish a model of the mobile device, which is able to accurately measure wheelchair TR angles no matter how the user positions the mobile device. As a result, the wheelchair user can place the smartphone into his/her pocket while accurately measuring the tilt and recline angles.

In another aspect of the present invention, a goniometer uses voice alerts to guide the usage of wheelchair tilt and recline. As a result, the wheelchair user can place the smartphone into his/her pocket while measuring the tilt and recline angles.

In another aspect of the present invention, a goniometer can work independently without relying on the artificial neural network and intelligent module.

In another aspect of the present invention, the network structure and weights of the artificial neural network are determined offline by using clinical research data on clinically recommended tilt and recline angles, or other position parameters.

In another aspect of the present invention, the artificial neural network is fully configurable through adjusting the network structure and weights.

In another aspect of the present invention, the artificial neural network operable in the AI module can be replaced by other artificial intelligence techniques, namely, any classification, clustering, and regression techniques.

In another broad aspect, the present invention is operable in a mobile-to-cloud configuration, where the AI module is implemented in a cloud computing platform, and the use of cloud-computing ("the cloud") will enable smart devices running on different operating systems to share the same AI module in the cloud.

In another aspect of the present invention, where the AI module is operable in the cloud, the smart device will be responsible for at least collecting user's information, requesting guidance on wheelchair tilt and recline usage or other position parameters, displaying results to the users, and using an implemented goniometer to measure wheelchair tilt and recline angles, balancing workload between mobile and cloud and simplifying maintenance and upgrade.

In another aspect of the present invention, where the AI module is operable in the cloud, the smart device may output adjustment parameters to a control device operational in a powered seating apparatus (e.g. powered wheelchair).

In another broad aspect, the present invention provides actionable aural guidance to achieve recommended tilt and recline settings suitable to a particular wheelchair user based on his/her own profile.

In another aspect, the present invention enables measurement, display, and auditory notification of tilt and recline angles in near real-time as a user adjusts tilt and recline settings on a wheelchair.

In another aspect, the present invention provides remote monitoring and analytics as to whether or not wheelchair users follow recommended tilt and recline guidance.

In another broad aspect of the present invention, a goniometer measures current user positioning angles and contrasts those angles with clinical guidance to generate control parameters that cause the seating position of a powered seating apparatus to be altered to a precise angular position.

In another broad aspect of the present invention, a method is provided for determining spatial orientation of a computational device configured with an accelerometer, comprising: providing a positioning model of said computational device, said positioning model including a vector $v=<\alpha_x, \alpha_y, \alpha_z>$ representing accelerations in three axes measured by said accelerometer; utilizing the dot product property $\theta = \arccos(v_1 \cdot v_2 / |v_1| \times |v_2|)$ to calculate angle changes between at least two vectors; where dynamic positioning of said computational device is calculated relative to any reference physical orientation.

In another aspect, the present invention includes the computational device implemented on a mobile device configured to measure incline angles which may include tilt and recline angles.

In a broad aspect, the present invention provides an integrated system, in which a mobile subsystem controls motion sensors, measures prescribed angles, and transmits activity data to the cloud, while a cloud computing-based subsystem handles subsequent data management and analysis.

In another aspect, the mobile subsystem can operate independently by itself without interacting with the cloud computing-based subsystem.

In another aspect, the mobile subsystem comprises a smartphone and at least one wearable mobile device.

In another aspect, the present invention is adapted to model wearable mobile devices to enable accurate measurement of angles and motion no matter how the user positions the mobile device.

In another aspect, sensor data collected by the wearable mobile device is sent to the smartphone.

In another aspect, the present invention can aid wheelchair users in measuring wheelchair TR prescribed angles.

In another aspect, the present invention can aid patients engaged in physical therapy in achieving proper motion technique and measuring prescribed range and angle of motion angles.

In another aspect, at least one wearable sensor device (e.g., clothing incorporating Intel Curie™ Modules to create smartclothing or head gear) is mounted on a wearer's body so movements can be measured and concomitant data captured.

In another aspect, a smartphone arm-band or other attachment means is used to mount the smartphone on a wearer's arm and measure arm movement.

In another aspect, at least one wearable mobile device (e.g., Microsoft Band, smartwatch, smartclothing, Intel Curie™ Module, motion sensor) is mounted on a wearer's arm so that arm movements can be measured.

In another aspect, a smartphone leg-band or other attachment means is used to mount the smartphone on a wearer's leg and measure leg movement.

In another aspect, at least one wearable mobile device (e.g., Microsoft Band, smart watch, smartclothing, Intel Curie™ Module, motion sensor) is mounted on a wearer's leg so that leg movements can be measured.

In another aspect, at least one wearable mobile device (e.g., Microsoft Band, smart watch, smartclothing, smart-helmet, Intel Curie™ Module, motion sensor) is mounted on a wearer's head so that head movements can be measured.

In another aspect, the present invention provides a user interface accessible in a cloud computing-based subsystem that enables healthcare providers and researchers to monitor and analyze whether patients follow guidelines they prescribe or assess levels of injury.

In another broad aspect, the present invention provides a system for guiding physical positioning, orientation, and motion of the human body, comprising a cloud computing-based subsystem including an artificial neural network and spatial position analyzer, the cloud computing-based subsystem being adapted for data storage, management and analysis.

In another aspect, the system provided by the present invention further comprises at least one motion sensing device wearable on the human body, the at least one motion sensing device being adapted to detect changes in at least one of spatial position, orientation, and rate of motion.

In another aspect, the system provided by the present invention further comprises a mobile subsystem running an application program (app) that controls at least one motion sensing device, the mobile subsystem being adapted to capture activity data quantifying changes in at least one of spatial position, orientation, and rate of motion.

In another aspect the mobile subsystem is further adapted to transmit activity data to the cloud computing-based subsystem, wherein the cloud computing-based subsystem processes, stores, and analyzes the activity data.

BRIEF DESCRIPTION OF THE DRAWINGS

FIG. 5 is a non-limiting diagram showing top-level code structure for a smart mobile device application (i.e., the local version).

FIG. 11a is a non-limiting diagram showing a screen shot of a smartphone implementation providing a user interface to enter demographic attributes.

FIG. 11b is a non-limiting diagram showing a screen shot of a web-based implementation providing a user interface to enter demographic attributes.

DETAILED DESCRIPTION OF PREFERRED EMBODIMENTS OF THE INVENTION

Figure 1:
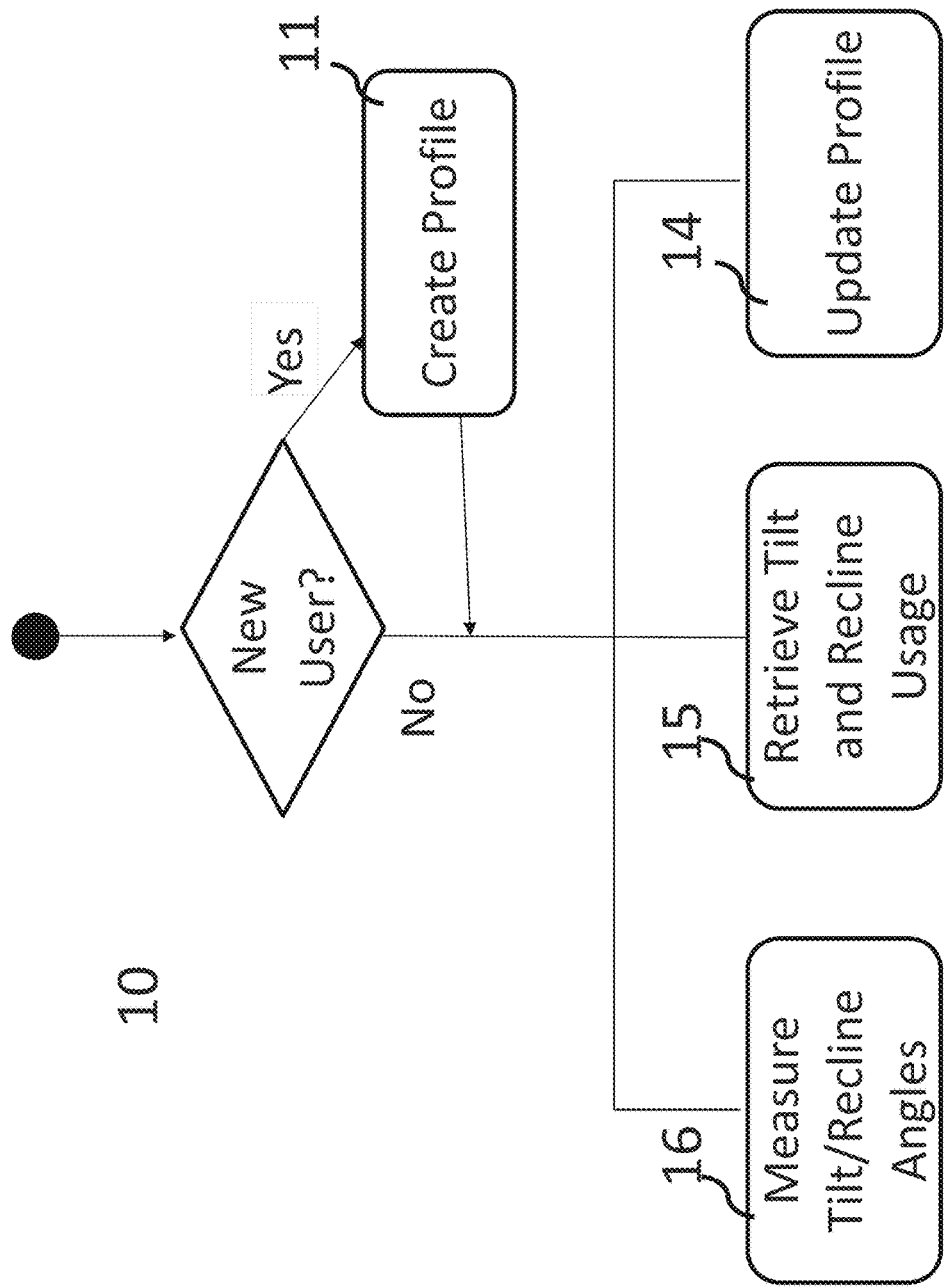
FIG. 1 is a non-limiting diagram showing a process flow directed to an embodiment of the present invention using a smartphone implementation (i.e., the local version). Users must create their profiles before they can use the system. A profile may include information comprising the user's age, gender, height, weight, body mass index, level of injury, completeness of injury, duration of injury, age at onset of SCI, whether he/she smokes, drinks alcohol, exercises, and/or has pressure ulcer history.

In brief: FIG. 1 is a non-limiting diagram showing the process flow directed to use of a smartphone implementation of the present invention (i.e., the local version). Users must create their profiles before they can use the system. A profile may include information comprising the user's age, gender, height, weight, body mass index, level of injury, completeness of injury, duration of injury, age at onset of SCI, whether he/she smokes, drinks alcohol, exercises, and/or has pressure ulcer history. With a valid profile, the user has the options to update his/her profile, retrieve recommendations for wheelchair tilt & recline usage, and use the goniometer implemented in the smartphone to measure wheelchair tilt/recline angles.

Figure 2:
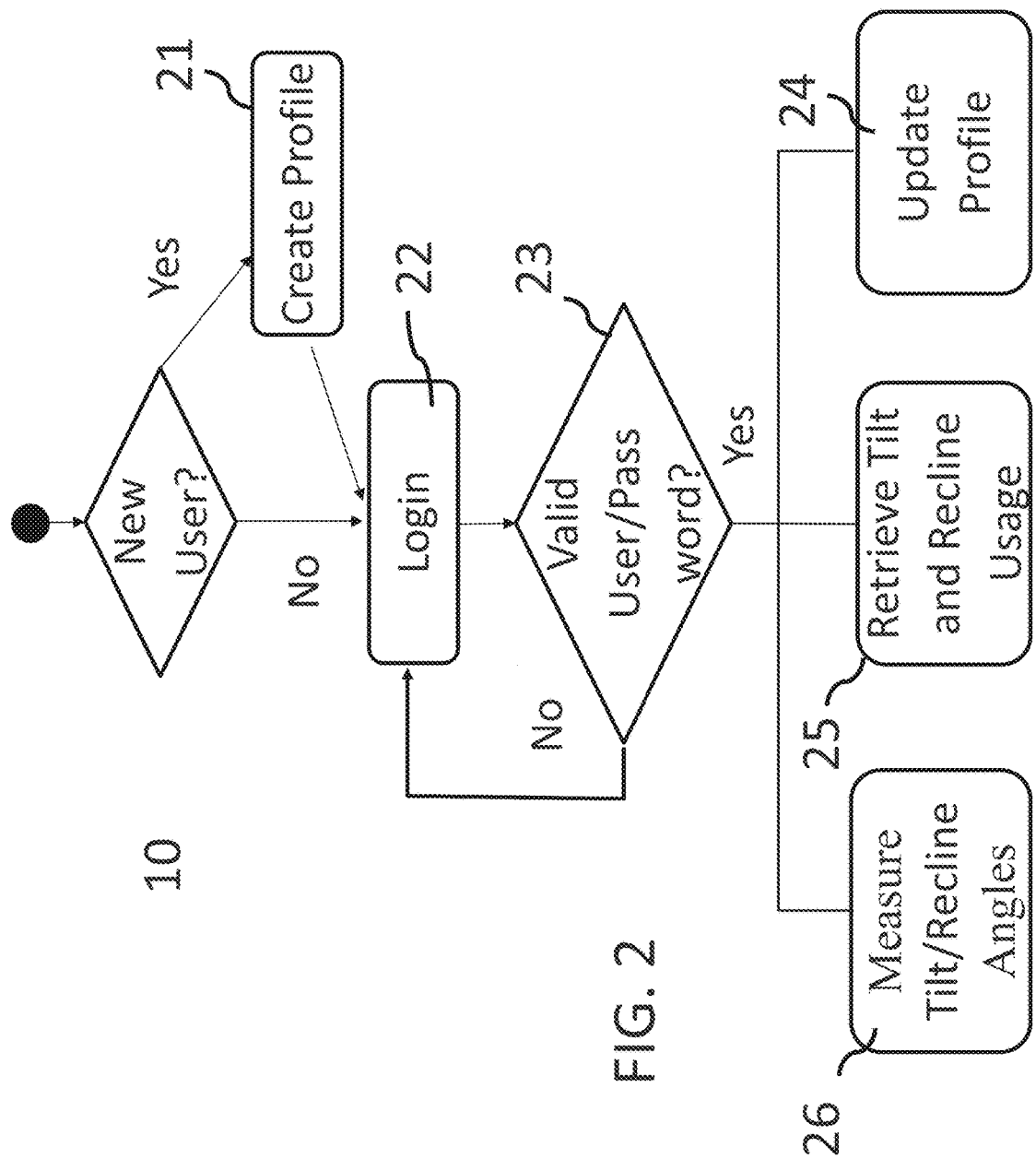
FIG. 2 is a non-limiting diagram showing a process flow directed to an embodiment of the present invention using the mobile-to-cloud implementation. Users must register to create their profiles before they can login. A profile may include information comprising the user's age, gender, height, weight, body mass index, level of injury, completeness of injury, duration of injury, age at onset of SCI, whether he/she smokes, drinks alcohol, exercises, and/or has pressure ulcer history.

FIG. 2 is a non-limiting diagram showing the process flow directed to use of the mobile-to-cloud implementation of the present invention. Users must register to create their profiles before they can login. A profile may include information comprising the user's age, gender, height, weight, body mass index, level of injury, completeness of injury, duration of injury, age at onset of SCI, whether he/she smokes, drinks alcohol, exercises, and/or has pressure ulcer history. In addition, the user needs to choose a user name and password. If a user can provide a valid user name and password, he/she can proceed to use the implemented smartphone application. The user has the options to update his/her profile, retrieve recommendations for wheelchair tilt & recline usage, and use the goniometer implemented in the smartphone to measure wheelchair tilt/recline angles.

Figure 3:
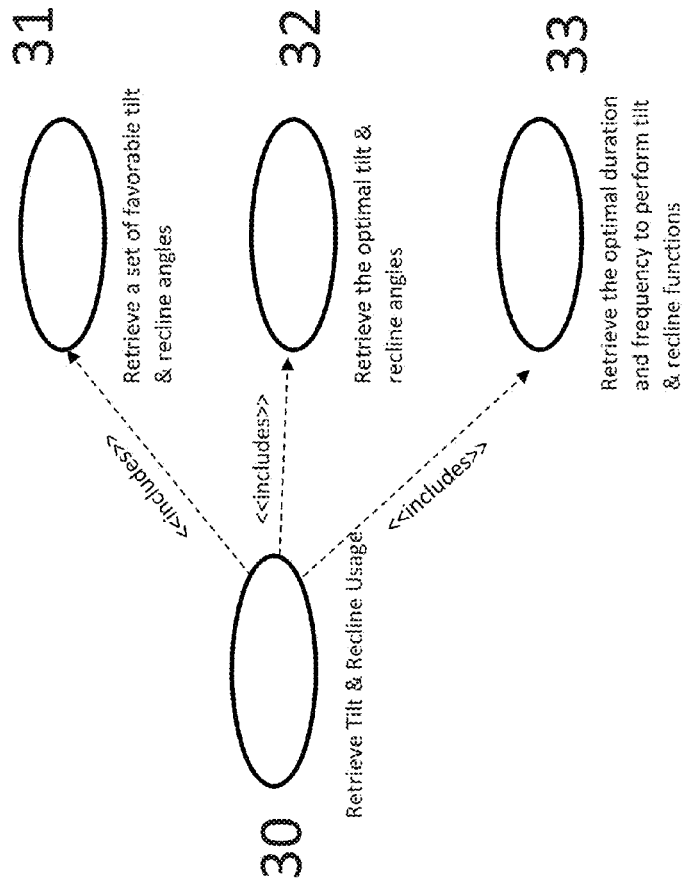
FIG. 3 is a non-limiting diagram presenting the function of "retrieve wheelchair tilt & recline usage". Specifically, users can obtain a set of favorable incline angles including tilt and recline combinations that can help reduce the risk of pressure ulcers.

FIG. 3 is a non-limiting diagram presenting the function of "retrieve wheelchair tilt & recline usage." Specifically, users can obtain a set of favorable incline angles including tilt and recline combinations that can help reduce the risk of pressure ulcers. An overall picture of a user's favorable tilt and recline settings are presentable, along with choices to adjust seating positions. Users are also presented with the best tilt and recline settings that can most effectively reduce risk of pressure ulcers. Users may select the option "retrieve optimal wheelchair tilt and recline setting". The option of retrieving the optimal duration and frequency to perform wheelchair tilt and recline may be selected. Users may retrieve information directed to how often (i.e., frequency) they should perform wheelchair tilt and recline functions and how long (i.e., duration) each time they should maintain at that tilt and recline setting.

Figure 4A:
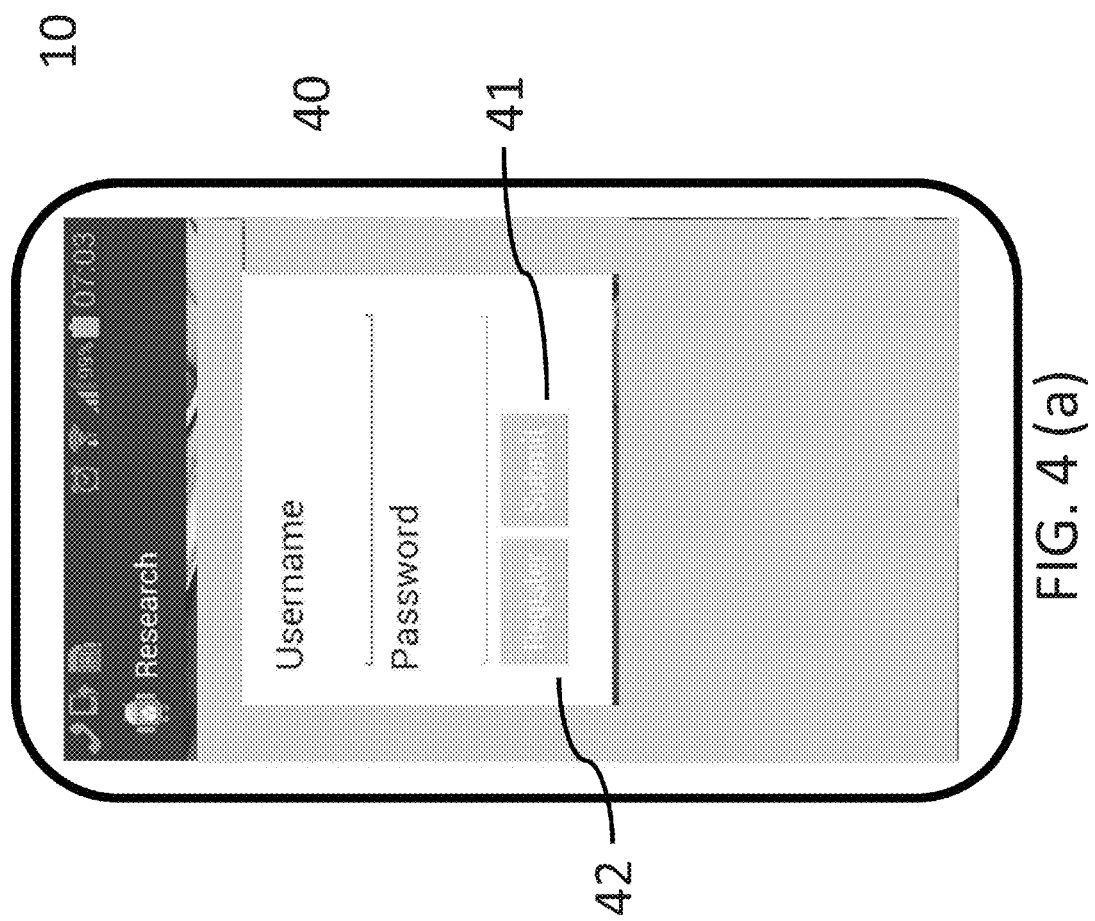
FIG. 4a is a non-limiting diagram showing a screen shot of a smartphone implementation.
Figure 4:
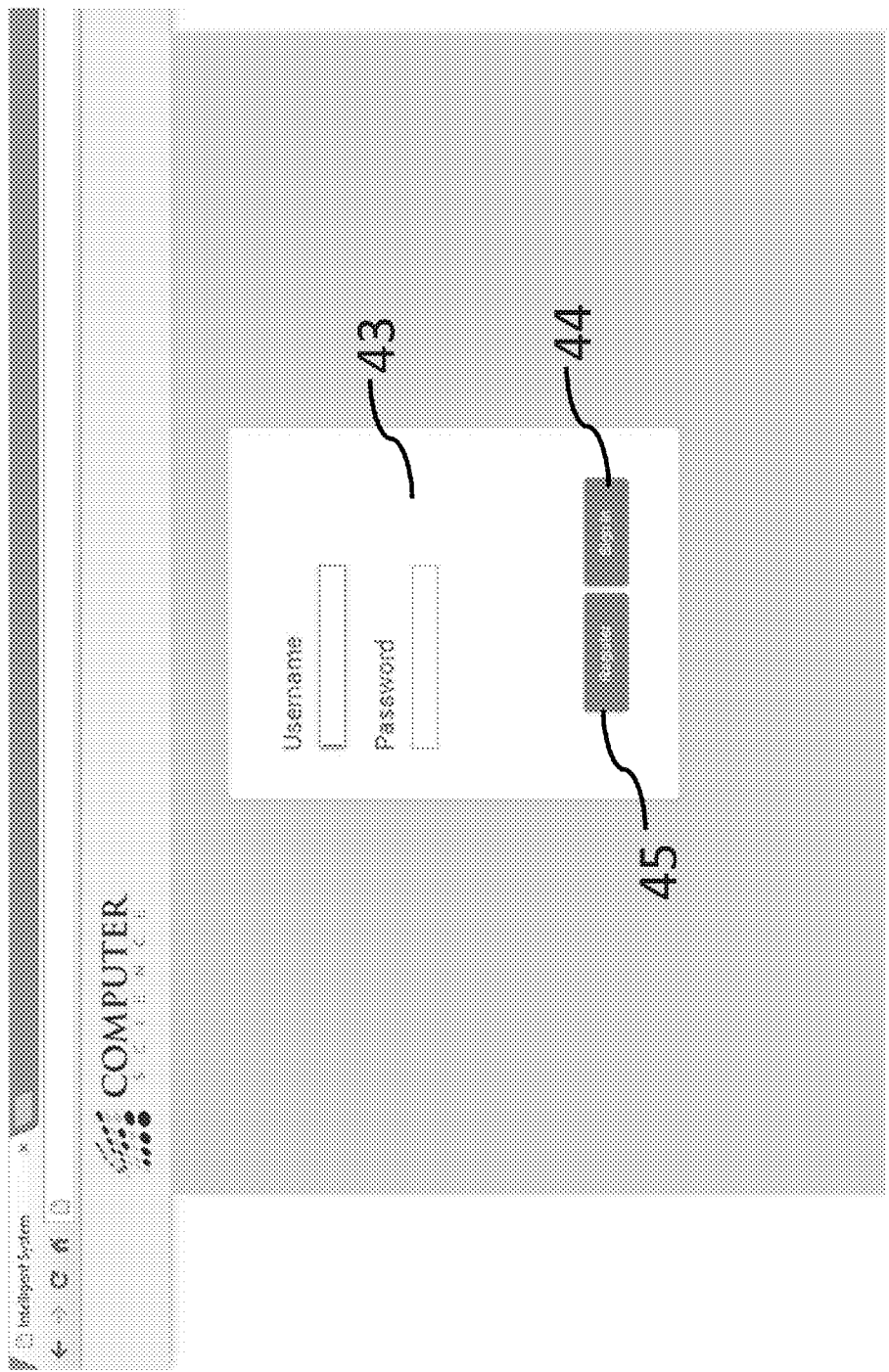
FIG. 4b is a non-limiting diagram showing a screen shot of a web-based implementation.
FIG. 4c is a non-limiting diagram showing the structure of a sample artificial neural network.

FIG. 4a is a non-limiting diagram showing a screen shot of a smartphone implementation for the mobile-to-cloud version. A user can choose "submit" if he/she is an existing user. Otherwise, the user needs to register first.

FIG. 4b is a non-limiting diagram showing a screen shot of a web-based implementation. A user can choose "submit" if he/she is an existing user. Otherwise, the user needs to register first.

Figure 4C:
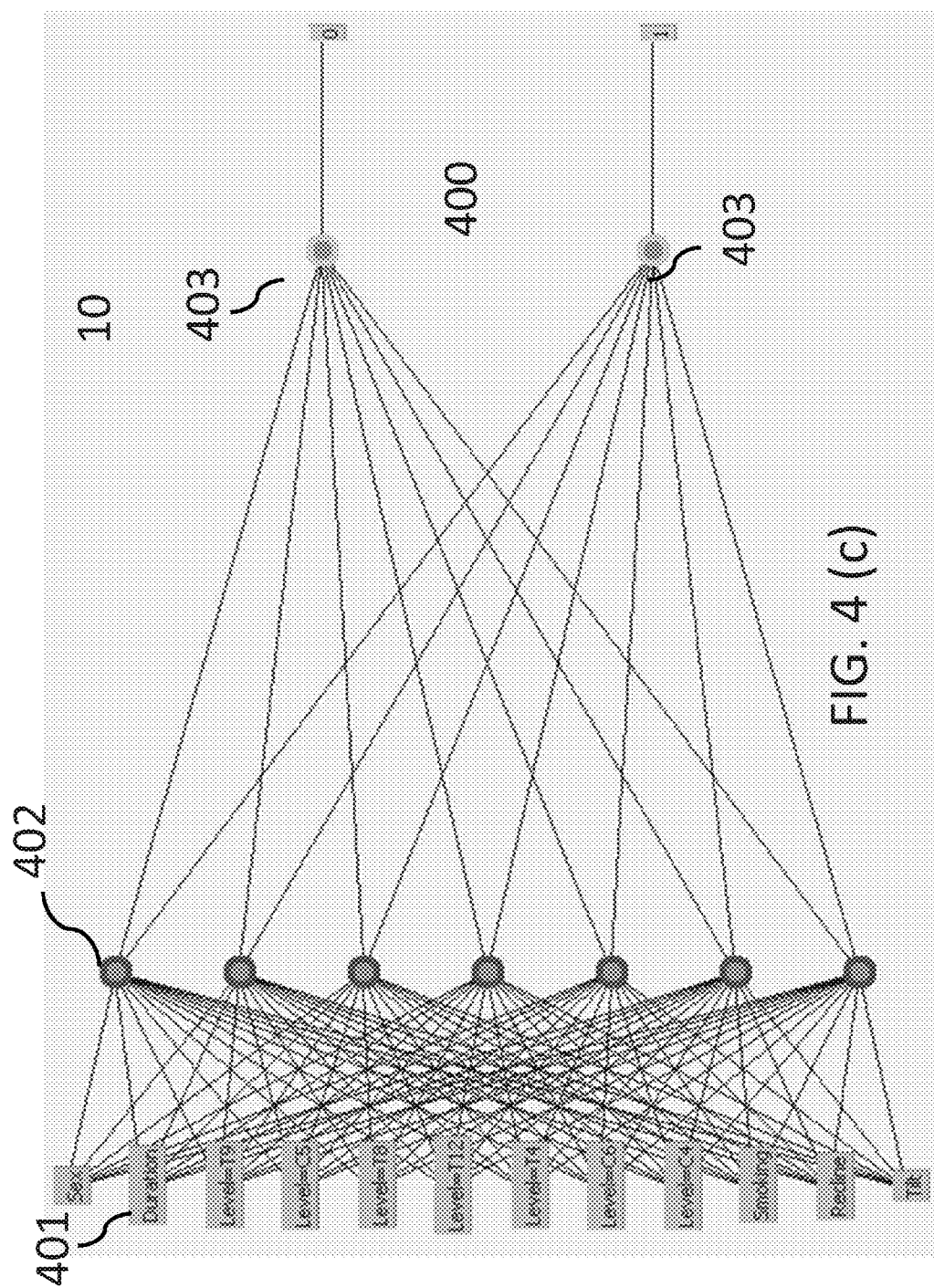

FIG. 4c is a non-limiting diagram showing the structure of an artificial neural network. It consists of three layers, which are input layer, hidden layer, and output layer arranged from left to right.

FIG. 5 is a non-limiting diagram showing top-level code structure for a smart device application (i.e., the local version). The code structure comprises the following modules: InitActivity, ClsTrainer, Main, InputData, ResultTask, FragmentForm, FragmentFrequency, FragmentAngleMeter, FragmentList, and FragmentResult.

Figure 6:
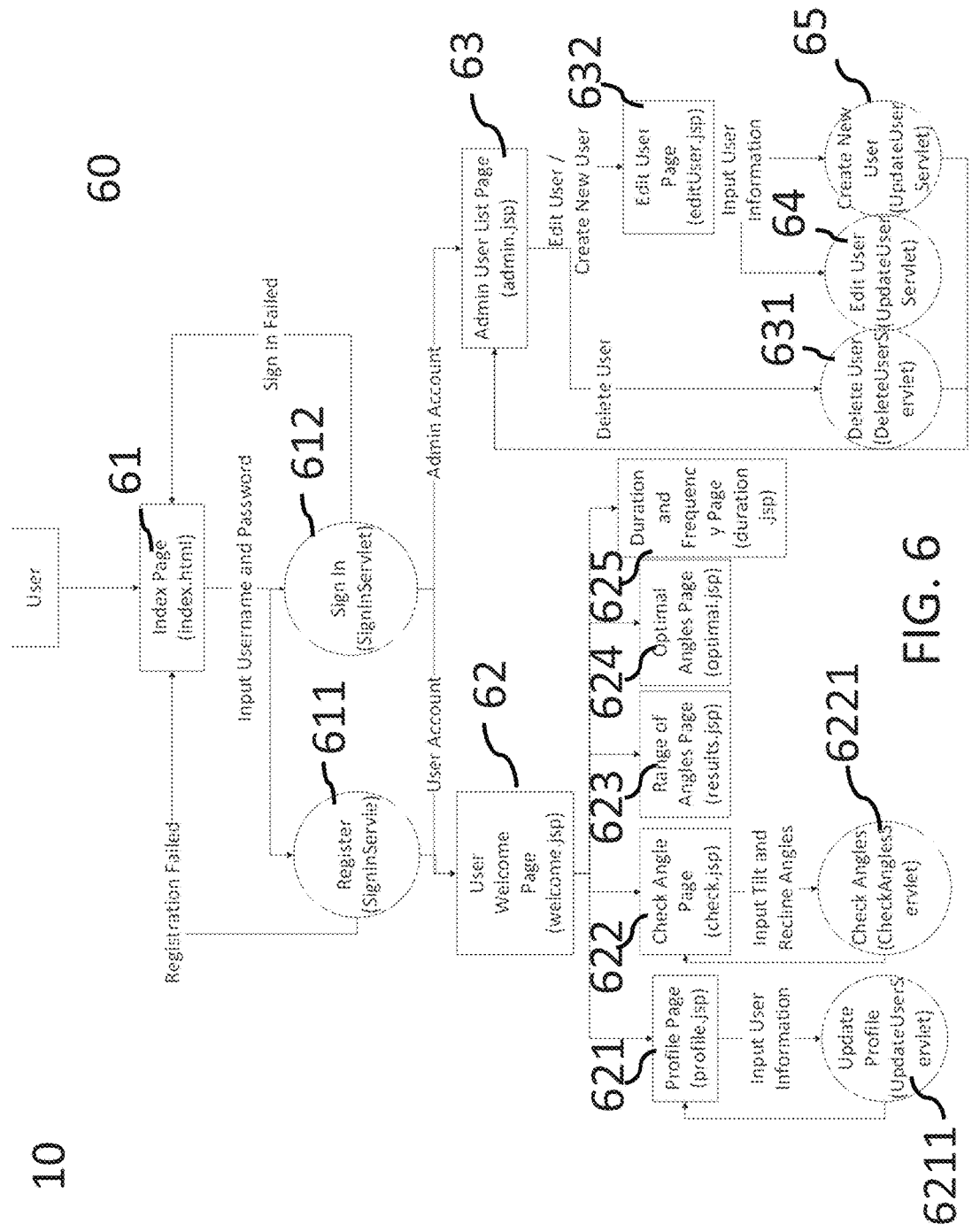
FIG. 6 is a non-limiting diagram showing top-level code structure for web-cloud configuration.

FIG. 6 is a non-limiting diagram showing top-level data flow for a web-based configuration. The code structure for the web-based configuration comprises the following modules: Index Page (index.html), Register (SignInServlet), Sign in (SignInServlet), User Welcome Page (welcome.jsp), Profile Page (profile.jsp), Update Profile (UpdateUserServlet), Check Angle Page (check.jsp), Check Angles (CheckAnglesServlet), Range of Angles Page (result.jsp), Optimal Angle Page (optimal.jsp), Duration and Frequency Page (duration.jsp), Admin User List Page (admin.jsp), Delete User (DeleteUserServlet), Edit User Page (edituser.jsp), Edit User (UpdateUserServlet), and Create New User (UpdateUserServlet).

Figure 7:
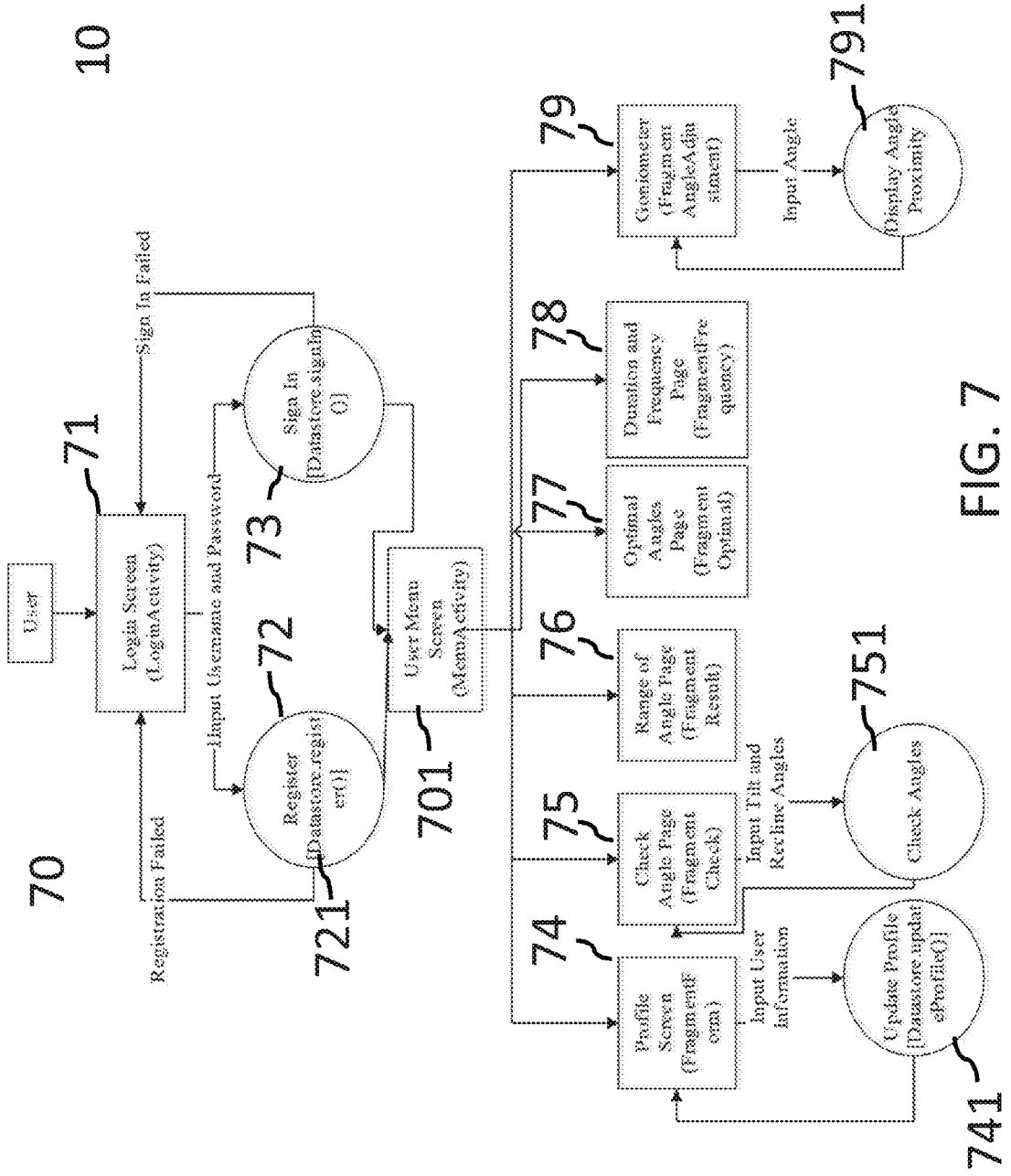
FIG. 7 is a non-limiting diagram showing top-level code structure for mobile-to-cloud configuration using the Android operating system.

FIG. 7 is a non-limiting diagram showing top-level code structure for mobile-to-cloud configuration using the Android operating system. The code structure includes Register, Sign In, Main Menu Screen (MenuActivity), Profile Screen (FragmentForm), Check Angle Page (FragmentCheck), Range of Angles Page (FragmentResult), Optimal Angles Page (FragmentOptimal), Duration and Frequency Page (FragmentFrequency), and Goniometer (FragmentAngleAdjustment).

Figure 8:
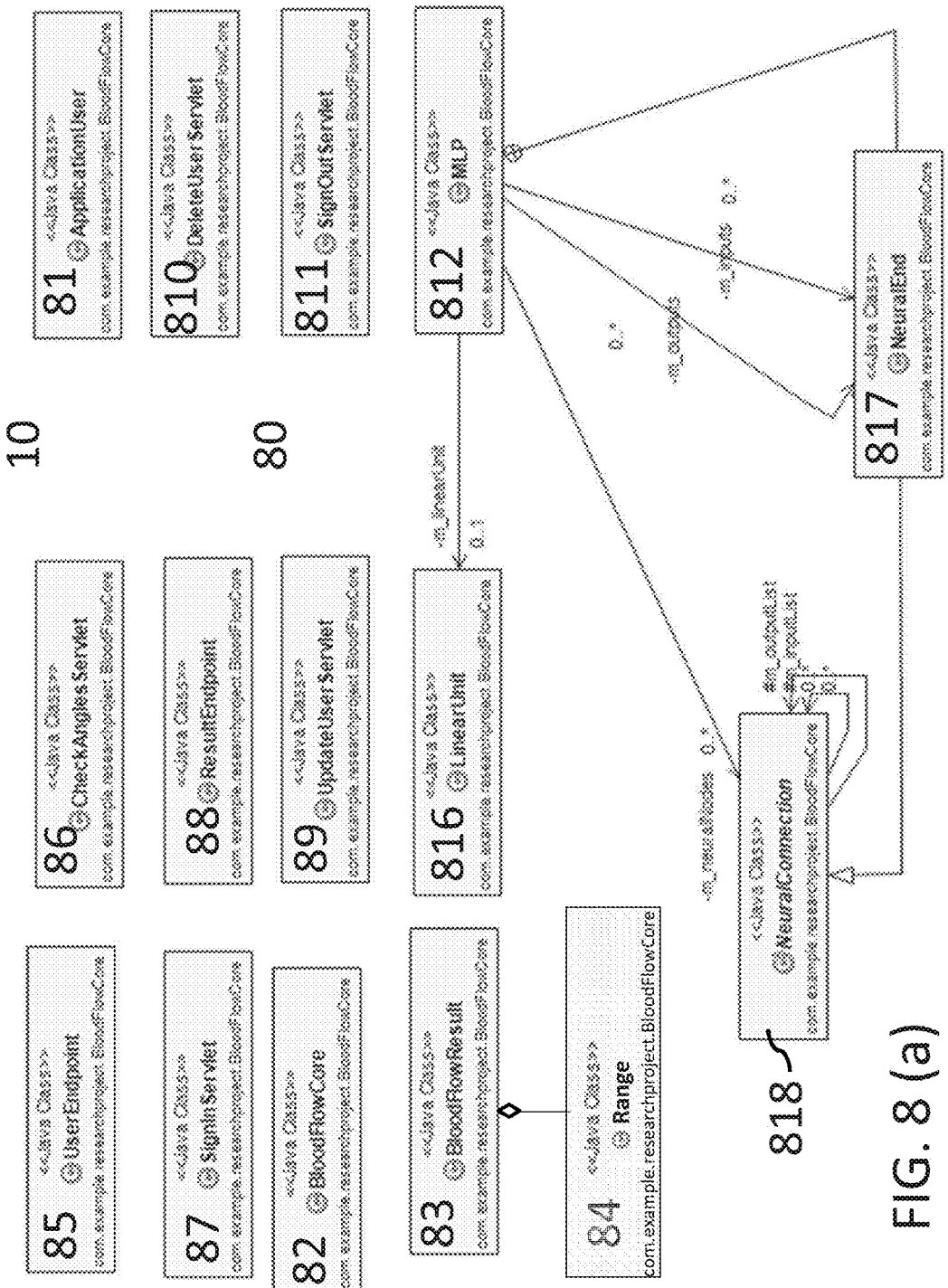
FIG. 8(a) is a non-limiting diagram showing a class diagram for the Google App Engine (GAE, i.e., cloud) configuration where the classes are used to compute personalized guidance on wheelchair tilt and recline usage, and interact with the mobile and web applications.
FIG. 8(b) is a non-limiting diagram showing a class diagram for Google App Engine (cloud) configuration of the present invention where the classes are used to store the tilt and recline usage information (the time when the user performs the tilt and recline functions, the angles of the tilt and recline, etc.)

FIG. 8(a) is a non-limiting diagram showing a class diagram for a GAE (cloud) configuration where the classes are used to compute personalized guidance on wheelchair tilt and recline usage, and interact with the mobile and web applications. The code structure includes: ApplicationUser, BloodFlowCore, BloodFlowResult, Range, UserEndpoint, CheckAnglesServlet, SignInServlet, ResultEndpoint, UpdateUserServlet, DeleteUserServlet, SignOutServlet, MLP, LinearUnit, NeuralEnd, and NeuralConnection.

Figure 8B:
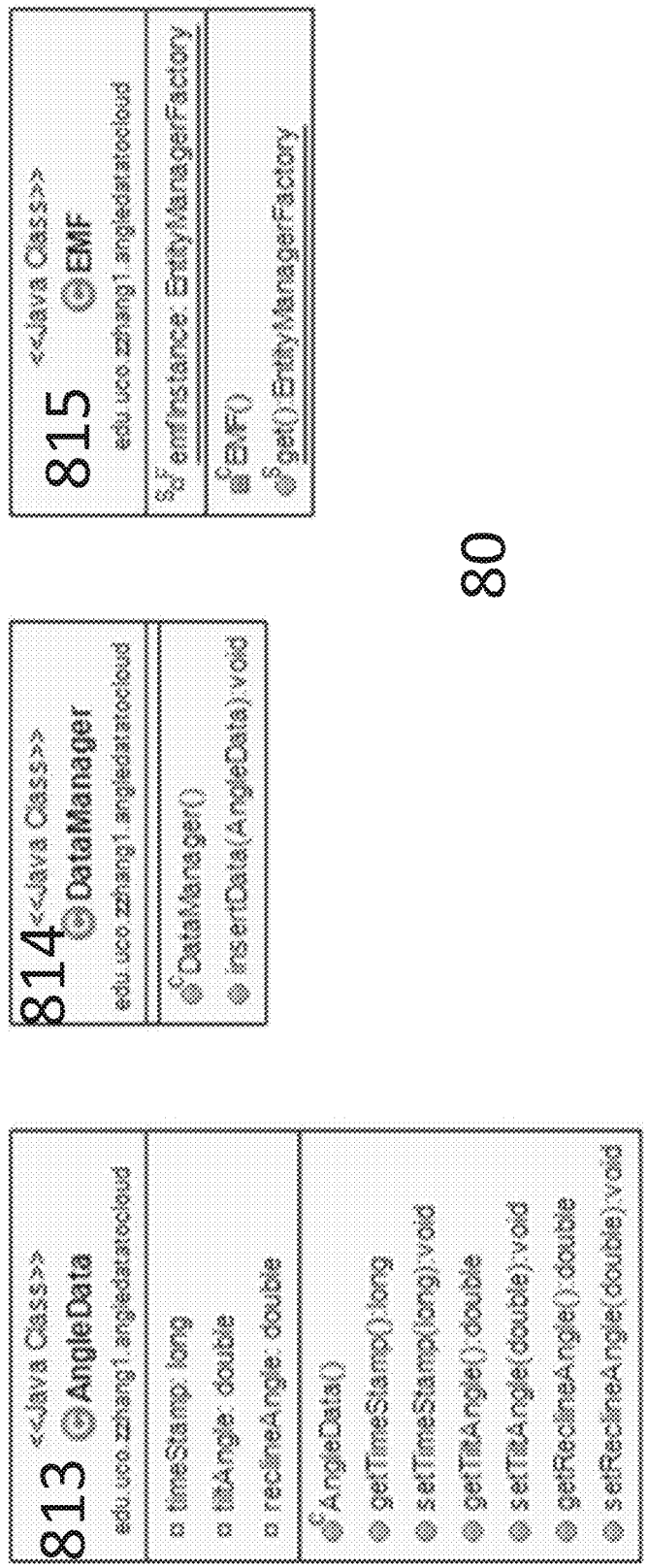

FIG. 8(b) is a non-limiting diagram showing a class diagram for the GAE (cloud) configuration of the present invention where the classes are used to store the tilt and recline usage information (the time when the user performs the tilt and recline functions, the angles of the tilt and recline, etc.) The code structure includes: AngleData, DataManager, and EMF.

Figure 9:
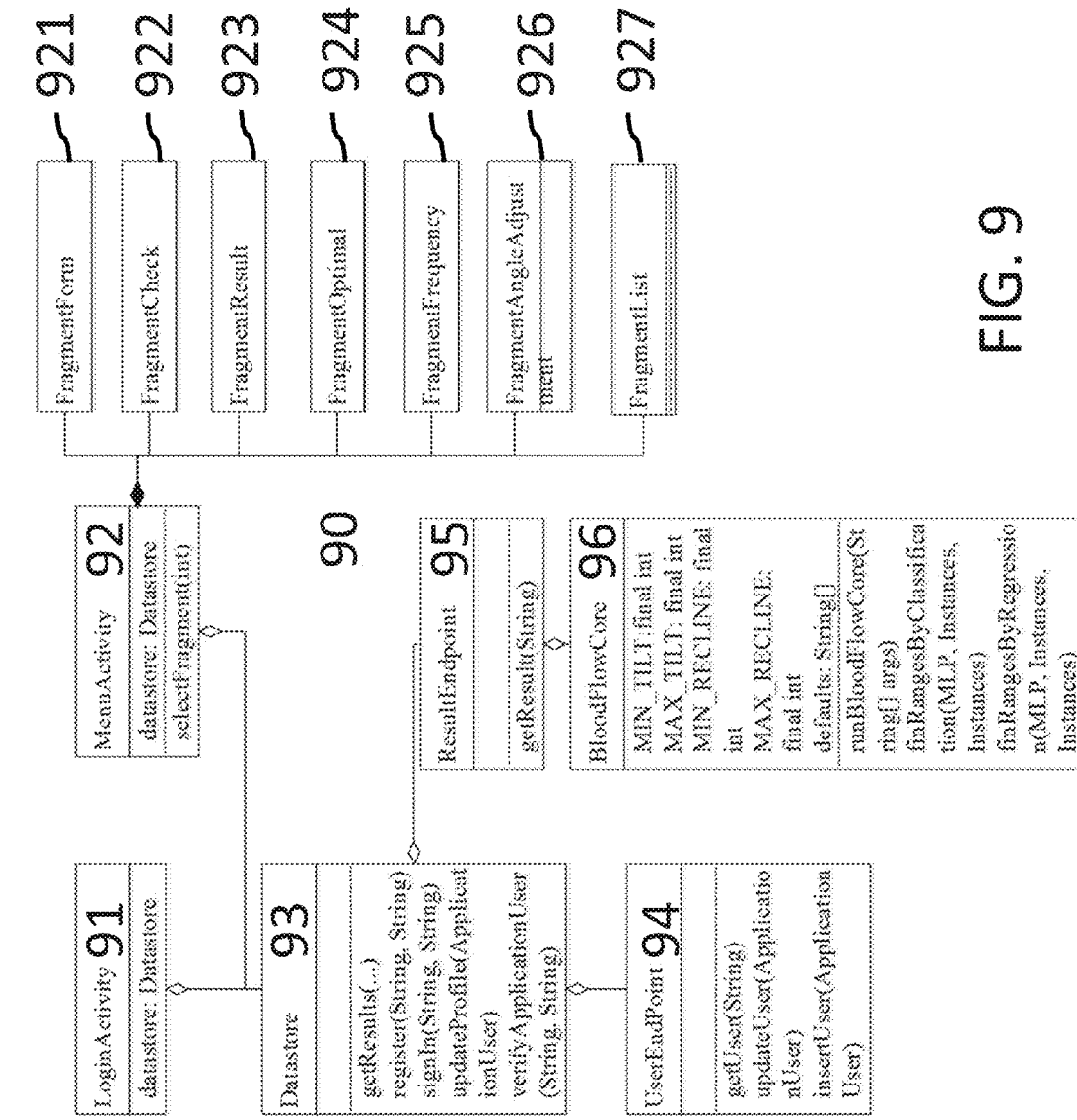
FIG. 9 is a non-limiting diagram showing a class diagram for a mobile configuration using the Android operating system (complementing FIG. 7).

FIG. 9 is a non-limiting diagram showing a class diagram for a mobile configuration using the Android operating system (complementing FIG. 7). The code structure includes: LoginActivity, MenuActivity, FragmentForm, FragmentCheck, FragmentResult, FragmentOptimal, FragmentFrequency, FragmentAngleAdjustment, FragmentAngleMeter, Datastore, UserEndpoint, ResultEndpoint, BloodFlowCore, LoginActivity, MenuActivity, FragmentForm, FragmentCheck, FragmentResult, FragmentOptimal, FragmentFrequency, Datastore, UserEndpoint, ResultEndpoint, and BloodFlowCore.

Figure 10A:
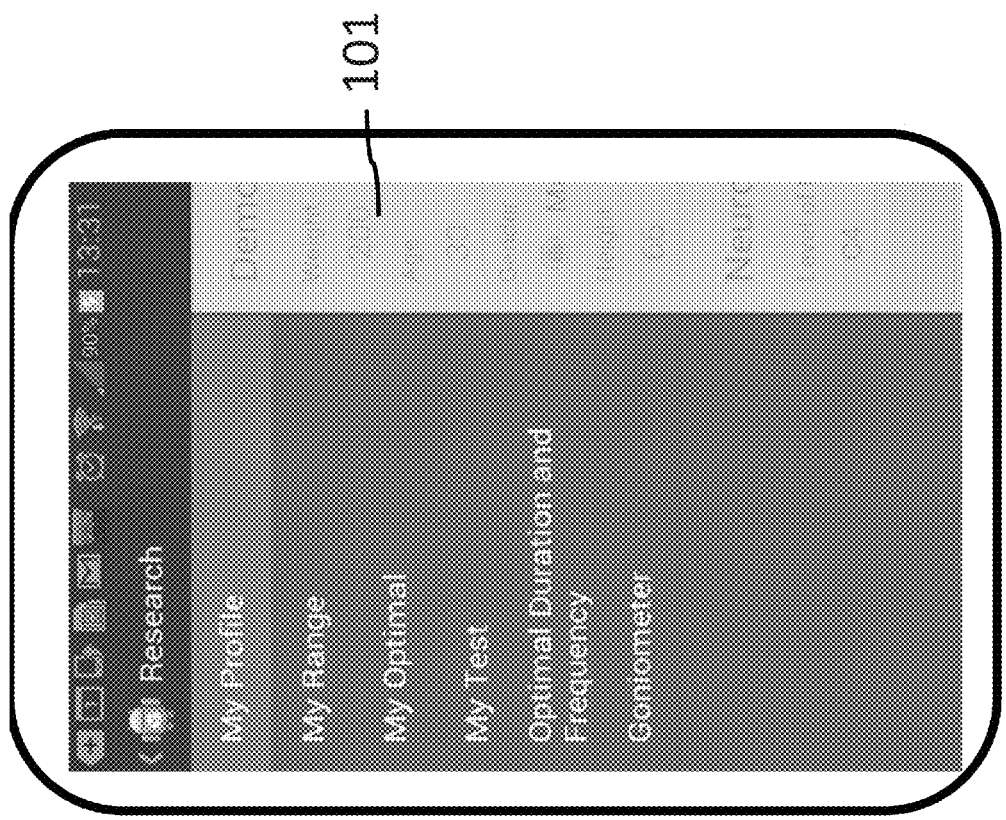
FIG. 10a is a non-limiting diagram showing a screen shot of a smartphone implementation providing a user interface to access system functions.

FIG. 10a is a non-limiting diagram showing a screen shot of a smartphone implementation providing a user interface to access system functions. System responses are anticipated to at least user touch and voice commands. Audio recitation and response for visually impaired individuals is anticipated.

Figure 10B:
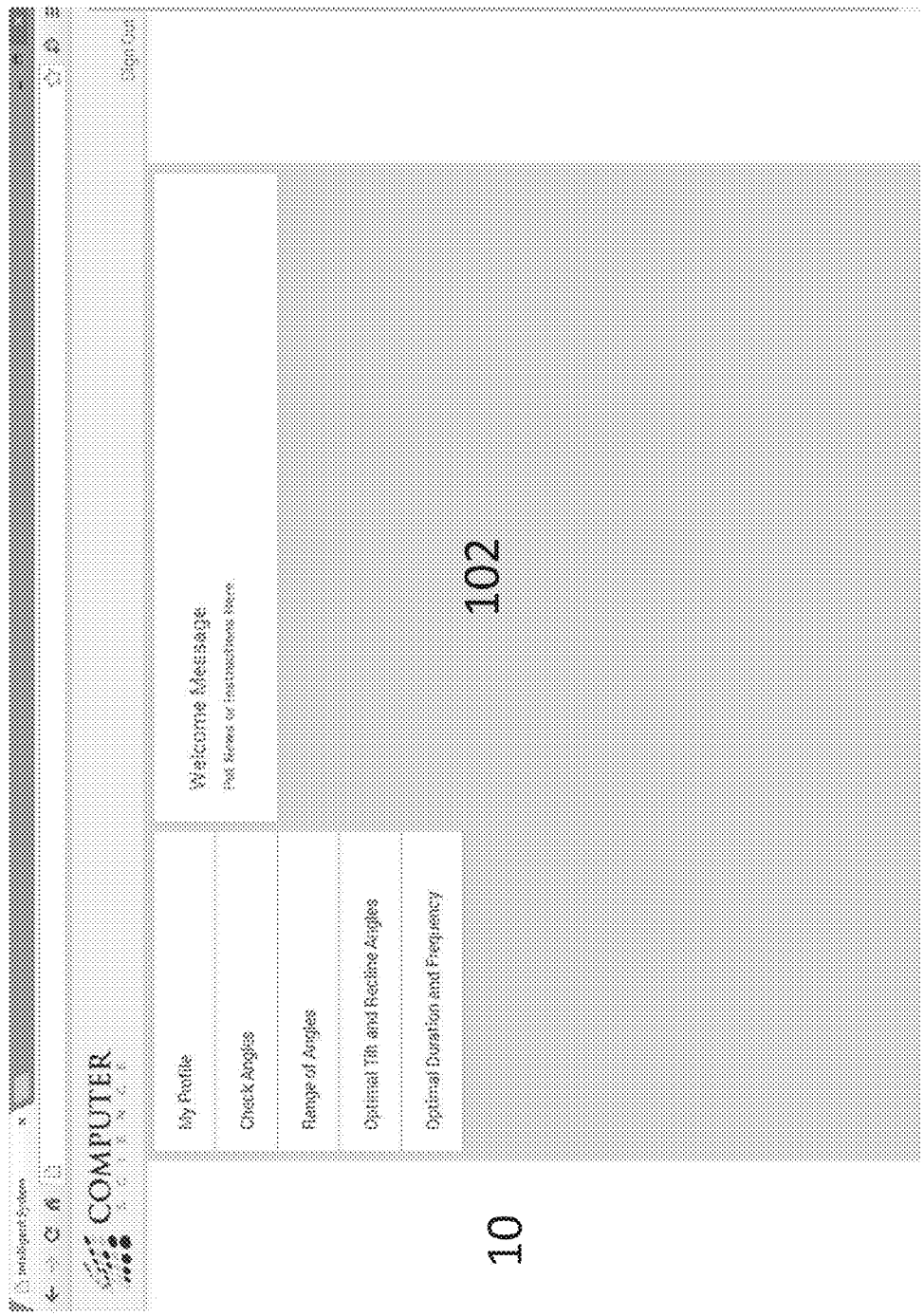
FIG. 10b is a non-limiting diagram showing a screen shot of a web-based implementation providing a user interface to access system functions.

FIG. 10b is a non-limiting diagram showing a screen shot of a web-based implementation providing a user interface to access system functions. System responses are anticipated to at least user touch and voice commands. Audio recitation and response for visually impaired individuals is anticipated.

Figure 11A:
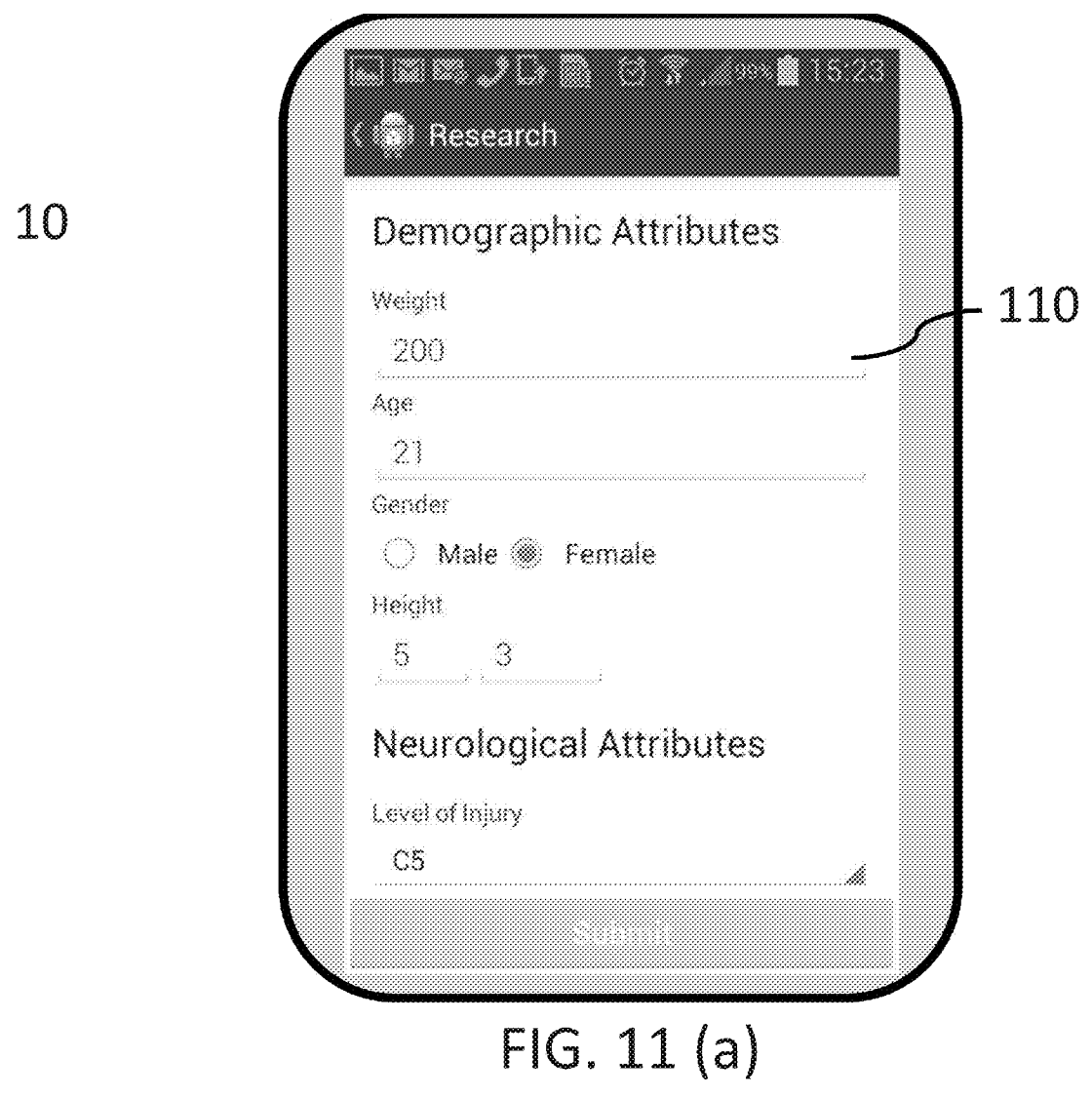

FIG. 11a is a non-limiting diagram showing a screen shot of a smartphone implementation providing a user interface to enter demographic attributes. System responses are anticipated to at least user touch and voice commands. Audio recitation and response for visually impaired individuals is anticipated.

Figure 11B:
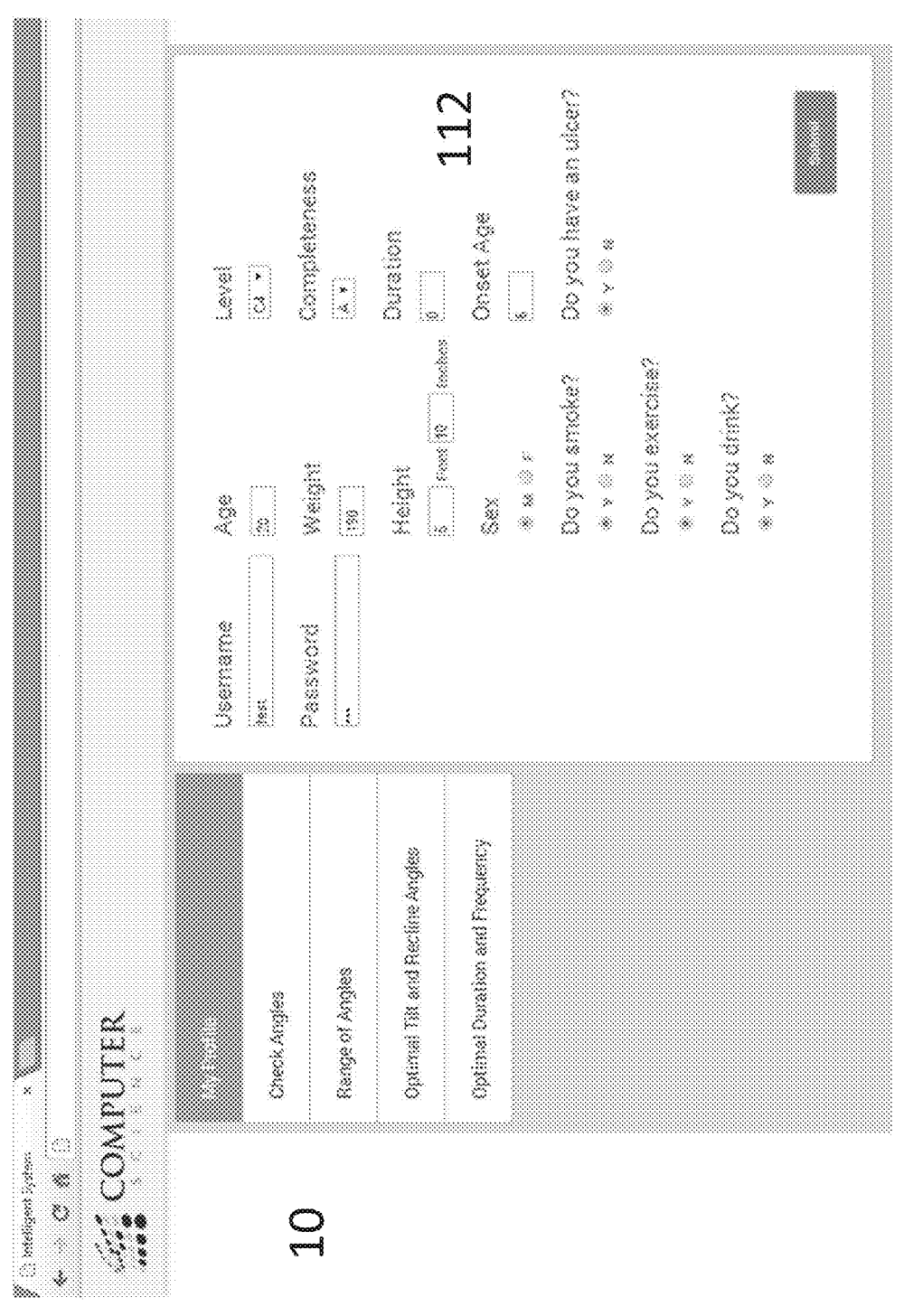

FIG. 11b is a non-limiting diagram showing a screen shot of a web-based implementation providing a user interface to enter demographic attributes. System responses are anticipated to at least user touch and voice commands. Audio recitation and response for visually impaired individuals is anticipated.

Figure 12A:
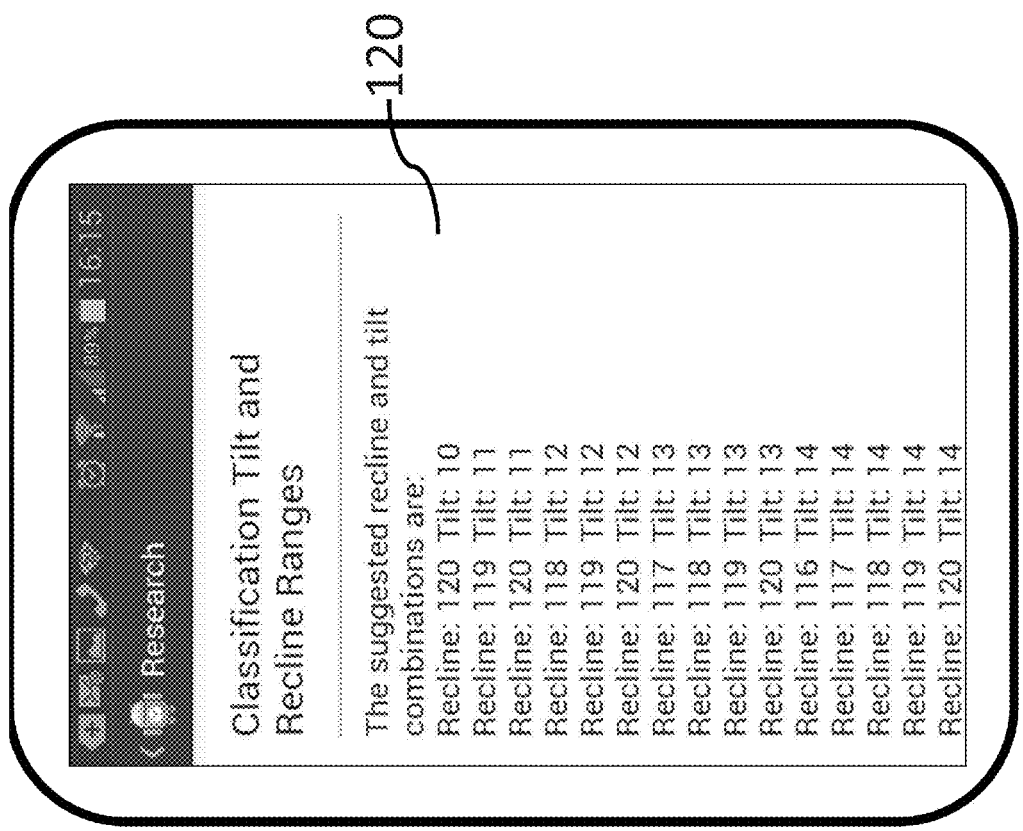
FIG. 12a is a non-limiting diagram showing a screen shot of a smartphone implementation providing a user interface to display favorable tilt and recline angles.
Figure 12:
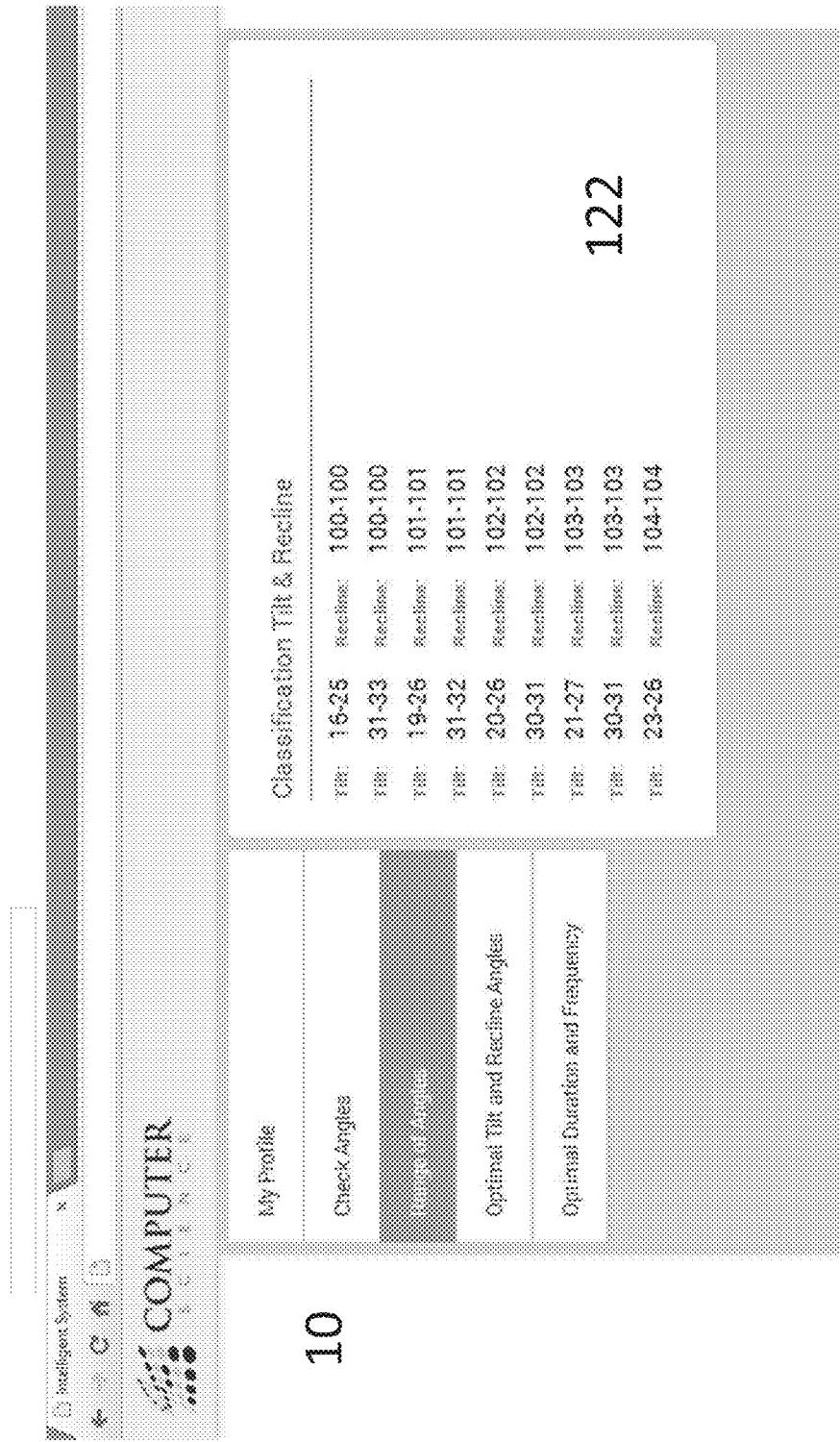
FIG. 12b is a non-limiting diagram showing a screen shot of a web-based implementation providing a user interface to display favorable tilt and recline angles.
FIG. 12c is a non-limiting diagram showing a screen shot of a smartphone implementation providing a user interface to display the best tilt and recline angles for the user.
FIG. 12d is a non-limiting diagram showing a screen shot of a web-based implementation of the present invention providing a user interface to display the best tilt and recline angle for the user.
Figure 12:
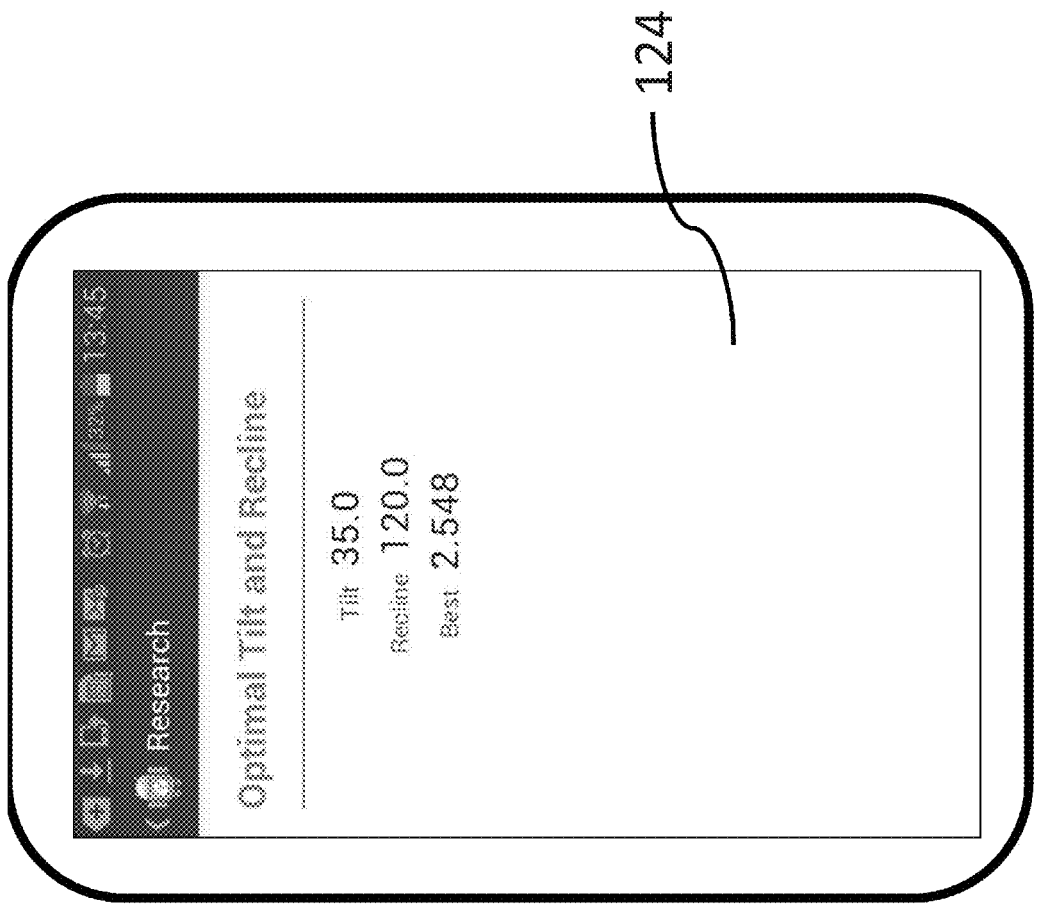
Figure 12:
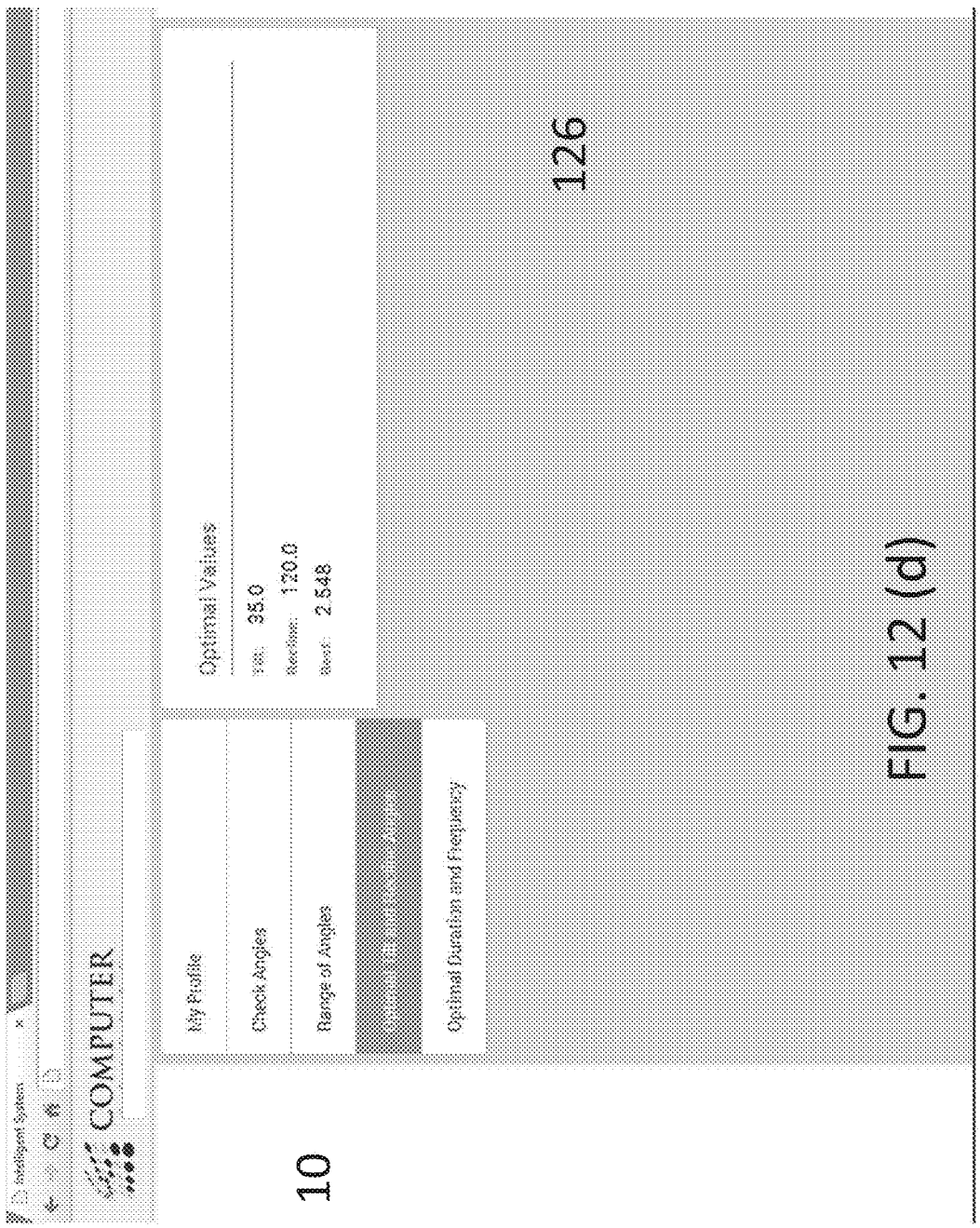

FIG. 12a is a non-limiting diagram showing a screen shot of a smartphone implementation providing a user interface to display favorable tilt and recline angles. System responses are anticipated to at least user touch and voice commands. Audio recitation and response for visually impaired individuals is anticipated.

FIG. 12b is a non-limiting diagram showing a screen shot of a web-based implementation providing a user interface to display favorable tilt and recline angles. System responses are anticipated to at least user touch and voice commands. Audio recitation and response for visually impaired individuals is anticipated.

FIG. 12c is a non-limiting diagram showing a screen shot of a smartphone implementation providing a user interface to display the best tilt and recline angle for a user. System responses are anticipated to at least user touch and voice commands. Audio recitation and response for visually impaired individuals is anticipated.

FIG. 12d is a non-limiting diagram showing a screen shot of a web-based implementation providing a user interface to display the best tilt and recline angle for a user. System responses are anticipated to at least user touch and voice commands. Audio recitation and response for visually impaired individuals is anticipated.

Figure 13:
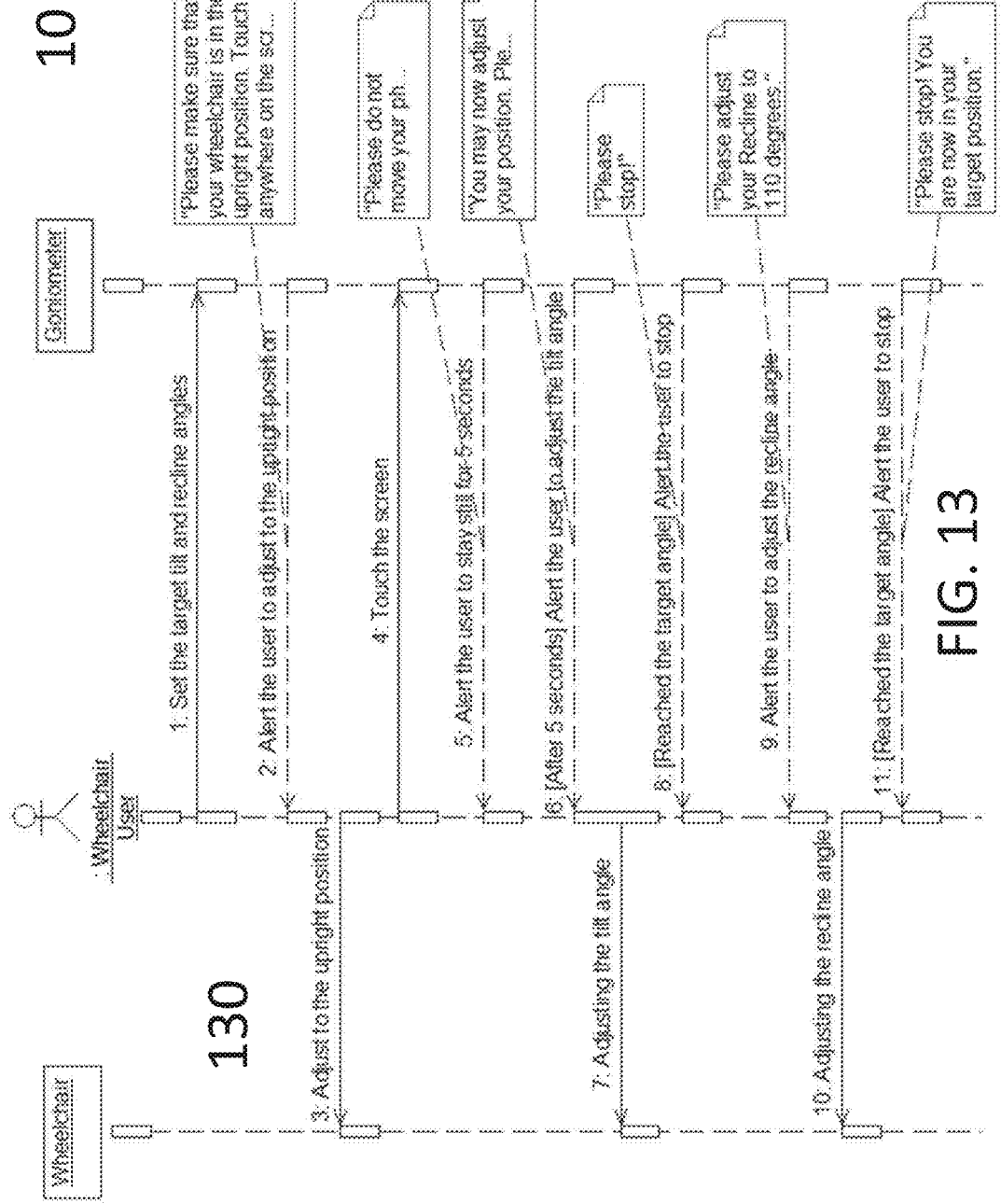
FIG. 13 is a non-limiting sequence diagram showing the process for determining proper adjustment of tilt and recline settings as determined by the present invention, and aided by actionable aural guidance provided by the present invention.

FIG. 13 is a non-limiting diagram showing the process for determining proper adjustment of tilt and recline settings as determined by the present invention. Measurement, display, and auditory notification of tilt and recline angles are accomplished in substantially real-time as a user adjusts tilt and recline settings on a wheelchair. Actionable aural guidance is provided to enable the user to achieve recommended tilt and recline settings suitable to the particular wheelchair user based on his or her specific profile.

Figure 14:
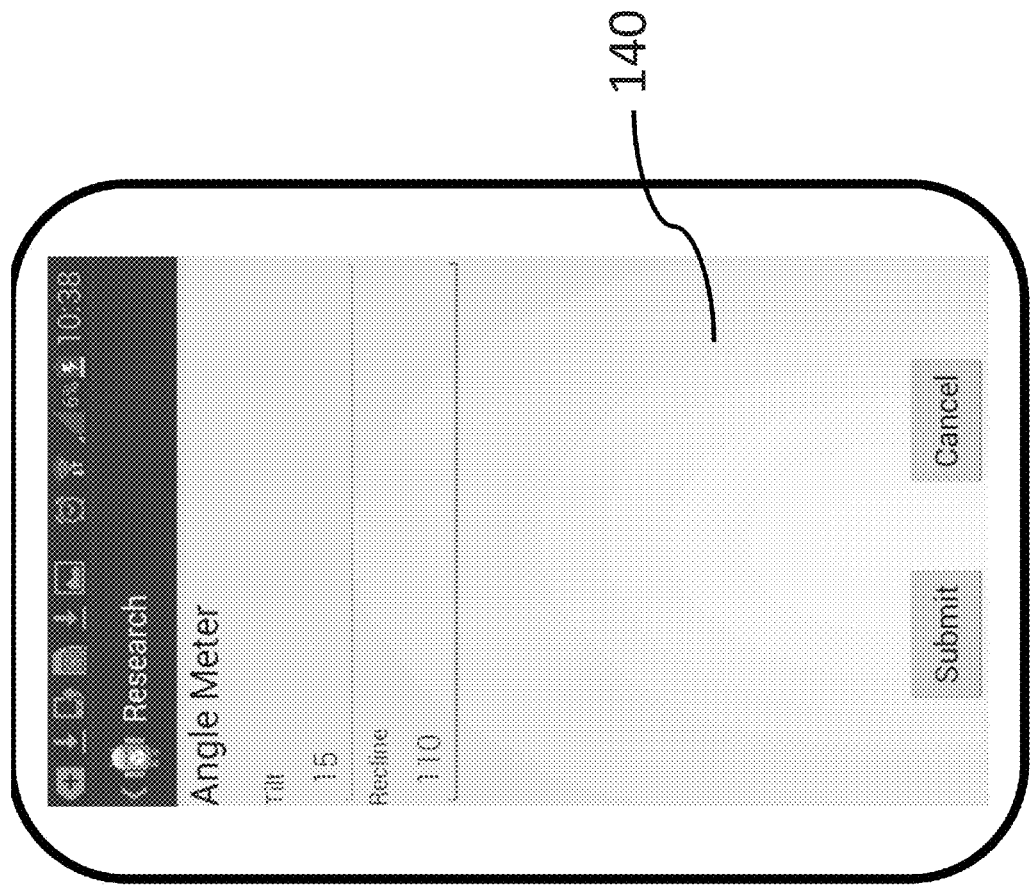
FIG. 14 is a non-limiting diagram showing an exemplary screenshot for "1: Set the target tilt and recline angles (e.g., 15 tilt/110 recline)" as the first step depicted in FIG. 13.

FIG. 14 is a non-limiting diagram showing an exemplary screenshot of the user interface implemented as an element in the process for determining proper adjustment of tilt and recline settings as determined by the present invention. A screenshot for "1: Set the target tilt and recline angles (e.g., 15 tilt/110 recline)" is shown as the first step depicted in FIG. 13.

Figure 15:
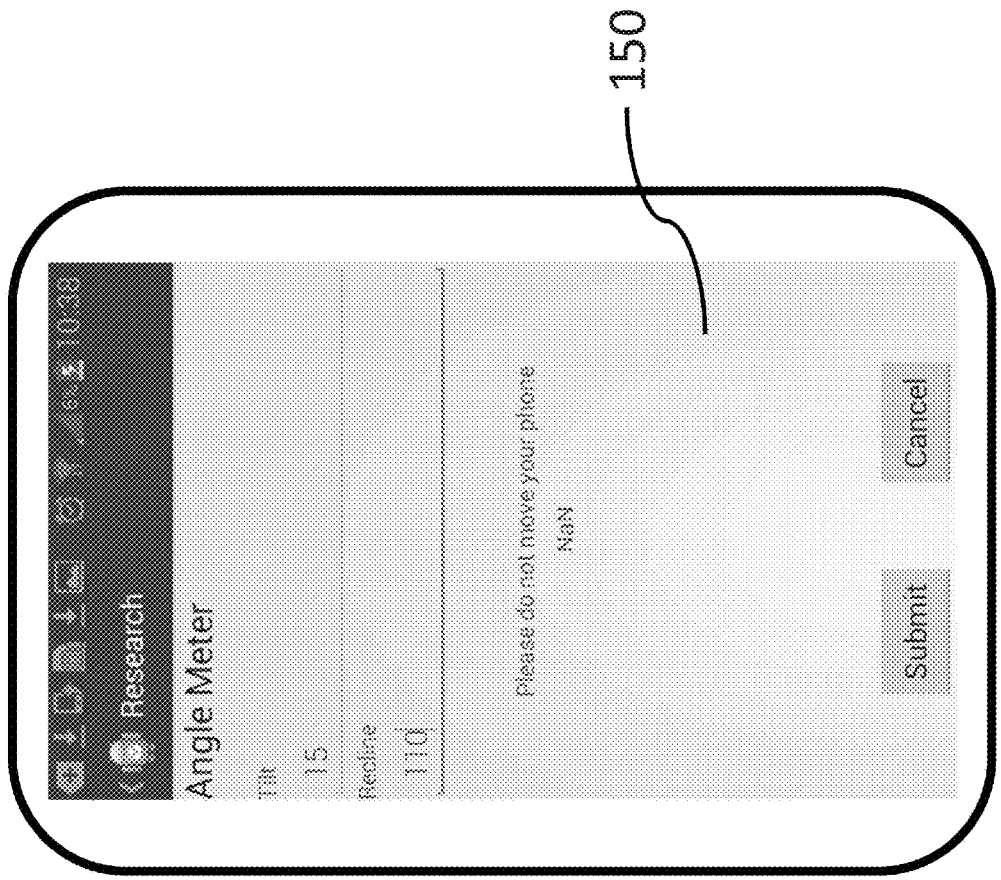
FIG. 15 is a non-limiting diagram showing an exemplary screenshot for "5: Alert the user to stay still for 5 seconds" as the fifth step depicted in FIG. 13.

FIG. 15 is a non-limiting diagram showing an exemplary screenshot of the user interface implemented as an element in the process for determining proper adjustment of tilt and recline settings as determined by the present invention. Actionable aural guidance is provided to ask the user to stay still for a period of time (e.g., 5 seconds) so that the smart device application can accurately measure the initial upright position. An exemplary screenshot for "5: Alert the user to stay still for 5 seconds" is shown as the fifth step depicted in FIG. 13.

Figure 16:
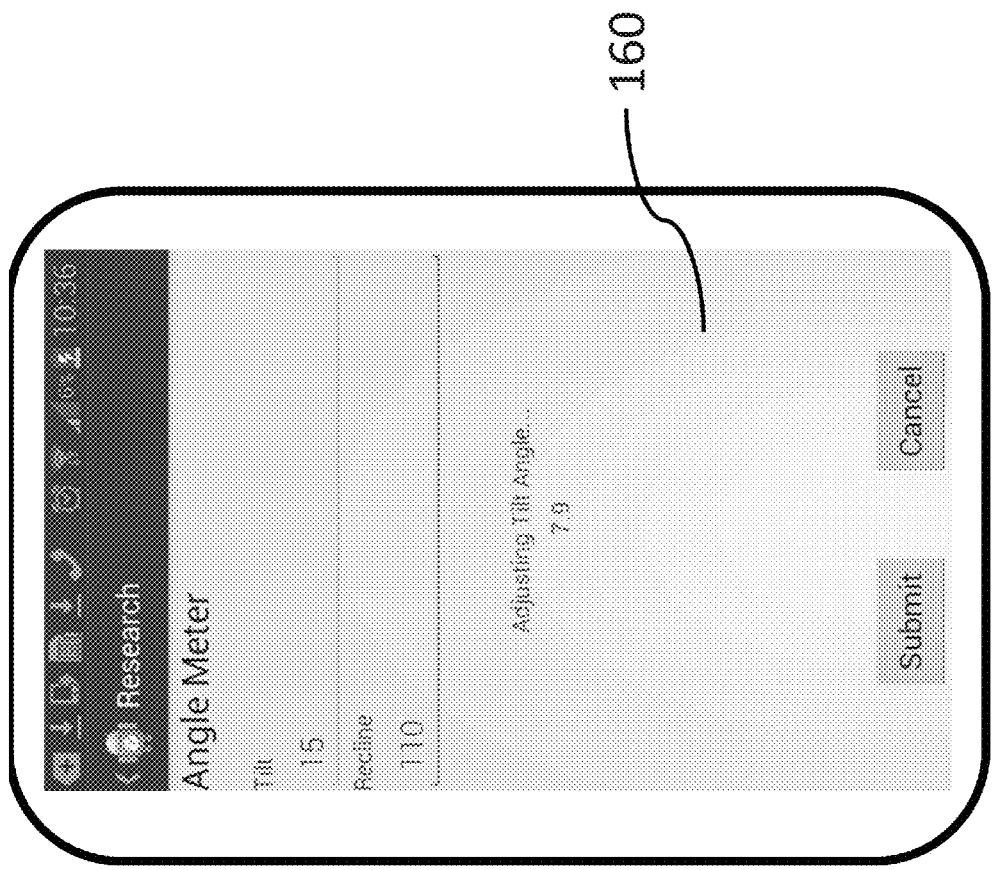
FIG. 16 is a non-limiting diagram showing an exemplary screenshot of the display on the user interface while the user adjusts the tilt angle as the seventh step depicted in FIG. 13.

FIG. 16 is a non-limiting diagram showing an exemplary screenshot of the user interface implemented as an element in the process for determining proper adjustment of tilt and recline settings as determined by the present invention. A screenshot of the display on the user interface while the user adjusts the tilt angle is shown as the seventh step depicted in FIG. 13.

Figure 17:
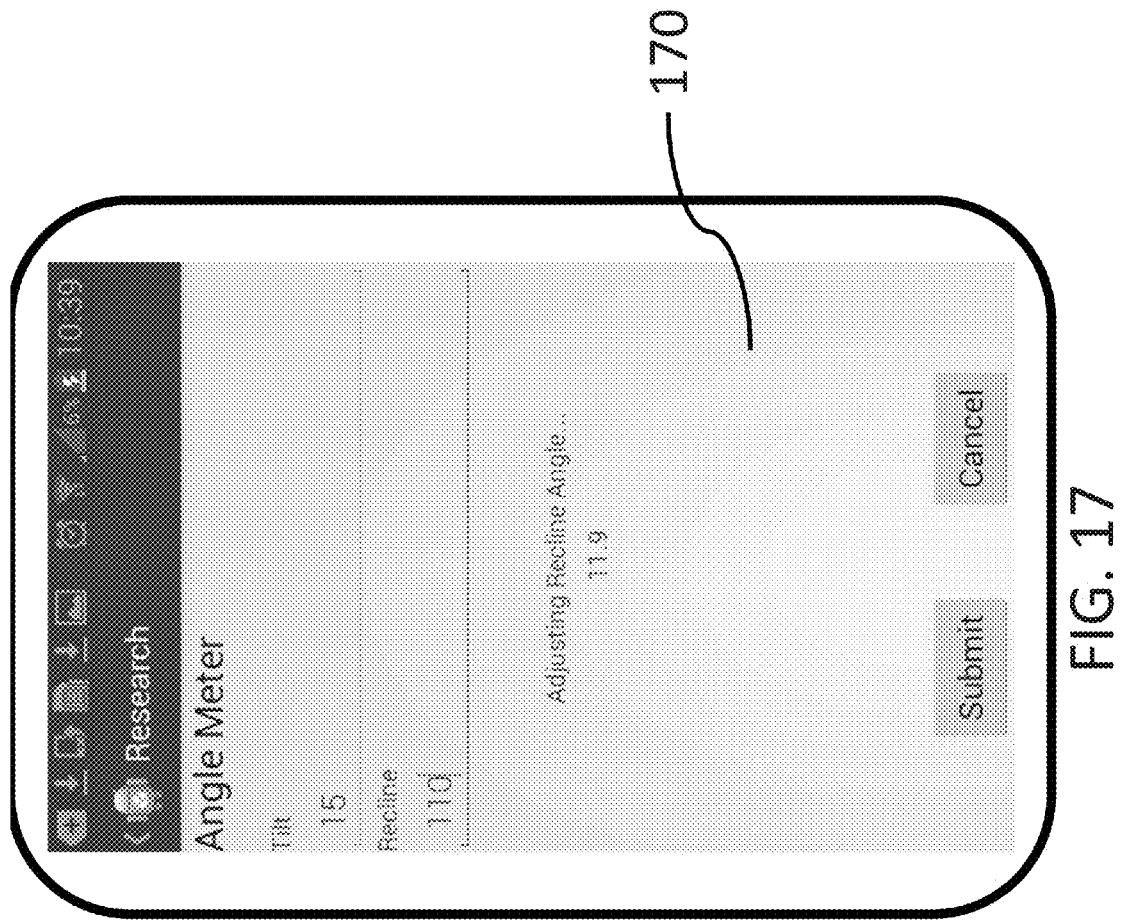
FIG. 17 is a non-limiting diagram showing an exemplary screenshot of the display on the user interface while the user adjusts the recline angle as the tenth step depicted in FIG. 13.

FIG. 17 is a non-limiting diagram showing an exemplary screenshot of the user interface implemented as an element in the process for determining proper adjustment of tilt and recline settings as determined by the present invention. A screenshot of the display on the user interface while the user adjusts the recline angle, is shown as the tenth step depicted in FIG. 13.

Figure 18:
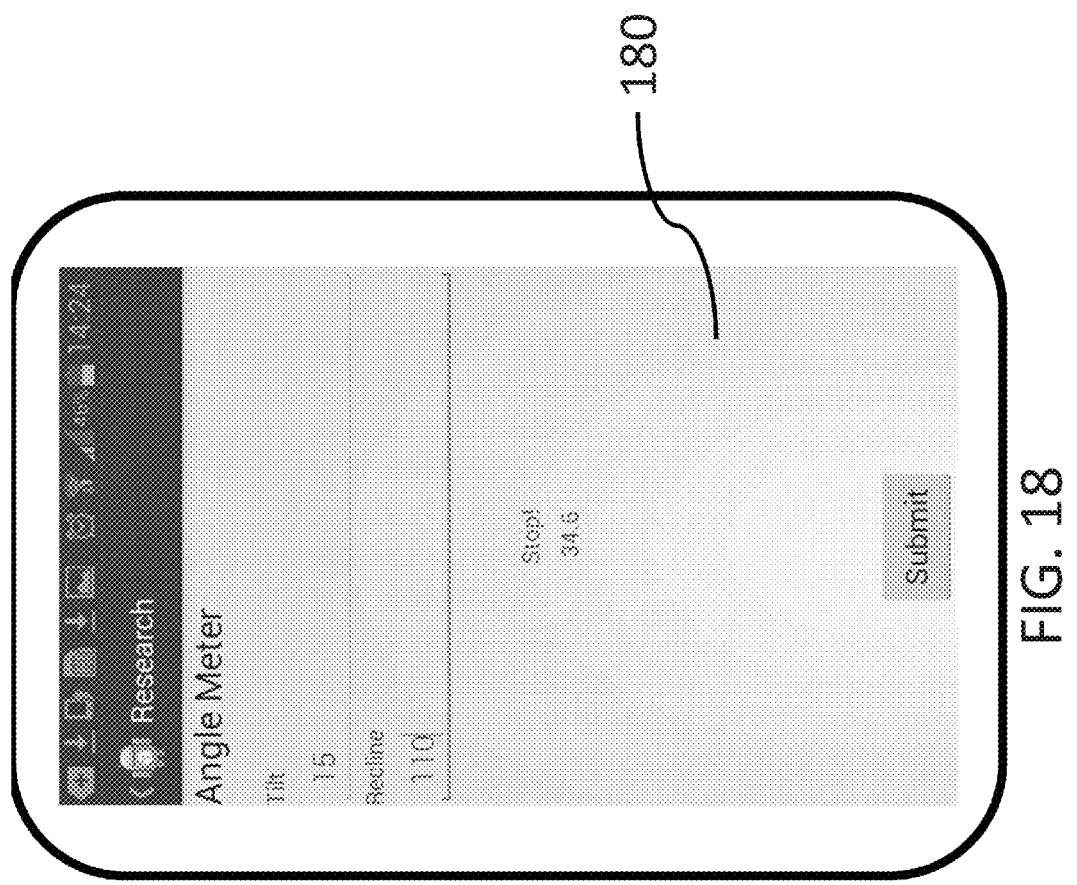
FIG. 18 is a non-limiting diagram showing an exemplary screenshot of the display on the user interface while the smartphone application uses voice alerts to tell the user that the target recline angle has been reached as the eleventh step depicted in FIG. 13.

FIG. 18 is a non-limiting diagram showing an exemplary screenshot of the user interface implemented as an element in the process for determining proper adjustment of tilt and recline settings as determined by the present invention. A screenshot of the display on the user interface is shown as the eleventh step depicted in FIG. 13. Actionable aural guidance may be provided concomitantly to tell the user that the target recline angle has been reached.

Figure 19:
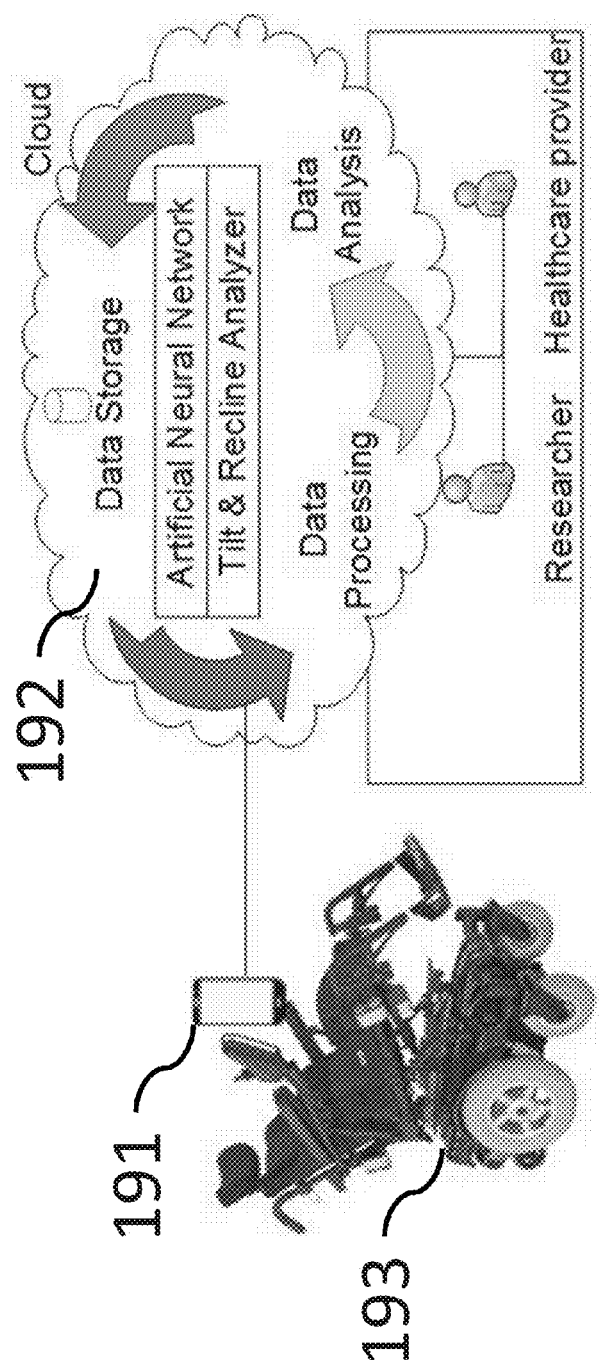
FIG. 19 is a non-limiting diagram showing the top level architecture of the mobile-cloud implementation of the present invention operable in an embodiment directed to wheelchair usage.

FIG. 19 is a non-limiting diagram showing the top level architecture of the mobile-cloud implementation of the present invention in an embodiment directed to wheelchair use. An artificial neural network is shown implemented in the cloud, along with data processing and analysis. Researchers and healthcare providers are able to remotely access patient data through a secure and controlled interface.

Figure 20:
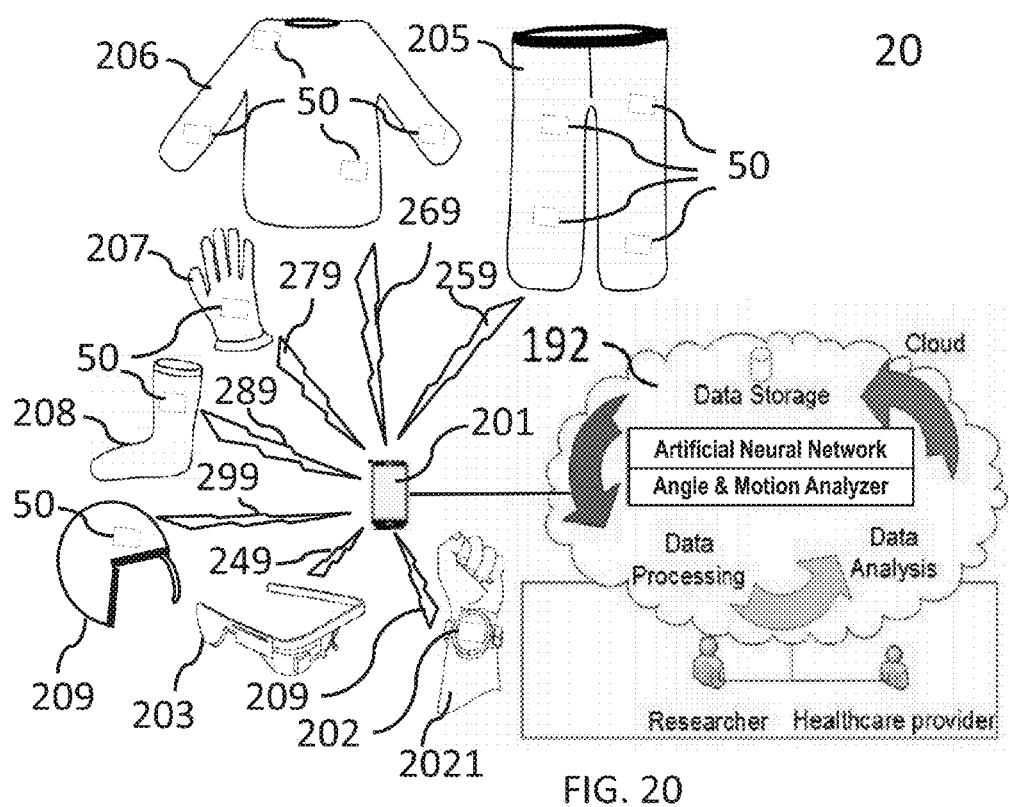
FIG. 20 is a non-limiting diagram showing the top level architecture of the mobile-cloud implementation of the present invention operable in an embodiment directed to physical conditioning, activity monitoring, and rehabilitation.

FIG. 20 is a non-limiting diagram showing the top level architecture of the mobile-cloud implementation of the present invention in an embodiment operable in for physical conditioning, activity monitoring, and rehabilitation. An AI module embodied as an artificial neural network is shown implemented in the Internet cloud, along with a computational framework including data processing and analysis. Researchers and healthcare providers are able to remotely access patient data through a secure and controlled user interface. In some preferred embodiments, patients may access their records as well.

Figure 21:
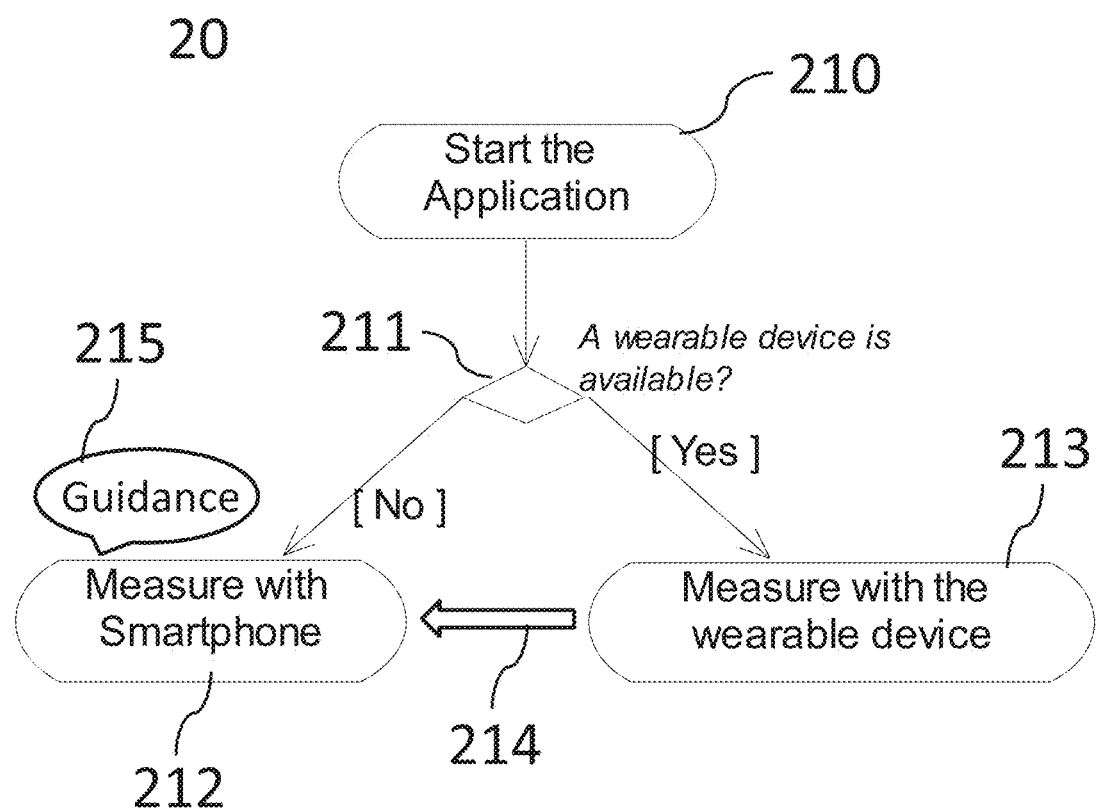
FIG. 21 is a non-limiting diagram showing the beginning workflow of the present invention.

FIG. 21 is a non-limiting diagram showing the beginning workflow of the present invention, the workflow indicating that the application will first try to connect to an available wearable mobile device (e.g., Microsoft Band). If no such device is available, it proceeds to use the smartphone to measure angles (see FIG. 13). Otherwise, it uses the wearable device to measure angles.

Figure 22:
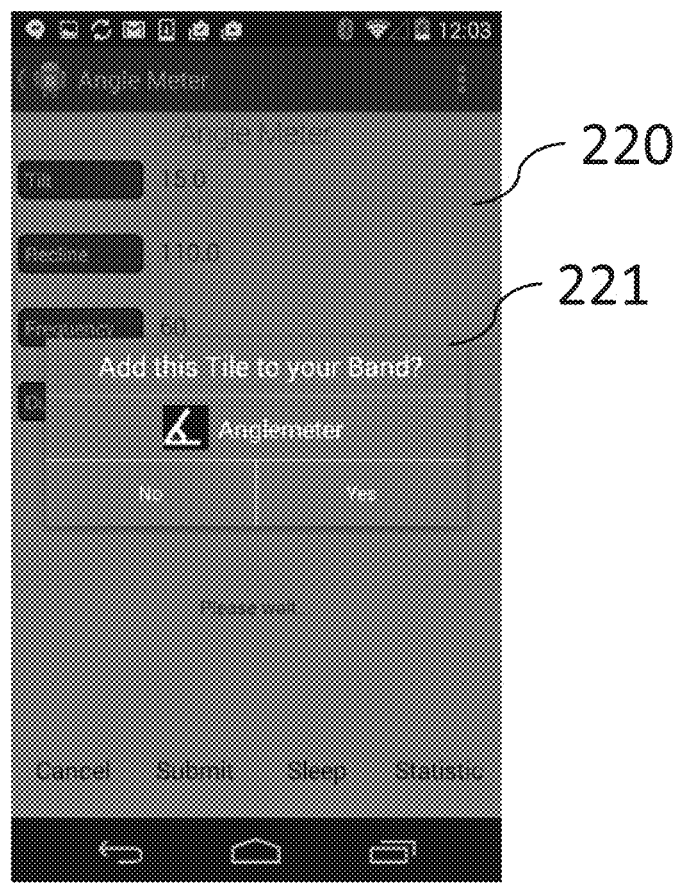
FIG. 22 is a non-limiting diagram showing a screenshot for connecting to a wearable mobile device (Microsoft Band in this example) for the first time of usage.

FIG. 22 is a non-limiting diagram showing a screenshot on a smartphone for connecting to a wearable mobile device (Microsoft Band in this example) for the first time of usage. If the application detects a wearable mobile device (Microsoft Band in this example) for the first time, it asks whether an icon should be added to the wearable device.

Figure 23:
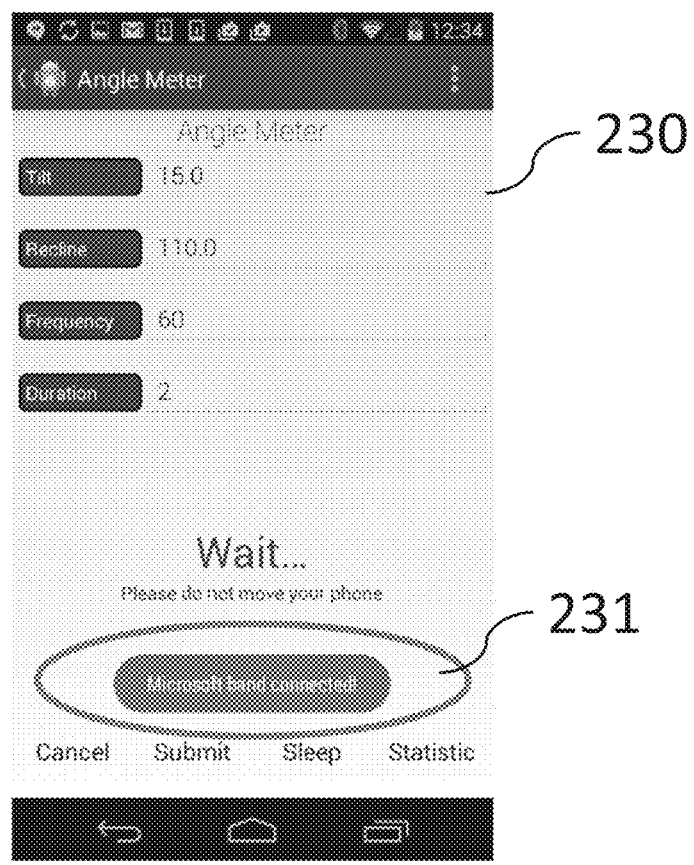
FIG. 23 is a non-limiting diagram showing a screen shot for connecting to a wearable device in the subsequent usage.

FIG. 23 is a non-limiting diagram showing a screen shot on a smartphone for connecting to a wearable device in the subsequent usage (see FIG. 22). It indicates that the connection between the smartphone and the wearable device has been established.

Figure 24:
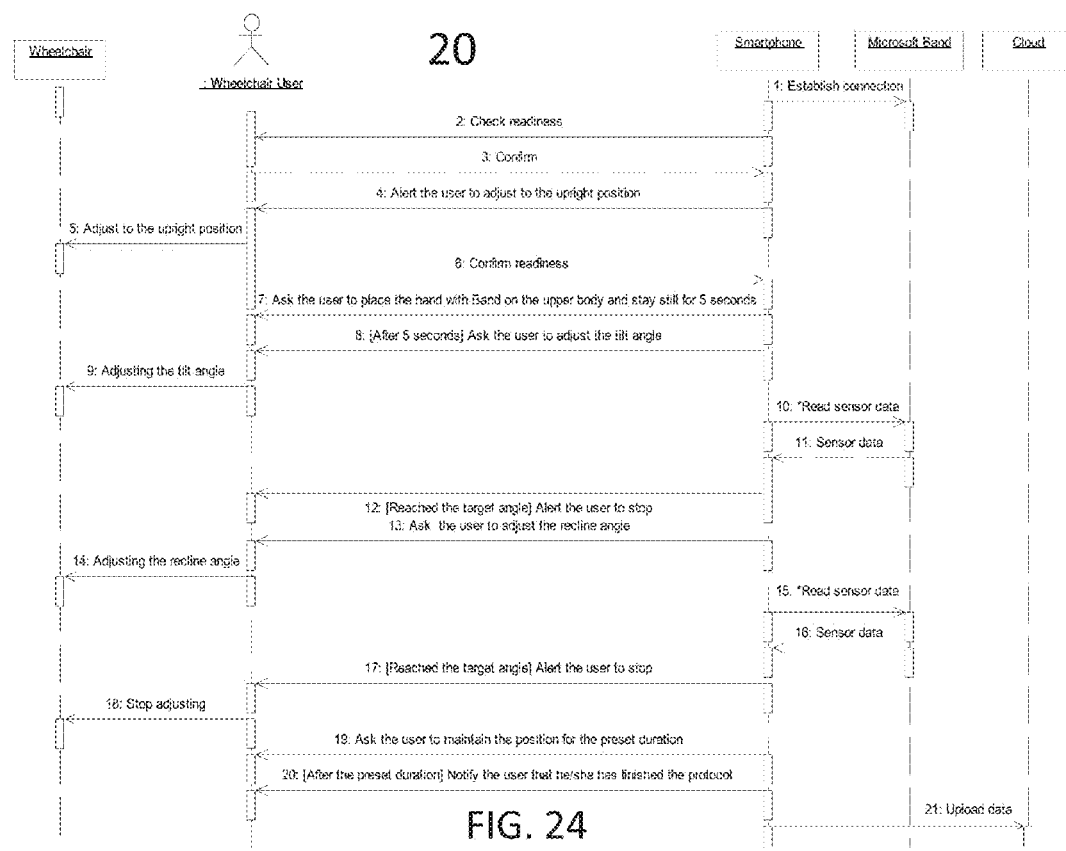
FIG. 24 is a non-limiting diagram showing the interactions among wheelchair user, smartphone, and Microsoft Band.

FIG. 24 is a non-limiting diagram showing the interactions among wheelchair user, smartphone, and Microsoft Band (i.e., wearable device). The wheelchair user interacts with the smartphone and Microsoft Band for effective wheelchair tilt and recline (TR) usage. In step 1, the smartphone establishes the connection with the Microsoft Band through Bluetooth if available (see FIG. 22 and FIG. 23). After connecting, the application sequences from step 2 through step 21.

Figure 25:
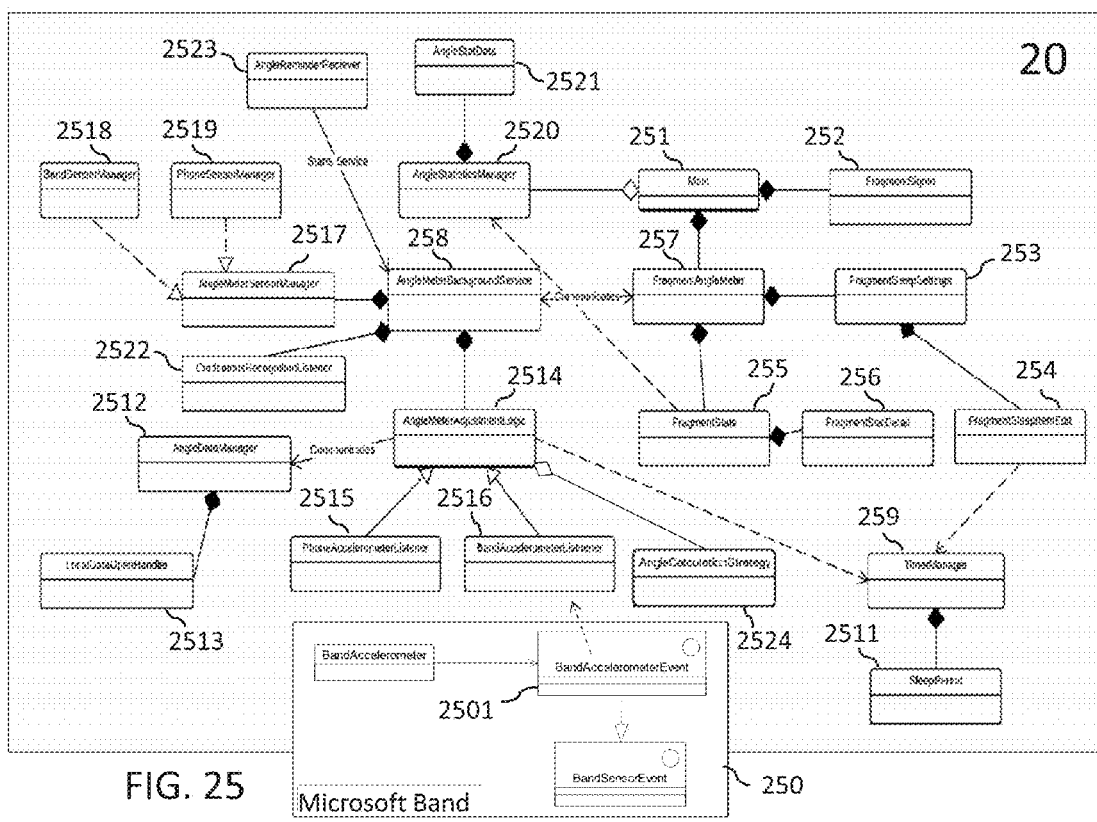
FIG. 25 is a non-limiting diagram showing a Class Diagram for the present invention using Microsoft Band as the wearable motion sensing device.

FIG. 25 is a non-limiting diagram showing a Class Diagram for the present invention using Microsoft Band as the wearable motion sensing device. The invention can retrieve the sensor event (i.e., the built-in BandAccelerometerEvent provided by Microsoft) from Microsoft Band and then guide the wheelchair user based on the event data.

Figure 26:
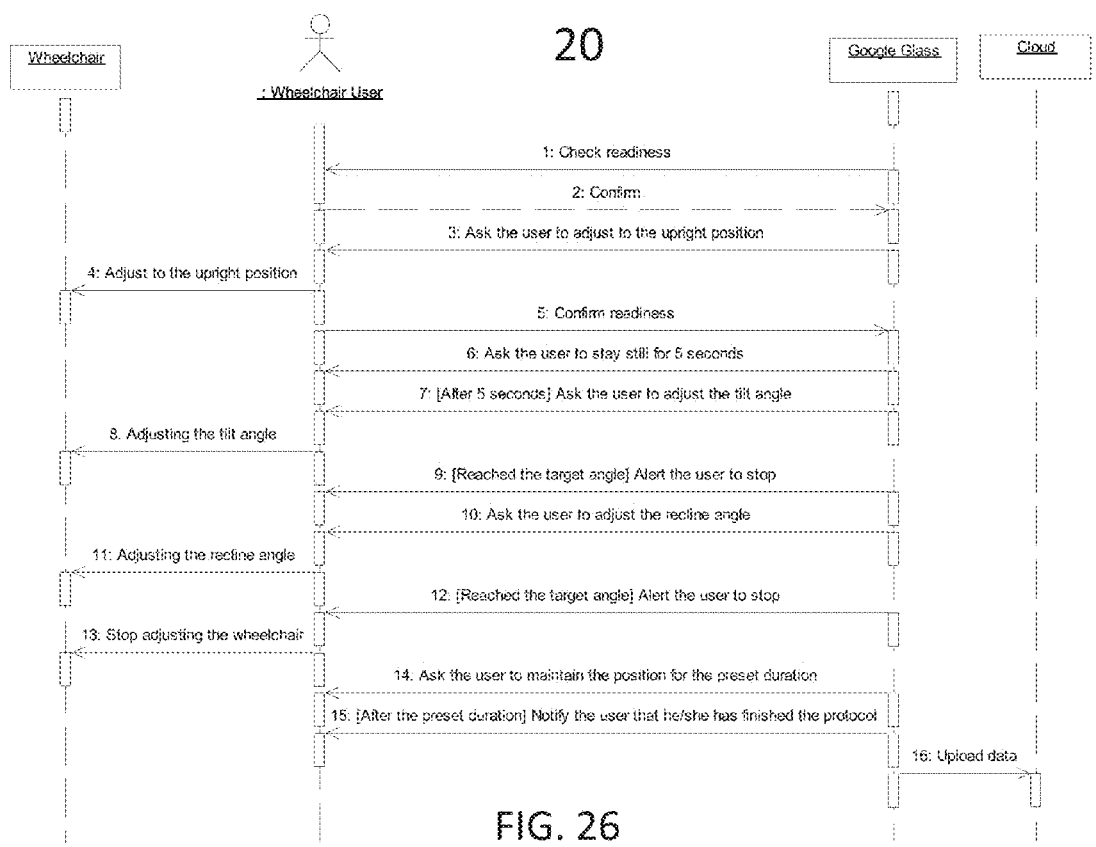
FIG. 26 is a non-limiting diagram showing interactions between a wheelchair user and Google Glass.

FIG. 26 is a non-limiting diagram showing interactions between the wheelchair user and a Google Glass wearable device. In step 1, the Google Glass app checks whether the wheelchair user is ready to perform the wheelchair TR functions. In step 2, the wheelchair user confirms the readiness. Thereafter steps 3 through 16 are executed.

Figure 27:
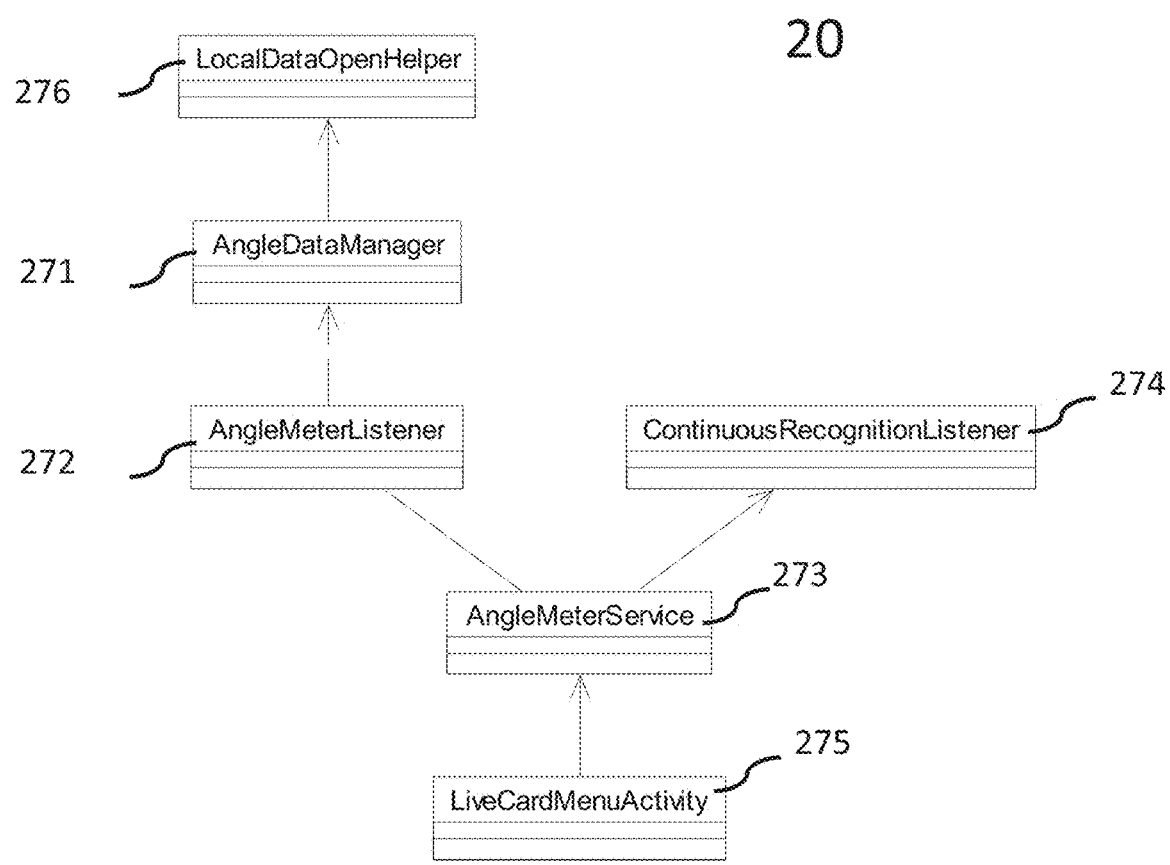
FIG. 27 is a non-limiting diagram showing a Class Diagram for the present invention using Google Glassware.

FIG. 27 is a non-limiting diagram showing a Class Diagram for the present invention using Google Glassware. The diagram shows that the invention can work in Google Glass without relying on smartphones.

Figure 28:
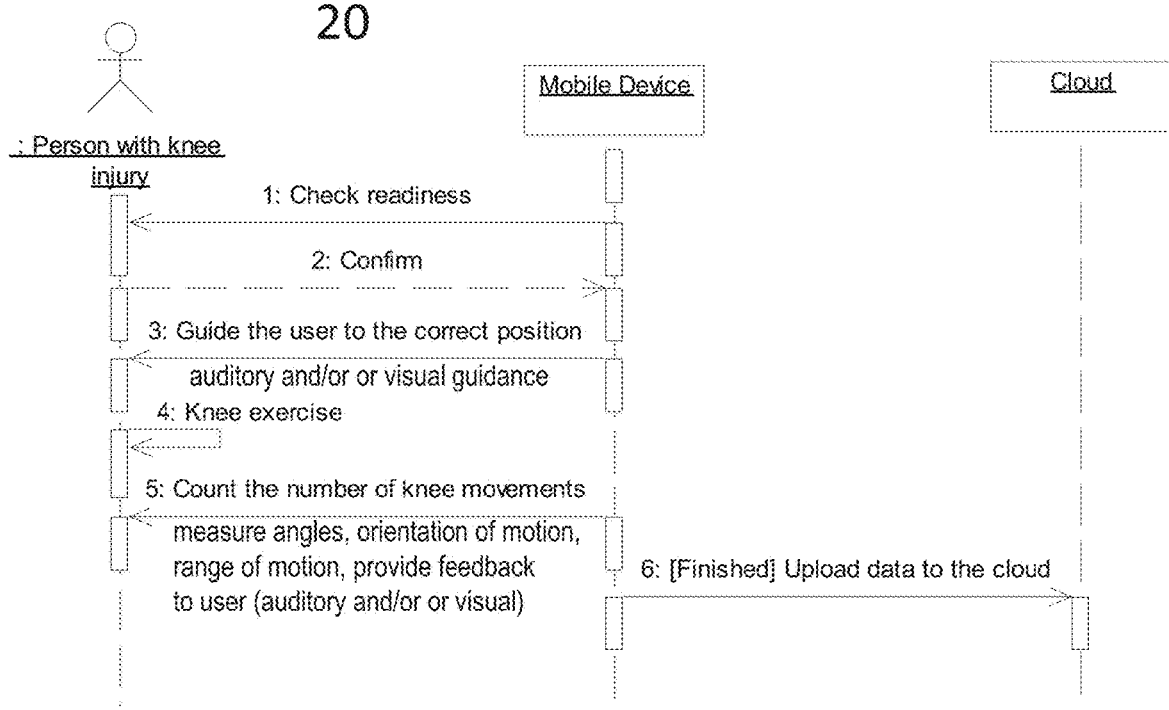
FIG. 28 is a non-limiting diagram showing interaction between a rehabilitation user and a mobile device.

FIG. 28 is a non-limiting diagram showing interaction between a rehabilitation user and a mobile device. In step 1, the mobile device checks whether the person is ready for a conditioning or rehabilitation exercise (e.g., for a knee injury) by using a voice alert, e.g., "It is the time to perform knee exercises. If you are ready, please say ready". In step 2, the person confirms his/her readiness, then sequences through step 6.

Figure 29:
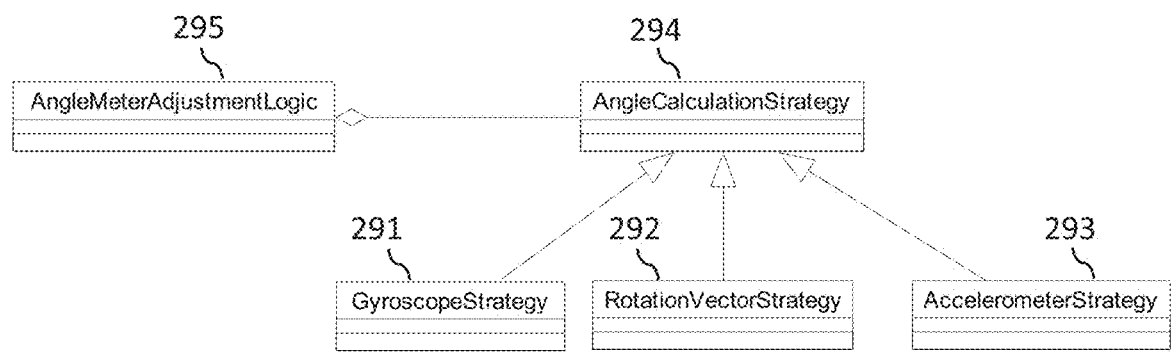
FIG. 29 is a non-limiting diagram showing a Class Diagram for the Knee Recovery App.

FIG. 29 shows a class diagram for knee recovery application, which is built upon the application for wheelchair tilt and recline as shown in FIG. 25. Two more classes were added, namely, GyroscopeStrategy and RotationVectorStrategy.

In detail: Referring now to FIG. 1, a non-limiting schematic illustration of one embodiment of the present invention 10 shows one configuration of the process flow for a typical smartphone implementation of the present invention (i.e., the local version) 10. Users must create their profiles 11 before they can use the system (see FIG. 11a). A profile may include information comprising the user's age, gender, height, weight, body mass index, level of injury, completeness of injury, duration of injury, age at onset of SCI, whether he/she smokes, drinks alcohol, exercises, and/or has pressure ulcer history. The profile is stored locally in the smartphone. Then, the user can proceed to use the implemented smartphone application. The user has the options to update his/her profile 14, retrieve recommendations for wheelchair tilt & recline usage 15, and use the goniometer implemented in the smartphone to measure wheelchair tilt/recline angles 16. Note that the artificial neural networks (ANN) are implemented locally in the smartphone. The ANNs can provide the set of favorable tilt and recline settings and the best tilt and recline setting for individual users based on their profiles.

Referring now to FIG. 2, a non-limiting schematic illustration of one embodiment of the present invention 10 shows one configuration of the process flow for the mobile-to-cloud implementation of the present invention 10 (also see FIG. 19). Users must register 21 to create their profiles before they can login 22. The smartphone application provides the user interface that allows the users to register (i.e., create their own profiles. See FIG. 11a). A profile may include information comprising the user's age, gender, height, weight, body mass index, level of injury, completeness of injury, duration of injury, age at onset of SCI, whether he/she smokes, drinks alcohol, exercises, and/or has pressure ulcer history. In addition, the user needs to choose a user name and password. The profile is then stored in the cloud (see FIG. 19), i.e., the smartphone's communication capability (3G, 4G or WIFI) is used to transmit data to the cloud. If a user can provide a valid user name and password 23, he/she can proceed to use the implemented application operable and running on the smartphone. The user has the options to update his/her profile 24, retrieve recommendations for wheelchair tilt & recline usage 25, and use the goniometer implemented in the smartphone to measure wheelchair tilt/recline angles 26. Note that under the mobile-to-cloud configuration, the artificial neural network (ANN) is implemented in the cloud. The ANN can provide the set of favorable tilt and recline settings and the best tilt and recline setting for individual users based on a user's profile. Under the mobile-to-cloud configuration of the present invention 10, a single artificial intelligent module may be configured to serve a plurality of mobile users, who may use various mobile operating systems, such as iOS, Android, Windows, etc. In the mobile side, the users need to login 22 to the application by providing their user names/passwords. Then, the users may use the application in the same way as a user operating the local version of the present invention 10. The difference is that the information on the guidance of wheelchair tilt and recline usage is retrieved from the cloud. This difference is made transparent to the users. Hence, the users do not have to take care of the complex technical details directed to data storage and computation.

Referring now to FIG. 3, a non-limiting diagram is shown presenting the function of "retrieve wheelchair tilt & recline usage" 30 of the present invention 10 (see also 15 in FIG. 1 and 25 in FIG. 2). Specifically, users can obtain a set of favorable incline angles including tilt and recline combinations 31 that can help reduce the risk of pressure ulcers. An overall picture of a user's favorable tilt and recline settings are presentable, along with choices to adjust seating positions. Users are also presented with the best tilt and recline settings 32 that can most effectively reduce risk of pressure ulcers. Users may select the option "retrieve optimal wheelchair tilt and recline setting". A third option is retrieving the optimal duration and frequency to perform wheelchair tilt and recline. Users may elect to retrieve information directed to how often (i.e., frequency) they should perform wheelchair tilt and recline functions and how long (i.e., duration) each time they should maintain at that tilt and recline setting 33. For example, guidance may be provided such as "perform tilt and recline every 15 minutes (i.e., frequency) and maintain the tilt and recline setting for at least 3 minutes (i.e., duration).

The preferable output includes (1) a range of tilt and recline angles that are favorable for pressure reduction for the user 31; (2) the optimal tilt and recline angles that are most effective in reducing the risk of pressure ulcers 32; and (3) the optimal frequency and duration to perform wheelchair tilt and recline functions 33.

Referring now to FIG. 4a, a non-limiting diagram is shown presenting a screen shot of a user interface 40 in a smartphone implementation of the present invention 10 (i.e., the mobile-to-cloud version). A user can choose "submit" 41 if he/she is an existing user. Otherwise, the user needs to register 42 (see FIG. 11a) before proceeding. All users' profiles are stored in the cloud (see FIG. 19). For an existing user, the smartphone application sends his/her user name and password (collected in FIG. 4a) to the cloud application of the present invention to verify the user's identity. Only valid users can use or gain access to the system. System responses are anticipated to at least user touch and voice commands.

Referring now to FIG. 4b, a non-limiting diagram is shown presenting a screen shot 43 of a user interface in a web implementation of the present invention 10. A user can choose "sign in" 44 if he/she is an existing user. Otherwise, the user needs to register 45 (see FIG. 11b) before proceeding. Under the web implementation, all users' profiles are stored in the cloud. For an existing user, the web application sends his/her user name and password (collected in FIG. 4b) to the cloud application of the present invention to verify the user's identity. Only valid users can use or gain access to the system. System responses are anticipated to at least user touch and voice commands.

Referring now to FIG. 4c, in a preferred implementation, the best known artificial neural network (ANN) is implemented for the present invention 10. ANN has a layered network structure 400, in which the processing units (i.e., neurons) are arranged in layers. The ANN in FIG. 4c consists of three layers, including the input layer 401, the hidden layer 402, and the output layer 403. Neurons in adjacent layers can communicate with each other by sending and receiving signals through the weighted connections. The input/output behavior of a neuron is defined by its internal activation function, which accumulates the input signals and then calculates the outputs. Once the network structure 400 is determined, the learning process proceeds in iterations by tuning the weights of connections using a training algorithm, such as the well-known back-propagation algorithm.

The network structure and weights of the ANN in the application are determined offline by using clinical research data on clinically recommended tilt and recline angles. Specifically, wheelchair users with spinal cord injury were recruited to participate in the research. A testing condition includes a five-minute sitting-induced ischemic period, i.e., the research participant sits in the upright position with no tilt or recline for 5 minutes, and a five-minute pressure relief period, i.e., the research participant sits in a clinically recommended tilt and recline setting for 5 minutes. The skin blood flow was measured throughout the test so that we can know whether a tilt and recline setting is favorable for increasing skin blood flow, which has been widely used to determine the efficacy of wheelchair seating conditions. Then, the skin blood flow data was used to train the ANN to predict tilt and recline settings for individual wheelchair users. Other position parameters may be incorporated as well, such as the elevating leg-rest function of a power wheelchair. The ANN in the invention is fully configurable through adjusting the network structure 400 and weights. The ANN can be replaced by other artificial intelligence techniques, namely, any classification, clustering, and regression techniques, such as support vector machine (SVM), C4.5 decision tree, random forest, etc. The present invention will support such transparency in changing the AI module.

Referring now to FIG. 5, a non-limiting diagram is shown presenting a top-level code structure 50 for a smart device application of the present invention 10 (i.e., the local version). The code structure 50 comprises the following modules: InitActivity 51, ClsTrainer 52, Main 50A, InputData 53, ResultTask 54, FragmentForm 55, FragmentFrequency 56, FragmentAngleMeter 57, IntentService.java 571, FragmentList 58, and FragmentResult 59.

InitActivity.java: This class 51 shows the welcome screen when the application is loading. It calls ClsTrainner 52 to train the classifiers in the backend. Once it finishes initializing classifiers, this activity class will transfer to the Main 50A activity class.

ClsTrainner.java: This class 52 is used to initialize a classifier and regression learner coded in the present invention. The classifier can classify whether a given tilt and recline setting is favorable for an individual with spinal cord injury (SCI) to reduce the risk of pressure ulcer. The regression learner can predict the extent of risk deduction for a given tilt and recline setting. This class runs in the backend as a thread when the application starts.

Main.java: The Main class 50A is the container for all the fragment classes in this application. It provides the overall layout of the application.

FragmentForm.java: This class 55 is used to provide the user interface to input data 53. Users can update their profiles (FIG. 1, 14, FIG. 2, 24) here. It can also call the classifier and regression modules to make new predictions with updated profiles.

FragmentFrequency.java: This class 56 shows to the users the optimal duration and frequency to perform the wheelchair tilt and recline functions. It invokes the daemon thread that is running in the backend to return the optimal duration and frequency to the user interface (UI) thread.

FragmentList.java: This class 58 provides a list of functions that is offered by the smartphone app. It redirects a user to the appropriate functions based on the user's choice.

FragmentResult.java: This class 59 includes the template of My Range, My Optimal, and My Test screens (shown on FIG. 10a) in the application. It shows the up-to-date prediction results obtained from the back-end thread.

InputData.java: This is a singleton class 53 that it has only a single instance in the memory. It contains all the data in this application. It acts as a data store in this application. The trained functions (classifier and regression) as well as user inputs are all stored in this class.

ResultTask.java: The ResultTask class 54 is running in the backend as a daemon thread. Its functionality is to make predictions based on a user's profile (FIG. 1, 14, FIG. 2, 24). This class also answers other requests, such as whether a particular tilt and recline setting is favorable for the user, and returns the result to the UI thread.

FragmentAngleMeter.java: This class 57 provides the goniometer function. It reads the accelerometer sensor in the smartphone and calculates the current angle of the phone orientation for the user. This class provides a novel algorithm to measure wheelchair tilt and recline (TR) angles by using the accelerometer in a smartphone. Specifically, the position of a smartphone is modeled with a vector $v=<\alpha_x, \alpha_y, \alpha_z>$, which represents accelerations in three axes measured by the accelerometer. When the tilt or recline stabilizes to a new angle, accelerations in three axes will change due to the decomposition of the gravity along the new angle of the phone. Then, we utilize the dot product property to calculate angle changes between two vectors (positions):

$$v_1 \cdot v_2 = |v_1| \times |v_2| \times \cos\theta \qquad (1)$$

Or equivalently, $$\theta = \arccos(v_1 \cdot v_2 / |v_1| \times |v_2|) \qquad (2)$$

Hence, no matter how the smartphone is positioned, the TR angle θ between two vectors can be measured. In addition, this class employs the novel text-to-speech technique (see class IntentService.java), which enables the system to use voice alerts to guide wheelchair users for proper TR usage.

IntentService.java: This class 571 implements the Android text-to-speech listener and initializes the text-to-speech function for the subsequent usage.

Referring now to FIG. 6, a non-limiting diagram is shown presenting a top-level data flow for a Web based configuration 60 of the present invention 10. The code structure for a Web based configuration 60 comprises the following modules: Index Page 61 (index.html), Register 611 (SignInServlet), Sign in 612 (SignInServlet), User Welcome Page 62 (welcome.jsp), Profile Page 621 (profile.jsp), Update Profile 6211 (UpdateUserServlet), Check Angle Page 622 (check.jsp), Check Angles 6221 (CheckAnglesServlet), Range of Angles Page 623 (result.jsp), Optimal Angle Page 624 (optimal.jsp), Duration and Frequency Page 625 (duration.jsp), Admin User List Page 63 (admin.jsp), Delete User 631 (DeleteUserServlet), Edit User Page 632 (edituser.jsp), Edit User 64 (UpdateUserServlet), and Create New User 65 (UpdateUserServlet).

Index Page 61 (index.html): Index page 61 is the first web page that a user can access. It provides options for registered users to sign in and for unregistered users to register.

Register 611 (SignInServlet): It is a Java Servlet that is invoked by index.html and allows unregistered users to register and create their own user names and passwords. A Java servlet is a class that is used to extend the functionality of the cloud.

Sign in 612 (SignInServlet): It is a Java servlet used by index.html when to sign in and register users given a username and password.

User Welcome Page 62 (welcome.jsp): It is the welcome page after a user successfully signs in the system.

Profile Page 621 (profile.jsp): This page allows users to create their own profiles including their demographic attributes, neurological information, and pressure ulcer history, etc.

Update Profile 6211 (UpdateUserServlet): It is a servlet class that is invoked by profile.jsp to update the user's profile.

Check Angle Page 622 (check.jsp): This page gives a user the option to check whether a particular wheelchair tilt and recline setting will be favorable for the individual user to reduce pressure ulcer's risk.

Check Angles 6221 (CheckAnglesServlet): It is a servlet class that is invoked by check.jsp to check whether a particular wheelchair tilt and recline setting will be favorable for the individual user to reduce pressure ulcer risk.

Range of Angles Page 623 (result.jsp): This page shows the range of tilt and recline angles that are favorable for reducing pressure ulcers' risk.

Optimal Angle Page 624 (optimal.jsp): This page shows the optimal wheelchair tilt and recline settings that may most effectively reduce risk of pressure ulcers.

Duration and Frequency Page 625 (duration.jsp): This page illustrates the optimal duration and frequency to perform wheelchair tilt and recline functions. For example, the user should perform wheelchair tilt and recline functions every 15 minutes (i.e., frequency) and each time the user should maintain that setting for 3 minutes (i.e., duration).

Admin User List Page 63 (admin.jsp): This is a page designed for administrators, who will maintain users, including "add", "edit", and "delete" users.

Delete User 631 (DeleteUserServlet): It is a Java servlet used by admin.jsp when an administrator attempts to delete an application user.

Edit User Page 632 (edituser.jsp): This is a web page that invokes Servlets to add a new user or update an existing user.

Edit User 64 (UpdateUserServlet): It is a Java servlet used by admin.jsp when an administrator attempts to edit a user's information.

Create New User 65 (UpdateUserServlet): The same UpdateUserServlet can also be used to create a new user.

Referring now to FIG. 7, a non-limiting diagram is shown presenting a top-level control flow of the present invention 10 for mobile-to-cloud configuration using the Android operating system. The code structure 70 includes: Login Screen 71, Register 72, Datastore 721, Sign In 73, User Menu Screen 701 (MenuActivity), Profile Screen 74 (FragmentForm), Check Angle Page 75 (FragmentCheck), Range of Angles Page 76 (FragmentResult), Optimal Angles Page 77 (FragmentOptimal), Duration and Frequency Page 78 (FragmentFrequency), and Goniometer 79 (FragmentAngleAdjustment).

Login Screen 71 (LoginActivity): It is the starting Android activity that calls register and signin methods and redirects user to the MenuActivity 701 if the user name and password are verified successfully. Activity is an Android term that represents a function that a user can perform.

Register 72: It invokes the Datastore class (Datastore.register function) that interacts with the Google App Engine datastore to store new user's information (see FIG. 19).

Datastore 721: This class interacts with the Google App Engine datastore service and is used by both the mobile endpoints and java servlets.

Sign In 73: It invokes the Datastore class (Datastore.signin function) that interacts with the Google App Engine datastore to validate the user's information (see FIG. 19).

User Menu Screen 701 (MenuActivity): It is the main activity that shows the main menu of the system. It consists of the currently selected fragment and a navigation list for changing fragments. A fragment is an Android term that represents a portion of the user interface.

Profile Screen 74 (FragmentForm): It is a fragment that consists of the input fields for user information. Once the button at the bottom of the fragment is pressed, the given information is then updated 741 to the datastore in the cloud (see FIG. 19).

Check Angle Page 75 (FragmentCheck): It is a fragment that determines if the given tilt and recline angles 751 are in the ranges provided by the artificial neural network (see FIG. 19).

Range of Angles Page 76 (FragmentResult): It is a fragment that displays a list of ranges provided by the artificial neural network (see FIG. 19). These ranges are favorable tilt and recline combinations that can help reduce the risk of pressure ulcers.

Optimal Angles Page 77 (FragmentOptimal): It is a fragment that displays the optimal angles of wheelchair tilt and recline provided by the artificial neural network (see FIG. 19).

Duration and Frequency Page 78 (FragmentFrequency): It is a fragment used to check the duration and frequency that the user should perform wheelchair tilt and recline functions. For example, the user should perform wheelchair tilt and recline functions in every 15 minutes (i.e., frequency) and each time the user should maintain that position for 3 minutes (i.e., duration).

Goniometer 79 (FragmentAngleAdjustment): It is a fragment used to display the current angle of the phone. It reads the accelerometer sensor in the smartphone and calculates the current angle of the phone orientation for the user. A desired angle can be set by using the device's menu button. The background of this fragment will turn greener the closer the current angle is to the desired angle.

Referring now to FIG. 8a, a non-limiting diagram is shown presenting a class diagram 80 for GAE (cloud) configuration of the present invention 10 where the classes are used to compute personalized guidance on wheelchair tilt and recline, and interact with the mobile and web applications. The code structure includes: ApplicationUser 81, BloodFlowCore 82, BloodFlowResult 83, Range 84, UserEndpoint 85, CheckAnglesServlet 86, SignInServlet 87, ResultEndpoint 88, UpdateUserServlet 89, DeleteUserServlet 810, SignOutServlet 811, MLP 812, LinearUnit 816, NeuralEnd 817, and NeuralConnection 818.

ApplicationUser 81: consists of all user fields and represents the entity structure stored in the Google App Engine (GAE) datastore.

BloodFlowCore 82: contains methods for interacting with the WEKA API, which is an open source data mining platform and returning the BloodFlowResult object. This is where the artificial neural network is built and angles are returned.

BloodFlowResult 83: contains all output results needed and eventually displayed to the user, including a list of tilt and recline ranges, the optimal angles, and duration and frequency.

Range 84: is a class used to hold one set of tilt and recline ranges.

UserEndpoint 85: this Endpoint class manipulates ApplicationUser entities in the datastore by calling the Datastore class methods. Endpoint classes are located in the GAE source code and are annotated to be generated into an API to be used with Android.

CheckAnglesServlet 86: is a servlet class that checks whether a particular wheelchair tilt and recline setting will be favorable for the individual user to reduce pressure ulcer's risk.

SignInServlet 87: is a Java servlet used when to sign in and register users given a username and password.

ResultEndpoint 88: this endpoint creates a BloodFlowResult object to store results from the runBloodFlowCore method. Endpoint classes are located in the GAE source code and are annotated to be generated into an API to be used with Android.

UpdateUserServlet 89: is a Java servlet used when an administrator attempts to edit a user's information.

DeleteUserServlet 810: is a Java servlet used when an administrator attempts to delete an application user.

SignOutServlet 811: This class provides the sign out function in the web application.

MLP.java 812: The MLP class is customized by adding getNumWeights( ), importWeights( ), and exportWeights( ) methods. These methods allow us to reconstruct ANN if the network structure and weights are provided.

MLP 812, LinearUnit 816, NeuralEnd 817, and NeuralConnection 818 are obtained from WEKA, which is an open source platform for data mining. These classes are used to model the artificial neural network. LinearUnit 816, NeuralEnd 817, and NeuralConnection 818 are used without any customizations.

Referring now to FIG. 8*b*, a non-limiting diagram is shown presenting a class diagram 80 for GAE (cloud) configuration of the present invention 10 where the classes are used to store the tilt and recline usage information (the time when the user performs the tilt and recline functions, the angles of the tilt and recline, etc.) The code structure includes: AngleData 813, DataManager 814, and EMF 815.

AngleData 813: is the data type class that models tilt and recline angle data, which is sent from the mobile client.

DataManager 814: is the class that handles the communication between the client and Google datastore.

EMF 815: EntityManagerFactory helps communication between the Google datastore and the application.

Referring now to FIG. 9, a non-limiting diagram is shown presenting a class diagram 90 for a mobile configuration of the present invention 10 using the Android operating system (complementing FIG. 7). The code structure includes: LoginActivity 91, MenuActivity 92, FragmentForm 921, FragmentCheck 922, FragmentResult 923, FragmentOptimal 924, FragmentFrequency 925, FragmentAngleAdjustment 926, FragmentList 927, Datastore 93, UserEndpoint 94, ResultEndpoint 95, and BloodFlowCore 96.

LoginActivity 91: it is the starting Android activity that calls register and signin methods and redirects user to the MenuActivity 92 if the user name and password are verified successfully. Activity is an Android term that represents a function that a user can perform.

MenuActivity 92: it is the main activity that shows the main menu of the system. It consists of the currently selected fragment and a navigation list for changing fragments. A fragment is an Android term that represents a portion of the user interface.

FragmentForm 921: It is a fragment that consists of the input fields for user information. Once the button at the bottom of the fragment is pressed, the given information is then updated to the datastore in the cloud. A fragment is an Android term that represents a portion of the user interface.

FragmentCheck 922: It is a fragment that determines if the given tilt and recline angles are in the ranges provided by the artificial neural network.

FragmentResult 923: It is a fragment that displays a list of ranges provided by the artificial neural network. These ranges are favorable tilt and recline combinations that can help reduce the risk of pressure ulcers.

FragmentOptimal 924: It is a fragment that displays the optimal angles of wheelchair tilt and recline provided by the artificial neural network.

FragmentFrequency 925: It is a fragment used to check the duration and frequency that the user should perform wheelchair tilt and recline functions. For example, the user should perform wheelchair tilt and recline functions every 15 minutes (i.e., frequency) and each time the user should maintain that setting for 3 minutes (i.e., duration).

FragmentAngleAdjustment 926: It is a fragment used to display the current angle of the wheelchair (tilt or recline). It reads the accelerometer sensor in the smartphone and calculates the current angle of the phone orientation for the user. A desired angle can be set by using the device's menu button. The background of this fragment will turn greener the closer the current angle is to the desired angle.

FragmentList 927: is a fragment that provides a list of functions that is offered by the smartphone app. It redirects a user to the appropriate functions based on the user's choice.

Datastore 93: this class is used by the mobile endpoints to interact with the Google App Engine datastore to manipulate data.

UserEndpoint 94: this Endpoint class manipulates ApplicationUser entities in the datastore by calling the Datastore class methods. Endpoint classes are located in the GAE source code and are annotated to be generated into an API to be used with Android.

ResultEndpoint 95: this endpoint creates a BloodFlowResult object to store results from the runBloodFlowCore method. Endpoint classes are located in the GAE source code and are annotated to be generated into an API to be used with Android.

BloodFlowCore 96: contains methods for interacting with the WEKA API, which is an open source data mining platform and returning the BloodFlowResult object. This is where the artificial neural network is built and angles are returned.

FIG. 10*a* is a non-limiting diagram showing a screen shot of a smartphone implementation of the present invention 10 providing a user interface 101 to access system functions. Both the local mobile version and the mobile-to-cloud version may have the same interface as shown in FIG. 10*a*.

System responses are anticipated and implemented to include at least user touch and voice commands. Audio recitation and response for visually impaired individuals may be provided by the present invention 10. User touch, voice activation and audio recitation functions are generally programmable and operable on industry standard smart devices, such as various device models of iPhone, iPad, Samsung Galaxy, and HP tablets, running operating systems such as Android, iOS, and Windows, where such devices include an accelerometer. Implementation on any such mobile device having the minimum function set as described herein is anticipated.

FIG. 10*b* a non-limiting diagram showing a screen shot of a web-based implementation of the present invention 10 providing a user interface 102 to access system functions. System responses are anticipated and provided in the present invention 10 to include at least user touch and voice commands. Audio recitation and response for visually impaired individuals may also be provided by the present invention 10.

FIG. 11*a* is a non-limiting diagram showing a screen shot of a smartphone implementation of the present invention 10 providing a user interface 110 to enter demographic attributes. System responses are anticipated and provided in the present invention 10 to include at least user touch and voice commands. Audio recitation and response for visually impaired individuals is anticipated and provided by the present invention 10. User touch, voice activation and audio recitation functions are generally programmable and operable on industry standard smart devices, such as various device models of iPhone, iPad, Samsung Galaxy, and HP tablets, running operating systems such as Android, iOS, and Windows, where such devices include an accelerometer. Any such device having the minimum function set as described herein is anticipated.

FIG. 11*b* is a non-limiting diagram showing a screen shot of a web-based implementation of the present invention 10 providing a user interface 112 to enter demographic attributes. System responses are anticipated and provided in the present invention 10 to include at least user touch and voice commands. Audio recitation and response for visually impaired individuals is anticipated and provided by the present invention 10.

FIG. 12*a* is a non-limiting diagram showing a screen shot of a smartphone implementation of the present invention 10 providing a user interface 120 to display favorable tilt and recline angles. System responses are anticipated and provided in the present invention 10 to include at least user touch and voice commands. Audio recitation and response for visually impaired individuals is anticipated and provided by the present invention 10. User touch, voice activation and audio recitation functions are generally programmable and operable on industry standard smart devices, such as various device models of iPhone, iPad, Samsung Galaxy, and HP tablets, running operating systems such as Android, iOS, and Windows, where such devices include an accelerometer. Implementation on any such device having the minimum function set as described herein is anticipated.

FIG. 12*b* is a non-limiting diagram showing a screen shot of a web-based implementation of the present invention 10 providing a user interface 122 to display favorable tilt and recline angles. System responses are anticipated in the present invention 10 to include at least user touch and voice commands. Audio recitation and response for visually impaired individuals is anticipated and provided by the present invention 10.

FIG. 12*c* is a non-limiting diagram showing a screen shot of a smartphone implementation of the present invention 10 providing a user interface 124 to display the best tilt and recline angle for the user. System responses are anticipated and provided in the present invention 10 to include at least user touch and voice commands. Audio recitation and response for visually impaired individuals is anticipated and provided by the present invention 10. User touch, voice activation and audio recitation functions are generally programmable and operable on industry standard smart devices, such as various device models of iPhone, iPad, Samsung Galaxy, and HP tablets, running operating systems such as Android, iOS, and Windows, where such devices include an accelerometer. Implementation on any such device having the minimum function set as described herein is anticipated.

FIG. 12*d* is a non-limiting diagram showing a screen shot of a web-based implementation of the present invention 10 providing a user interface 126 to display the best tilt and recline angle for the user. System responses are anticipated in the present invention 10 to include at least user touch and voice commands. Audio recitation and response for visually impaired individuals is anticipated and provided by the present invention 10.

FIG. 13 is a non-limiting diagram showing the measurement and notification process 130 for determining proper adjustment of tilt and recline settings as determined by the present invention 10. Measurement, display, and auditory notification of tilt and recline angles are accomplished in substantially real-time as a user adjusts tilt and recline settings on a wheelchair. Actionable aural guidance is provided to enable the user to achieve recommended tilt and recline settings suitable to the particular wheelchair user based on his or her specific profile.

The present invention 10 can benefit all wheelchair users, who use a wheelchair with either a tilt or both tilt and recline functions. Both power and manual wheelchair users can benefit from this and other functions of the present invention 10. Healthcare providers and researchers will benefit from the present invention 10, as well. If they use the tilt and recline guidance provided by the present invention 10, the guidance will be automatically provided as inputs to the measurement and notification process 130 implemented in source code and operable on a mobile device. If the health providers and researchers do not use the personalized guidance, the present invention 10 will allow them to input alternative tilt and recline (TR) guidelines (see FIG. 14) to the measurement and notification process 130 so that the wheelchair users can follow those guidelines.

As shown in FIG. 13, in step 1 the wheelchair user uses the goniometer to set the target tilt and recline angles (e.g., 15° tilt/110° recline) and then click the "Submit" button (see FIG. 14). If the wheelchair only has the tilt function, the user only needs to provide the tilt angle.

In step 2, the goniometer asks the wheelchair user to adjust the wheelchair to the upright position (i.e., no tilt or recline). As shown in FIG. 13, the goniometer will use the novel voice alert technique of the present invention 10 to guide the user. For example, the voice alert may recite the non-limiting script "Please make sure that your wheelchair is in the upright position. Touch anywhere on the screen when you are ready!"

In step 3, the wheelchair user adjusts the wheelchair to the upright position following the voice guidance.

In step 4, the wheelchair user touches the screen of the smartphone after the wheelchair has been adjusted to the upright position.

In step 5, the goniometer asks the user to sit still so that the goniometer can record the initial position of the smartphone. This step is needed to ensure the precision of angle calculation. Voice alert is used to guide the user. For example, the voice alert may recite the non-limiting script "Please do not move your phone for five seconds." As shown in FIG. 15, the goniometer may also show the message on the screen.

In step 6, the goniometer may be configured to ask the user to adjust the tilt angle by using a voice alert. For example, the voice alert may recite the non-limiting script "You may now adjust your position. Please adjust your tilt to 15 degrees."

In step 7, the wheelchair user starts to adjust the tilt angle as instructed by the voice alert. In the meantime, the goniometer will measure and display the current tilt angle on the screen of the smartphone as shown in FIG. 16.

In step 8, if the target tilt angle has been reached, the goniometer may be configured to ask the wheelchair user to stop with the voice alert. For example, the voice alert may recite the non-limiting script "Please stop!"

In step 9, the goniometer may be configured to ask the wheelchair user to adjust the recline angle by using the voice alert. For example, the voice alert may recite the non-limiting script "Please adjust your Recline to 110 degrees."

In step 10, the wheelchair user starts to adjust the recline angle. In the meantime, the goniometer will measure and display the current recline angle on the screen of the smartphone as shown in FIG. 17.

In step 11, if the target recline angle has been reached, the goniometer of the present invention may be configured to use an aural instruction where the user may be asked with the voice alert to stop. For example the voice alert may recite the non-limiting script "Please stop! You are now in your target position." In the meantime, the goniometer will also show the final angle and the stop message on the screen of the smartphone as shown in FIG. 18. Note that 90° of recline represents no recline. Hence, for 15° tilt and 110° recline, the final angle should be 15°+(110°−90°)=35°. The present invention considers the lag that occurs when the user hears the voice alert and then stops adjusting the wheelchair position. The present invention calculates the anticipated time to reach the target angle based on the angular speed of wheelchair positioning adjustment. It alerts the user to stop ahead of the anticipated time to compensate the lag.

FIG. 14 is a non-limiting diagram showing an exemplary screenshot of the user interface 140 implemented as an element in the process for determining proper adjustment of tilt and recline settings as determined by the present invention 10. A screenshot for "1: Set the target tilt and recline angles (e.g., 15 tilt/110 recline)" is shown as the first step depicted in FIG. 13. User instructions and alerts displayed may be accompanied by aural instructions.

FIG. 15 is a non-limiting diagram showing an exemplary screenshot of the user interface 150 implemented as an element in the process for determining proper adjustment of tilt and recline settings as determined by the present invention 10. A screenshot for "5: Alert the user to stay still for 5 seconds" is shown as the fifth step depicted in FIG. 13. User instructions and alerts displayed may be accompanied by aural instructions.

FIG. 16 is a non-limiting diagram showing an exemplary screenshot of the user interface 160 implemented as an element in the process for determining proper adjustment of tilt and recline settings as determined by the present invention 10. A screenshot of the display on the user interface while the user adjusts the tilt angle is shown as the seventh step depicted in FIG. 13. User instructions and alerts displayed may be accompanied by aural instructions.

FIG. 17 is a non-limiting diagram showing an exemplary screenshot of the user interface 170 implemented as an element in the process for determining proper adjustment of tilt and recline settings as determined by the present invention 10. A screenshot of the display on the user interface while the user adjusts the recline angle is shown as the tenth step depicted in FIG. 13.

FIG. 18 is a non-limiting diagram showing an exemplary screenshot of the user interface 180 implemented as an element in the process for determining proper adjustment of tilt and recline settings as determined by the present invention 10. A screenshot of the display on the user interface 180 is shown as the eleventh step depicted in FIG. 13. This screenshot occurs when the user has adjusted to the target recline setting. Hence, the wheelchair has been in the target tilt and recline setting. To let user know that the target setting has been reached, the actionable aural guidance is provided to alert the user.

FIG. 19 is a non-limiting diagram showing the top level architecture of the mobile-cloud implementation of the present invention. An artificial neural network is shown implemented in the cloud, along with data processing and analysis. Researchers and healthcare providers are able to remotely access patient data through a secure and controlled interface. The present invention 10 includes a mobile subsystem 191 and a cloud subsystem 192. Specifically, a mobile computing-based subsystem 191 is provided, which uses mobile devices (e.g., smartphones) to manage personal profile, retrieve personalized guidance on wheelchair tilt and recline (TR) usage, measure wheelchair 193 TR angles, and transmit TR usage data. Smartphones provide an ideal platform for implementing the present invention 10 due to the ubiquity of smartphones, their ever-increasing power, and rich set of sensors, such as the accelerometer. The present invention 10 provides a novel algorithm to measure wheelchair 193 TR angles (incline angles) by using the accelerometer in a smartphone. Specifically, the position of a smartphone is modeled with a vector $v=<\alpha_x, \alpha_y, \alpha_z>$, which represents accelerations in three axes measured by the accelerometer. When the tilt or recline stabilizes to a new angle, accelerations in three axes will change due to the decomposition of the gravity along the new angle of the phone. Then, the present invention utilizes the dot product property to calculate angle changes between two vectors (positions):

$$v_1 \cdot v_2 = |v_1| \times |v_2| \times \cos \theta \quad (1)$$

Or equivalently, $$\theta = \arccos(v_1 \cdot v_2 / |v_1| \times |v_2|) \quad (2)$$

Hence, no matter how the smartphone is positioned, the TR angle θ between two vectors can be measured. In addition, the mobile subsystem 191 employs the novel text-to-speech technique, which enables the system to use voice alerts to guide wheelchair users for proper TR usage.

The present invention 10 provides a cloud computing-based subsystem 192 that can provide personalized guidance on wheelchair tilt and recline usage using the artificial neural network, and process, store, and analyze wheelchair 193 TR usage data. This subsystem employs the cloud computing paradigm, which can provide virtually unlimited resources for computation and data storage. Based on the longitudinal TR usage data, the present invention 10 may be used to provide operational applications for mobile devices to evaluate whether wheelchair users adjust enough TR angles to relieve seating pressure and whether they frequently reposition themselves by performing TR functions. The present invention 10 may be used to provide a novel machine-learning approach to analyze historical data of an individual wheelchair user, and assess his or her pressure ulcer (PU) risks correspondingly.

The present invention 10 may use the Google App Engine (GAE) as the cloud computing platform. GAE is managed by Google and provides a platform for developing and hosting web applications. Note that other techniques may be used to replace GAE. Essentially, there are currently three options: (1) continue to use commercial cloud computing platforms, such as Google App Engine, Microsoft Azure, Amazon EC2, etc.; (2) set up a dedicated private cloud computing platform; or (3) use a traditional web server as the data management and computation platform. Other options may emerge in the future and are anticipated as possible web development and hosting solutions to support implementation of various features of the present invention.

The combination of mobile and cloud computing can yield a balanced and integrated system, in which the mobile subsystem 191 will collect user's information, display personalized guidance on TR usage, control the sensor, measure wheelchair TR angles, and transmit TR usage data to the cloud, while the cloud subsystem 192 will handle the subsequent data management and analysis. Therefore, the present invention 10 provides a practical way to improve wheelchair 193 TR usage and capture longitudinal TR usage data among wheelchair users The mobile application of the present invention 10 may be implemented for any mobile operating system, including the mainstream mobile operating systems, such as Google Android, Apple iOS, and Microsoft Windows. To use the mobile application provided by the present invention 10, the user needs to download it from an accessible public source where it may be made available, such as Google Play, Apple Store, or Windows App Store depending on the mobile operating systems they use.

Referring now to FIG. 20, preferred embodiments of the present invention 20 may be adapted to measure flexion and extension of the joints in a skeletal system, physical impact and activity, as well as tilt and recline angles for wheelchair users. Preferred embodiments may comprise using motion and position sensing (goniometer) functions implemented in one or more mobile devices 201 (e.g., smartphone), wearable devices 202 (e.g., smartwatch, fitness band), visual display devices 203 (e.g., Google Glass) and wearable motion sensing devices 50 (e.g. smartgarment 206, smartheadgear 209) for generating and recording personalized parameters in the cloud computing-based subsystem 192 or on a local device 201, 202 or 50 directed to measuring and scoring physical impact, joint range of motion, appendage orientation, and overall physical flexibility. Transferring personalized parameters to the cloud computing-based subsystem 192 facilitates parameter access by clinicians including at least physical therapists, orthopedists, physical medicine clinicians and sports medicine practitioners.

Goniometric measurements (e.g., position, motion, orientation) provided using the present invention 20 may be used as outcome measures (e.g., after a course of treatment), as an exam finding to aid in the diagnosis of a condition, to monitor physical impact and activity, and to determine level of fitness for a specific purpose. System responses are anticipated to at least user 2021 touch and voice commands received 209 from a user 2021 of the mobile device 201 and 202. Audio recitation and response is anticipated. User 2021 touch, voice activation and audio recitation functions are generally programmable and operable on industry standard smart devices 201 such as various device models of iPhone, iPad, Samsung Galaxy, HP tablets, and wearable devices 202 such as AppleWatch, FitBit, Google Glass 203, etc., running on operating systems such as Android, iOS, and Windows. Any such mobile device 201, 202 and 203 having the minimum function set as described herein is anticipated as a useable component in the present invention 20.

Wearable devices, including but not limited to trousers 205, shirts 206, gloves 207, footwear (e.g., socks, shoes) 208, and headgear (e.g., caps, helmets) 209, instrumented with detection devices 50 capable of providing at least goniometer functions (e.g., motion, position, orientation) may be used in preferred embodiments of the present invention 20. In some embodiments the detection devices 50 such as the Intel Cure™ Module may store and process physical parameters. Wearable devices 205, 206, 207, 208, and 209 comprising smartgarments and smartheadgear instrumented with detection devices 50 may be adapted to measure, among other parameters, flexion and extension of the joints in a skeletal system, physical impact and activity, as well as tilt and recline angles for wheelchair users. Measured parameters may be processed locally in the detection device 50 on a wearable device 202, 205, 206, 207, 208, and 209 or transmitted 209, 259, 269, 279, 289, and 299 using for example Bluetooth™ to a computation capable smart device 201 for processing. In some preferred embodiments, parameters measured by detection devices 50 on the wearable devices 202, 205, 206, 207, 208, and 209 may be sent using for example WiFi to the cloud computing-based subsystem 192 for processing and storage, as well as access by clinicians.

Referring now to FIG. 21, a non-limiting diagram shows the beginning workflow of the present invention 20, the workflow indicating at Step 210 that after starting the application will first try at Step 211 to connect to an available wearable mobile device (e.g., Microsoft Band 250 in FIG. 25, Google Glass 203 or smartgarment 208 in FIG. 20). If no such device is available, it proceeds at Step 212 to use the smartphone to measure angles (see FIG. 13). Otherwise, at Step 213 it selects the wearable device to measure orientation, angles, and motion. The sensor data collected by the wearable device (e.g., Microsoft Band 250 in FIG. 25, smartgarment 208 in FIG. 20) is sent at Step 214 to the smartphone (201 in FIG. 20) for processing. Then, the smartphone app processes the sensor data and at Step 215 provides voice guidance for the users. Some mobile devices (e.g., "smart glasses", Google Glass 203) may work independently without the smartphone (201 in FIG. 20). Since wearable devices (e.g., 202 in FIG. 20) are often smaller and easier to carry than a smartphone (201 in FIG. 20), they can make it convenient for users to follow the protocol guidelines (see FIG. 24 and FIG. 25).

FIG. 22 is a non-limiting diagram showing a screenshot 220 on a smartphone (e.g., 201 in FIG. 20) for connecting to a wearable mobile device (Microsoft Band in this example, 250 in FIG. 25) for the first time of usage of the present invention 20. If the application running on the smartphone (e.g., 201 in FIG. 20) detects a wearable mobile device (Microsoft Band in this example, 202 in FIGS. 20 and 250 in FIG. 25) for the first time, it inquires 221 whether an icon should be added to the wearable device (e.g., 202 in FIG. 20). The application program of the present invention 20 that runs in the wearable mobile device (e.g., 202 in FIG. 20) is automatically populated from the smartphone (e.g., 201 in FIG. 20) to the wearable mobile device (e.g., 202 in FIG. 20).

FIG. 23 is a non-limiting diagram showing a screenshot 230 on a smartphone (e.g., 201 in FIG. 20) for connecting to a wearable device (e.g., 202 in FIG. 20) in a subsequent usage (see FIG. 22) of the present invention 20. The display indicates 231 that the connection between the smartphone (e.g., 201 in FIG. 20) and the wearable device (e.g., 202 in FIG. 20) has been established.

Referring now to FIG. 24, a non-limiting diagram shows the interactions in the present invention 20 among a wheelchair user, a smartphone (e.g., 191 in FIG. 19, 201 in FIG. 20), and a Microsoft Band 250 in FIG. 25 (i.e., wearable device). The wheelchair user interacts with the smartphone (e.g., 201 in FIG. 20) and Microsoft Band 250 in FIG. 25 for effective wheelchair tilt and recline (TR) usage. In step 1, the smartphone (e.g., 201 in FIG. 20) establishes the connection with the Microsoft Band 250 in FIG. 25 through Bluetooth if available (see FIG. 22 and FIG. 23). After connecting, the application sequences from step 2 through step 21.

In step 2, the smartphone application audibly and/or visually reminds the wheelchair user of performing wheelchair TR and checks whether the wheelchair user is ready.

In step 3, the wheelchair user confirms his/her readiness.

In step 4, the smartphone application audibly and/or visually directs the wheelchair user to adjust the wheelchair to the upright position (i.e., no tilt or recline). The novel voice alert technique may be used to guide the user, i.e., "Please make sure that your wheelchair is in the upright position. Say ready when you are ready!"

After adjusting to the upright position (step 5), the wheelchair user confirms his/her readiness by saying "ready" (step 6) or signaling in an alternative fashion (e.g., touching the screen).

In step 7, the smartphone application audibly and/or visually directs the wheelchair user to place the arm that wears the Microsoft Band 250 in FIG. 25 on his/her upper body and stay still for 5 seconds. This step is needed to ensure the precision of angle calculation. Voice alert may be used to guide the user—"Please do not move for five seconds."

After 5 seconds (step 8), the smartphone application audibly and/or visually directs the wheelchair user to adjust the tilt angle. While wheelchair user is adjusting the tilt angle (step 9), the smartphone application will read sensor data from the Microsoft Band 250 in FIG. 25 to calculate the angle (steps 10 and 11). Once the prescribed angle is reached, the smartphone application will audibly and/or visually direct the user to stop (step 12) with the voice alert—"Please stop!" or by other means (e.g., a visual alert.)

Then, the smartphone application will audibly and/or visually direct the wheelchair user to adjust the recline angle. Similarly, while the wheelchair user is adjusting the wheelchair 193 in FIG. 19 recline angle (step 14), the smartphone application reads sensor data from the Microsoft Band 250 in FIG. 25 to calculate the recline angle (steps 15 and 16).

Once the prescribed angle is reached, the smartphone application will audibly and/or visually direct the wheelchair user to stop (steps 17 and 18). The present invention 20 considers the lag that occurs when the user hears the voice alert and then stops adjusting the wheelchair position. The invention calculates the anticipated time to reach the target angle based on the angular speed of wheelchair 193 in FIG. 19 position adjustment. It alerts the user to stop ahead of the anticipated time to compensate the lag.

Next, in step 19, the smartphone application of the present invention 20 audibly and/or visually directs the wheelchair user to maintain the current position for a preset duration (e.g., 1 minute). After the preset duration is over, the smartphone application will notify the wheelchair user that he/she has completed the protocol (step 20), and can resume his/her normal activities. The wheelchair TR usage data will be sent to the cloud computing-based subsystem (192 in FIG. 19, 192 in FIG. 20) for storage and analysis (step 21).

Referring now to FIG. 25, the class diagram is shown for the present invention using Microsoft Band 250 as the wearable motion sensing device. The present invention 20 can retrieve the sensor event (i.e., the built-in BandAccelerometerEvent 2501 provided by Microsoft) from Microsoft Band 250 and then guide the wheelchair user based on the event data.

Main 251 is the application's primary Activity. Responsibilities include holding all of the fragments that are used throughout the Lifecycle of the application; launching the appropriate interface for the user to see; and caching the in-memory representation of the statistical data gathered during the adjustments for quick loading in the statistics fragment (i.e., FragmentStats 255).

FragmentSignIn 252 provides a "Sign-in" screen for a new user. The Sign-in screen only gets shown by Main 251 Activity if there is currently no username/password combo stored for the user. This is only on the first run of the application and stops appearing after a username/password combo has been set.

FragmentSleepSettings 253 shows/provides access to user created sleep timers. This fragment presents sleep timers in a list view which shows the times and active days and gives buttons to toggle the active state of each timer. This fragment is responsible for launching FragmentSleepItemEdit 254 on clicking (i.e. activating) one of the timer list items or pressing the add timer button.

FragmentSleepItemEdit 254 allows a user to edit sleep timer settings, and presents an interface to be used to edit an existing sleep timer or create a new one.

FragmentStats 255 provides access to statistics for a given day. This fragment is responsible for launching FragmentStatDetail 256 for a clicked (activated) list item, and parsing the angle data csv file and constructing a data structure to hold the statistics using the AngleStatisticsManager 2520 class.

FragmentStatDetail 256 shows statistical details for a selected day. This fragment is responsible for showing statistical data for each adjustment made on the selected day, and for displaying a graph showing angular displacement over time for selected adjustments.

FragmentAngleMeter 257 provides the Main 251 tilt and recline meter interface. This fragment is responsible for communicating with the AngleMeterBackgroundService 258 to show interface components of a user's adjustment. The FragmentAngleMeter 257 displays angle changing in real time; shows any text based instructions to the user; verifies angle settings before sending them to AngleMeterBackgroundService 258 to start an adjustment; and initializes Microsoft Band 250 tile (if connected).

AngleMeterBackgroundService 258 is responsible for initiating adjustments; providing Text to Speech and Voice Recognition features; notifying a user that it is time to make an adjustment; detecting Microsoft band 250 (if connected); telling AngleDataManager 2512 to send adjustment data to the cloud computing-based subsystem (192 in FIG. 20); interacting with AngleMeterAdjustmentLogic 2514; and setting reminders for future adjustments at appropriate times.

TimerManager 259 holds the list of user created sleep timers and is responsible for checking to see if a sleep timer is currently active; and for writing timers to/recalling timers from internal storage.

Sleep Period 2511 is a data model class to represent a sleep timer. This class holds information relevant to sleep timers, and contains helper methods to determine if a sleep timer is currently active.

AngleDataManager 2512 interacts with Google app engine cloud storage. This class is responsible for uploading angle data to the cloud computing-based subsystem (192 in FIG. 20), and for caching angle data into local SQLLite database if the upload fails so as to try again at a later time.

LocalDataOpenHandler 2513 is an Android helper class for creating and maintaining SQLLite database. This class is responsible for holding angle data until it can be uploaded.

AngleMeterAdjustmentLogic 2514 performs logic needed to carry out an adjustment. This class is responsible for maintaining current adjustment state; proceeding to next step of adjustment as designed; setting reminders for future adjustments by interacting with the Android system through the built-in Android AlarmManager class operating in the mobile device (e.g., 201 in FIG. 20); and recording angle data to the csv file and recording data to be sent to cloud.

PhoneAccelerometerListener 2515 extends AngleMeterAdjustmentLogic 2514 when a smartphone (e.g., 201 in FIG. 20) motion sensor is used. This class is responsible for getting accelerometer data and setting an AngleCalculationStrategy (e.g., 294 FIG. 29) to use for getting angle displacement.

BandAccelerometerListener 2516 extends AngleMeterAdjustmentLogic 2514 when Microsoft Band 250 is used as the motion sensor. This class is responsible for getting accelerometer data and setting an AngleCalculationStrategy (e.g., 294 FIG. 29) to use for getting angle displacement.

AngleMeterSensorManager 2517 provides an interface that declares the actions that need to be carried out when registering and unregistering sensors for use with an AngleMeter application.

BandSensorManager 2518 provides implementation AngleMeterSensorManager 2517 actions when a Microsoft Band 250 is being used.

PhoneSensorManager 2519 provides implementation of AngleMeterSensorManger 2517 actions when smartphone (201 in FIG. 20) motion sensors are being used.

AngleStatisticsManager 2520 parses angle statistic data from the local csv file and stores it in memory for use by the statistics fragments. This class also provides methods to get statistics for a given day and adjustment.

AngleStatData 2521 is a class that represents discrete adjustment angle measurements.

ContinuousRecognitionListener 2522 is responsible for configuring voice recognition and defining voice recognition error handling.

AngleReminderReciever 2523 is a broadcast receiver to handle adjustment reminder intents from the Android system. This class is responsible for notifying the AngleMeterBackgroundService 258 to tell the user that it is time for an adjustment.

AngleCalculationStrategy 2524 is an interface that defines the method for calculating angles.

Referring now to FIG. 26, a non-limiting diagram shows for the present invention 20 interactions between a wheelchair user and a Google Glass (203 in FIG. 20) wearable device.

As shown in step 1, the application of the present invention 20 running on a Google Glass (203 in FIG. 20) wearable device produces an audible and/or visual alert checking whether the wheelchair user is ready to perform the wheelchair TR functions.

In step 2, the wheelchair user confirms audibly and/or by other means (e.g., touch) the user's readiness.

In step 3, the app of the present invention 20 audibly and/or visually directs the wheelchair user to adjust the wheelchair to the upright position (i.e., no tilt or recline). The novel voice alert technique may be used in the app of the present invention 20 to guide the user, i.e., "Please make sure that your wheelchair is in the upright position. Say ready when you are ready!" Other means (e.g., visual) may also be used as guidance.

In step 4, the wheelchair user adjusts the wheelchair to the upright position following the guidance provided by the app of the present invention 20.

In step 5, the wheelchair user confirms his/her readiness after the wheelchair has been adjusted to the upright position.

In step 6, the app of the present invention 20 audibly and/or visually directs the user to sit still so that the Google Glass (203 in FIG. 20) wearable device can record the initial position. This step is needed to ensure the precision of angle calculation. Voice and/or visual alert may be used to guide the user—"Please do not move for five seconds." The app of the present invention 20 will also show the message on the display of the Google Glass (203 in FIG. 20) wearable device.

In step 7, the app of the present invention 20 audibly and/or visually directs the user to adjust the tilt angle by using the voice alert—"You may now adjust your position. Please adjust your tilt to 15 degrees."

In step 8, the wheelchair user starts to adjust the tilt angle as instructed by the voice and/or visual alert. In the meantime, the app of the present invention 20 will measure and display the current tilt angle on the display of the Google Glass (203 in FIG. 20) wearable device.

In step 9, if the target tilt angle has been reached, the app of the present invention 20 audibly and/or visually direct the wheelchair user to stop with the voice and/or visual alert—"Please stop!"

In step 10, the app of the present invention 20 audibly and/or visually directs the wheelchair user to adjust the recline angle by using the voice and/or visual alert—"Please adjust your Recline to 110 degrees."

In step 11, the wheelchair user starts to adjust the recline angle. In the meantime, the app of the present invention 20 will measure and display the current recline angle on the Google Glass (203 in FIG. 20) display.

In step 12, if the target recline angle has been reached, the app of the present invention 20 will audibly and/or visually direct the wheelchair user to stop with the voice and/or visual alert—"Please stop! You are now in your target position." In the meantime, the app of the present invention 20 will also show the final angle and the stop message on the display of the Google Glass (203 in FIG. 20) wearable device. The present invention considers the lag that occurs when the user hears (detects) the voice (visual) alert and then stops adjusting the wheelchair position. The application program of the present invention calculates the anticipated time to reach the target angle based on the angular speed of wheelchair position adjustment. It alerts the user to stop ahead of the anticipated time to compensate the lag.

In steps 13 and 14, the app of the present invention 20 will audibly and/or visually direct the wheelchair user to maintain the current position for the prescribed duration by using voice and/or visual alerts, e.g., "Please maintain the current position for 1 minute".

In step 15, the app of the present invention 20 will notify the wheelchair user that he/she has finished the protocol after the prescribed duration is over.

In step 16, the wheelchair TR usage data will be sent to the cloud for storage and analysis.

Referring now to FIG. 27, the diagram shows that the present invention 20 can work in a Google Glass (203 in FIG. 20) wearable device without relying on smartphones. The description of the classes follows.

AngleDataManager 271 is a service for managing upload of angle data to the cloud. This service 271 maintains a local database of angle data and keeps track of which entries have been uploaded. Once started, the service 271 uploads all entries that have not been uploaded. It then adds any new angle data to the database.

AngleMeterListener 272 is a class for receiving sensor events. This class 272 monitors sensor events. When the sensor, i.e., accelerometer, detects a movement, it will generate a sensor event, including sensor readings in each dimension in the space. This class 272 also maintains the status of wheelchair tilt and recline adjustment and guide the user to finish the protocol.

AngleMeterService 273: A service class for managing the input and output of the application.

This class 273 accepts voice commands from the user and displays angle information on the head-up display of the Google Glass (203 in FIG. 20). This service is bound with AngleMeterListener 272 to guide the user for effective wheelchair tilt and recline usage.

ContinuousRecognitionListener 274 is a class for providing a mechanism for recognizing voice commands and defining voice recognition error handling. This class 274 implements the built-in RecognitionListener in Google Glass (203 in FIG. 20) to perform different actions depending on whether or not too many retries or too much time has passed since speech recognition began. AngleMeterService 273 utilizes this class 274 to achieve its functions.

LiveCardMenuActivity 275 is a class providing the user interface. This class 275 allows users to provide voice commands (i.e., inputs) and then invoke AngleMeterService 273 to handle the command.

LocalDataOpenHelper 276 is a class handling local database for temporary data storage. Before the tilt and recline usage information is sent to the cloud, the data is temporarily stored in the local SQLLite database. This class 276 deals with the local database for temporary data storage.

Referring now to FIG. 28, a non-limiting diagram shows interaction between a rehabilitation user and a mobile device (e.g. FitBit 202, footwear 208 in FIG. 20) running the app of the present invention 20.

In step 1, the app of the present invention 20 running on the mobile/wearable device (e.g. Smartphone 201, FitBit 202, smartgarment 208 in FIG. 20) produces an audible and/or visual alert where the device checks whether the person is ready for a knee (or other orthopedic) exercise by using the voice and/or visual alert, e.g., "It is the time to perform knee exercises. If you are ready, please say ready" (or signal when ready).

In step 2, the person confirms his/her readiness.

In step 3, the mobile device (e.g. FitBit 202, smartphone 201 in FIG. 20) will guide the user to lie down with the right pose by using voice and/or visual guidance, e.g., "Please lie down on your back". Guidance directed to assuming any position appropriate of a particular exercise may be provided.

In steps 4 and 5, while the person performs knee (or other orthopedic) exercises, the mobile device (e.g. FitBit 202, smartgarment 205, smartphone 201 in FIG. 20) will collect sensor data to measure angles, range of motion, orientation of motion, and count the number of knee movements. The app of the present invention 20 provides guidance directed to proper form during exercise. Guidance may be audible and/or visual and use any means appropriate to provide voice instruction and still or motion visual images, including third party "gaming software tools."

In step 6, once the user finishes the protocol, the mobile device (e.g. FitBit 202, smartgarment 205, smartphone 201 in FIG. 20) will send knee movement data to the cloud computing-based subsystem 192 in FIG. 20 for storage and analysis, where movement data may comprise sensor data quantifying angle extension, range of motion, orientation of motion, and the number of knee or other orthopedic movements, and transmission may be accomplished using for example WiFi.

Referring now to FIG. 29, a part of the class diagram for knee recovery application is shown and which is built upon the application for wheelchair tilt and recline as shown in FIG. 25. Two additional classes are included, namely, GyroscopeStrategy 291 and RotationVectorStrategy 292.

GyroscopeStrategy 291 is a class for measuring angles when the movements are parallel with the ground. i.e., the decomposition of gravity along three dimensions remains the same during the movements. The gyroscope sensor in a mobile device (e.g. FitBit 202, smartgarment 208, smartphone 201 in FIG. 20) is used to detect and quantify the angle changes.

RotationVectorStrategy 292 is a class for measuring angles when the movements are parallel with the ground, i.e., the decomposition of gravity along three dimensions remains the same during the movements. This class can be used together with GyroscopeStrategy 291 to cross-validate the results to ensure correct measurement.

AccelerometerStrategy 293 is a class for measuring angles when the movements are not parallel with the ground, i.e., the decomposition gravity among three dimensions keeps changing. The accelerometer sensor is used to calculate the angle changes.

AngleCalculationStrategy 2524 is a class (defined in FIG. 25) that is an interface defining the method for calculating angles.

AngleMeterAdjustmentLogic 2514 is a class (defined in FIG. 25) that performs logic needed to carry out an adjustment.

Additional Embodiments of the Present Invention

Preferred embodiments of the present invention may comprise generating personalized adjustment parameters directed to positioning and control of seating configurations in both commercial and private automotive vehicles, including trucks and passenger cars. Outcome objectives may reflect both safety and comfort. A smartphone implementation providing a user interface to display at least current position and shape parameters and send related control parameters to powered, adjustable seats is anticipated. System responses are anticipated to at least user touch and voice commands. Audio recitation and response is anticipated. User touch, voice activation and audio recitation functions are generally programmable and operable on industry standard smart devices, such as various device models of iPhone, iPad, Samsung Galaxy, HP tablets, Google Glass, Apple Watch, Intel Curie™ Module etc., running on operating systems such as Android, iOS, and Windows, where such devices include an accelerometer or other types of motion sensors. Any such mobile device having the minimum function set as described herein is anticipated. Implementation using on-board devices installed as vehicle equipment is also anticipated.

Preferred embodiments of the present invention may comprise generating personalized adjustment parameters directed to positioning and control of seating configurations in aircraft including both crew and passenger seating. Outcome objectives may reflect both safety and comfort. A smartphone implementation providing a user interface to display at least current position and shape parameters and send related control parameters to powered, adjustable seats is anticipated. System responses are anticipated to at least user touch and voice commands. Audio recitation and response is anticipated. User touch, voice activation and audio recitation functions are generally programmable and operable on industry standard smart devices, such as various device models of iPhone, iPad, Samsung Galaxy, HP tablets, Google Glass, Apple Watch, Intel Curie™ Module, etc., running on operating systems such as Android, iOS, and Windows, where such devices include an accelerometer or other types of motion sensor. Any such mobile device having the minimum function set as described herein is anticipated. Implementation using on-board devices installed as vehicle equipment is also anticipated.

Preferred embodiments of the present invention may comprise generating personalized adjustment parameters directed to positioning and control of seating configurations in furniture, including tilt and recline angle, seat and back shape, firmness and support. Outcome objectives may reflect both safety and comfort. A smartphone implementation providing a user interface to display at least current position and shape parameters and send related control parameters to powered, adjustable seats is anticipated. System responses are anticipated to at least user touch and voice commands. Audio recitation and response is anticipated. User touch, voice activation and audio recitation functions are generally programmable and operable on industry standard smart devices, such as various device models of iPhone, iPad, Samsung Galaxy, HP tablets, Google Glass, Apple Watch, Intel Curie™ Module, etc., running on operating systems such as Android, iOS, and Windows, where such devices include an accelerometer or other types of motion sensor. Any such mobile device having the minimum function set as described herein is anticipated. Implementation using on-board devices installed as furniture components is also anticipated.

Preferred embodiments of the present invention may comprise generating personalized adjustment parameters directed to positioning and control of support and comfort configurations in both commercial and private sleep platforms for healthcare, hospitality and in-home applications. A smartphone implementation providing a user interface to display at least current position and shape parameters, and send related control parameters to powered, adjustable seats is anticipated. System responses are anticipated to at least user touch and voice commands. Audio recitation and response is anticipated. User touch, voice activation and audio recitation functions are generally programmable and operable on industry standard smart devices, such as various device models of iPhone, iPad, Samsung Galaxy, HP tablets, Google Glass, Apple Watch, Intel Curie™ Module, etc., running on operating systems such as Android, iOS, and Windows. Any such mobile device having the minimum function set as described herein is anticipated. Implementation using on-board devices installed as sleep-platform equipment components is also anticipated.

Those skilled in the art will appreciate that in some embodiments of the invention, the functional modules of the Web implementation, as well as the personal and the integrated communication devices, may be implemented as pre-programmed hardware or firmware elements (e.g., application specific integrated circuits (ASICs), electrically erasable programmable read-only memories (EEPROMs), etc.), or other related components. Mobile communication devices that can use the present invention may include but are not limited to any of the "smart" phones or tablet computers equipped with digital displays, wireless communication connection capabilities such as iPhones and iPads available from Apple, Inc., as well as communication devices configured with the Android operating system available from Google, Inc and with the Windows operating system available from Microsoft. In addition, it is anticipated that new types of communication devices and operating systems will become available as more capable replacements of the forgoing listed communication devices, and these may use the present invention as well. New types of motion sensors and motion detection methods may also become available and these devices may be used as components in the present invention, and may be mounted directly or indirectly on the human body.

In other embodiments, the functional modules of the mobile-to-cloud implementation may be implemented by an arithmetic and logic unit (ALU) having access to a code memory which holds program instructions for the operation of the ALU. The program instructions could be stored on a medium which is fixed, tangible and readable directly by the processor, (e.g., removable diskette, CD-ROM, ROM, or fixed disk), or the program instructions could be stored remotely but transmittable to the processor via a modem or other interface device (e.g., a communication adapter) connected to a network over a transmission medium. The transmission medium may be either a tangible medium (e.g., optical or analog communications lines) or a medium implemented using wireless techniques (e.g., microwave, infrared or other transmission schemes).

The program instructions stored in the code memory can be compiled from a high level program written in a number of programming languages for use with many computer architectures or operating systems. For example, the program may be written in assembly language suitable for use with a pixel shader, while other versions may be written in a procedural programming language (e.g., "C") or an object oriented programming language (e.g., "C++" or "JAVA").

In other embodiments, cloud computing may be implemented on a web hosted machine or a virtual machine. A web host can have anywhere from one to several thousand computers (machines) that run web hosting software, such as Apache, OS X Server, or Windows Server. A virtual machine (VM) is an environment, usually a program or operating system, which does not physically exist but is created within another environment (e.g., Java runtime). In this context, a VM is called a "guest" while the environment it runs within is called a "host." Virtual machines are often created to execute an instruction set different than that of the host environment. One host environment can often run multiple VMs at once.

While specific embodiments of the present invention have been described and illustrated, it will be apparent to those skilled in the art that numerous modifications and variations can be made without departing from the scope of the invention as defined in the appended claims. It is understood that the words that have been used are words of description and illustration, rather than words of limitation. Although the invention has been described with reference to particular means, materials and embodiments, the invention is not intended to be limited to the particulars disclosed; rather, the invention extends to all functionally equivalent structures, methods and uses, such as are within the scope of the appended claims.

We claim:

1. A system for guiding and evaluating physical positioning, orientation and motion of a human patient during physical therapy, comprising:
   a cloud computing-based subsystem, said subsystem including an artificial neural network and spatial position analyzer, said artificial neural network and said spatial position analyzer determining personalized boundary values for at least one of said physical positioning, orientation, and motion of said patient, achieved independent of personal mobility devices aiding said positioning, orientation, and motion, and outputting said values;
   at least one of a wearable garment, head gear, or body attachment instrumented with at least one gyroscopic motion sensing device and at least one processing module, said at least one motion sensing device detecting changes and rate of changes in motion, including at least one of said physical positioning, orientation, and movement when worn on said patient, and said at least one processing module receiving from said motion sensing device unprocessed motion change indicators and angle changes between at least two vectors relative to any reference physical orientation of said patient, and outputting said indicators and changes;
   a mobile subsystem receiving personalized boundary values from said cloud computing-based subsystem and receiving said angle changes between at least two vectors relative to any reference physical orientation from said wearable garment, said mobile subsystem comparing said angle changes with said boundary values to quantify degree of deviation, and, thereafter, creating a patient record comprising said changes and said rate of changes in at least one of said physical positioning, orientation, and movement, and transmitting said patient record to said cloud computing-based subsystem,
   said mobile subsystem further providing actionable aural guidance to said patient in substantially real-time to at least one of limiting or actuating changes and said rate of changes in at least one of physical positioning, orientation, and motion relative to said boundary values, and
   said actionable aural guidance provided to said patient including corrective indicators directed to patient performance adjustments to achieve therapeutic motion technique and preclude injury, said indicators responsive to said degree of deviation from said personalized boundary values and gaged patient response to said guidance during prescribed therapeutic exercise.

2. The system of claim 1, wherein said mobile subsystem further includes at least an artificial neural network and spatial position analyzer to operating independently without interacting with said cloud computing-based subsystem.

3. The system of claim 1, wherein said at least one motion sensing device is adapted to mount in a position on said at least one of said garment or body attachment so that arm movements can be measured during physical therapy.

4. The system of claim 1, wherein said at least one motion sensing device mounted on said at least one of said garment or body attachment so that leg movements can be measured during physical therapy.

5. The system of claim 1, wherein said cloud computing-based subsystem includes a specific purpose graphical user interface that displays said patient record and enables monitoring and analysis as to whether patients follow prescribed therapeutic guidelines.

6. The system of claim 1, wherein said boundary values are personalized for a specific individual person.

* * * * *